(12) United States Patent
Respess et al.

(10) Patent No.: US 6,333,195 B1
(45) Date of Patent: Dec. 25, 2001

(54) CROSSLESS RETROVIRAL VECTORS

(75) Inventors: James G. Respess, San Diego; Nicholas J. DePolo, Solana Beach, both of CA (US); Sunil Chada, Missouri City, TX (US); Sybille Sauter, Del Mar, CA (US); Mordechai Bodner; David A. Driver, both of San Diego, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/479,776

(22) Filed: Jan. 7, 2000

Related U.S. Application Data

(63) Continuation of application No. 08/850,961, filed on May 5, 1997, now Pat. No. 6,013,517, which is a continuation-in-part of application No. 08/721,327, filed on Sep. 26, 1996, now abandoned, which is a continuation-in-part of application No. 08/643,411, filed on May 6, 1996, now abandoned, which is a continuation-in-part of application No. 08/437,465, filed on May 9, 1995, now abandoned, which is a continuation-in-part of application No. 08/240,030, filed on May 9, 1994, now abandoned.

(51) Int. Cl.[7] .................. C12N 15/867; C12N 15/63; C12N 15/64; C12N 15/48
(52) U.S. Cl. ................. 435/456; 435/325; 435/455; 435/320.1; 435/363; 435/366; 435/370; 435/371
(58) Field of Search .................................. 435/325, 455, 435/456, 235.1, 320.1, 363, 366, 370, 371, 69.1

(56) References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,800,159 | 1/1989 | Mullis et al. | 435/91.2 |
| 4,939,088 | 7/1990 | Young et al. | 435/69.51 |
| 4,965,195 | 10/1990 | Namen et al. | 435/69.52 |
| 5,037,753 | 8/1991 | Pedersen et al. | 435/235.1 |
| 5,173,414 | 12/1992 | Lebkowski et al. | 435/91.4 |
| 5,278,056 | 1/1994 | Bank et al. | 435/456 |
| 5,591,624 | 1/1997 | Barber et al. | 435/366 |
| 6,013,517 | * 1/2000 | Respess et al. | 435/325 |

FOREIGN PATENT DOCUMENTS

| | | |
|---|---|---|
| 133123 A1 | 2/1985 | (EP) . |
| 173254 A1 | 3/1986 | (EP) . |
| 377842 A1 | 7/1990 | (EP) . |
| 1-128788 | 5/1989 | (JP) . |
| 4-126085 | 4/1992 | (JP) . |
| WO 89/07150 | 9/1989 | (WO) . |
| WO 90/02806 | 3/1990 | (WO) . |
| WO 90/07936 | 7/1990 | (WO) . |
| WO 90/08832 | 8/1990 | (WO) . |
| WO 90/10459 | 9/1990 | (WO) . |
| WO 90/13573 | 11/1990 | (WO) . |
| WO 91/16116 | 10/1991 | (WO) . |
| WO 92/05248 | 4/1992 | (WO) . |
| WO 92/05266 | 4/1992 | (WO) . |
| WO 92/07943 | 5/1992 | (WO) . |
| WO 92/15684 | 9/1992 | (WO) . |
| WO 93/01281 | 1/1993 | (WO) . |
| WO 93/08843 | 5/1993 | (WO) . |
| WO 93/08844 | 5/1993 | (WO) . |
| WO 93/09238 | 5/1993 | (WO) . |
| WO 93/10218 | 5/1993 | (WO) . |
| WO 94/29438 | 12/1994 | (WO) . |
| WO 95/30763 | 11/1995 | (WO) . |
| WO 95/31566 | 11/1995 | (WO) . |
| WO 96/07749 | 3/1996 | (WO) . |

OTHER PUBLICATIONS

Bender et al., "Evidence that the Packaging Signal of Moloney Murine Leukemia Virus Extends into the gag Region" *J. Virology* 61(5):1639–1646, May, 1987.

Bosselman et al., "Repliation–Defective Chimeric Helper Proviruses and Factors Affecting Generation of Competent Virus: Expression of Moloney Murein Leukemia Virus Structural Genes vir the Metallothionein Promoter" *Molecular and Cellular Biology* 7(5):1797–1806, May, 1987.

Danos and Mulligan, "Safe and Efficient Generation of Recombinant Retroviruses With Amphotropic and Ecotropic Host Ranges" *Proc. Natl. Acad. Sci. USA* 85:6460–6464, Sep., 1988.

Markowitz et al., "A Safe Packaging Line for Gene Transfer: Separating Viral Gene on Two Different Plasmids" *J. of Virology* 62(4):1120–1124, Apr., 1988.

Miller and Rosman, "Improved Retroviral Vectors for Gene Transfer and Expression" *Biotechniques* 7(9):980–990, Oct., 1989.

Price et al., "Lineage Analysis in the Vertebrate Nervous System by Retrovirus–Mediated Gene Transfer" *Proc. Natl. Acad. Sci. USA* 84:156–160, Jan., 1987.

Parolin et al., "Analysis in Human Immunodeficiency Virus Type 1 Vectors of cis–Acting Sequences that Affect Gene Transfer into Human Lymphocytes" *J. Virology* 68(6):3888–3895, Jun., 1994.

Neubauer et al., "Construction of a Retroviral Vector for Intracellular Immunization with a HIV Antisense Sequence" *Int. Conf. AIDS* Jul. 19–24, 1992 vol. 8, No. 2, p. A82, Abstract No. POA 2477.

(List continued on next page.)

*Primary Examiner*—David Guzo
(74) *Attorney, Agent, or Firm*—David P. McMasters; Anne S. Dollard; Robert P. Blackburn

(57) ABSTRACT

Retroviral vector constructs are described which have a 5' LTR, a tRNA binding site, a packaging signal, one or more heterologous sequences, an origin of second strand synthesis and a 3' LTR, wherein the vector construct lacks retroviral gag/pol or env coding sequences. In addition, gag/pol, and env expression cassettes are described wherein the expression cassettes lack a consecutive sequence of more than 8 nucleotides in common. The above-described retroviral vector constructs, gag/pol and env expression cassettes may be utilized to construct producer cell lines which preclude the formation of replication competent virus.

44 Claims, 22 Drawing Sheets

OTHER PUBLICATIONS

Roth, "Mutational Analysis of the Carboxyl Terminus of the Moloney Murine Leukemia Virus Integratin Protein" *J. Virology* 65:2141–2145, 1991.

Stuhlmann et al., "Transduction of Cellular neo mRNA by Retrovirus–Mediated Recombination" *J. Virology* 64:5783–5796, 1990.

Miller et al., "Redesign of Retrovirus Packaging Cell Lines to Avoid Recombination Leading to Helper Virus Production" *Molecular and Cellular Biology* 6(8):2895–2902, 1986.

Miller et al., "Factors Involved in Production of Helper Virus–Free Retrovirus Vectors" *Somatic Cell and Molecular Genetics* 12(2):175–183, 1986.

Markowitz et al., "Construction and Use of a Safe and Efficient Amphotorpic Packaging Cell Line" *Virology* 167:400–406, 1988.

Weiss et al., *PNA Tumor Viruses*, Cold Spring Harbor Laboratory, New York, 1985, Chapter 4, pp. 17–73.

Irwin, "Purification and Partial Characterization of the Antiviral Protein from *Phytolacca americana* Which Inhibits Eukaryotic Protein Synthesis" *Archives of Biochemistry and Biophysics* 169:522–528, 1975.

Irvin et al., "Purfication and Properties of a Second Antiviral Protein from *Phytolacca americana* Which Inactivates Eukaryotic Ribosomes" *Archives of Biochemistry and Bophysic* 200:418–425, 1980.

Stirpe et al., "Gelonin, a New Inhibitor of Protein Synthesis, Nontoxic to Intact Cells" *J. Biological Chemistry* 255:6947–6953, 1980.

Martin et al., "Identification and Cloning of Endogenous Retroviral Sequences Present in Human DNA" *Proc. Natl. Acad. Sci. USA* 78:4892–4896, 1981.

Parnes et al., "Mouse $\beta_2$–microglobulin cDNA clones: A Screening Procedure for cDNA Clones Corresponding to Rare mRNAs" *Proc. Natl. Acad. Sci. USA* 78:2253–2257, 1981.

Shinnick et al., "Nucleotide Sequence of Moloney Murine Leukaemai Virus" *Nature* 293:543–548, 1981.

Barbieri et al., "Purification and Partial Characterization of Another Form of the Antiviral Protein From the Seeds of *Phytolacca americana L.* (pokeweed)" *Biochem. J.* 203:55–59, 1982.

Gritz et al., "Plasmid–Encoded Hygromycin B Resistance: the Sequence of Hygromycin B Phosphotransferase Gene and Its Expression in *Escherichia coli* and *Saccharomyces cerevisiae*" *Gene* 25:179–188, 1983.

Jolly et al., "Isolation and Characterization of a Full–Length Expressible cDNA for Human Hypoxanthine Phosphoribosyltransferase" *Proc. Natl. Acad. Sci. USA* 80:477–481, 1983.

Kelly et al., "Nucleotide Sequence of the 3' End of MC 247 Murine Leukemia Virus" *J. Virology* 45:291–298, 1983.

Mekalanos et al., "Cholera Toxin Genes: Nucleotide Sequence Deletion Analysis and Vaccine Development" *Nature* 306:551–557, 1983.

Simonsen et al., "Isolation and Expression of an Altered Mouse Dihydrofolate Reductase cDNA" *Proc. Natl. Acad. Sci. USA* 80:2495–2499, 1983.

Dubensky et al., "Direct Transfection of Viral and Plasmid DNA into the Liver or Spleen of Mice" *Proc. Natl. Acad. Sci. USA* 81:7529–7533, 1984.

Lander et al., "A *Mus dunn* Cell Line that Lacks Sequences Closely Related to Endogenous Murine Leukemia Viruses and can be Infected by Ecotropic, Amphotropic, Xenotropic, and Mink Cell Focus–Forming Viruses" *J. Virology* 52:695–698, 1984.

Miller et al., "Two Base Changes Restore Infectivity to a Noninfectious Molecular Clone of Moloney Murine Leukemia Virus (pMLV–1)" *J Virology* 49:214–222, 1984.

Stanton et al., "Nucleotide Sequence Comparison of Normal and Translocated Murine c–myc Genes" *Nature* 310:423–425, 1984.

Wood et al., "Expression of Active Human Factor VIII from Recombinant DNA Clones" *Nature* 312:330–337, 1984.

Yamamoto et al., "The Human LDL Receptor: A Cysteine–Rich Protein with Multiple Alu Sequences in Its mRNA" *Cell* 39:27–38, 1984.

Boshart et al., "A Very Strong Enhancer is Located Upstream of an Immediate Early Gene of Human Cytomegalovirus" *Cell* 41:521–530, 1985.

Coussens et al., "Tyrosine Kinase Receptor with Extensive Homology to EGF Receptor Shares Chromosal Location with neu Oncogene" *Science* 230:1132–1139, 1985.

Kunkel, "Rapid and Efficient Site–Specific Mutagenesis without Phenotypic Selection" *Proc. Natl. Acad. Sci. USA* 82:488–492, 1985.

Lamb et al., "Nucleotide Sequence of Cloned cDNA Coding for Preproricin" *Eur. J. Biochem.* 148:265–270, 1985.

O'Neill et al., "Envelope and Long Terminal Repeat Sequences of a Cloned Infectious NZB Xenotropic Murine Leukemia Virus" *J. Virology* 53:100–106, 1985.

Tweten et al., "Diptheria Toxin: Effect of Substituting Aspartic Acid for Glutamic Acid 14 on ADP Ribosyltransferase Activity" *J. Biological Chemistry* 260(19):10392–10394, 1985.

Armentano et al., "Effect of Internal Viral Sequences on the Utility of Retroviral Vectors" *J. Virology* 61:1647–1650, 1987.

Bosselman et al., "Replication–Defective Chimeric Helpter Proviruses and Factors Affecting Generation of Competent Virus: Expression of Moloney Murine Leukemia Virus Structural Genes vira the Metallothionein Promoter" *Molecular and Cellular Biology* 7:1797–1806, 1987.

Bzik et al., "Molecular Cloning and Sequence Analysis of the *Plasmodium falciparum* Dihydrofolate Reducatase–Thymidylate Synthase Gene" *Biochemistry* 84:8360–8364, 1987.

Calderwood et al., "Nucleotide Sequence of the Shiga–Like Toxin Genes of *Escherichia coli*" *Biochemistry* 84:4364–4368, 1987.

Carroll et al., "Active Site of *Pseudomonas aeruginosa* Exotoxin A" *J. Biological Chemistry* 262:8707–8711, 1987.

Dorin et al., "A Clue to the Basic Defect in Cystic Fibrosis from Cloning the CF Antigen Gene" *Nature* 326:614–617, 1987.

Jackson et al., "Nucleotide Sequence Analysis of the Structural Genes for Shiga–Like Toxin I Encoded by Bacteriphage 933J from *Escherichia coli*" *Microbial Pathogenesis* 2:147–153, 1987.

Krissansen et al., "Chromosomal Locations of the Gene Coding for the CD3 (T3) γ Subunit of the Human and Mouse CD3/T–cell Antigen Receptor Complexes" *Immunogenetics* 26:258–266, 1987.

Maher, III et al., "Specific Hybridization Arrest of Dihydrofolate Reductase mRNA in vitro Using Anti–Sense Oligonucleotides" *Archives of Biochemistry and Biophysica* 253:214–220, 1987.

Palmer et al., "Efficient Retrovirus–Mediated Transfer and Expression of a Human Adenosine Deaminase Gene in Diploid Skin Fibroblasts from a Adenosine Deaminase–Deficient Human" *Proc. Natl. Acad. Sci. USA* 84:1055–1059, 1987.

Wallner et al., "Primary Structure of Lymphocyte Function–Associated Antigen 3 (LFA–3)" *J. Experimental Medicine* 166:923–932, 1987.

Wang et al., "pH sensitive Immunoliposomes Mediate Target–Cell–Specific Delivery and Controlled Expression of a Foreign Gene in Mouse" *Proc. Natl.. Acad. Sci. USA* 84:7851–7855, 1987.

Borrelli et al., "Targeting of an Inducible Toxic Phenotype in Animal Cells" *Proc. Natl. Acad. Sci. USA* 85:7572–7576, 1988.

Simmons et al., "ICAM, an Adhesion Ligand of LFA–1, is Homologous to the Neural Cell Adhesion Molecule NCAM" *Nature* 331:624–627, 1988.

Altmann et al., "Cotransfectionof ICAM–1 and HLA–DR Reconstitutes Human Antigen–Presenting Cell Functin in Mouse L Cells" *Nature* 338:512–513, 1989.

Fainstein et al., "Nucleotide Sequence Analysis of Human abl and bcr–abl cDNAs" *Oncogene* 4:1477–1481, 1989.

Felgner et al., "Lipfection: A Highly Efficient, Lipid–mediated DNA–Transfection Procedure" *Biochemistry* 84:7413–7417, 1987.

Freeman, et al., "B7, A New Member of the Ig Superfamily with Unique Expression on Activated and Neoplastic B–Cells" ., "B7, A New Member of the Ig Superfamily with Unique Expression on Activated and Neoplastic B–Cells" *J. Immunology* 143:2714–2722, 1989.

Wu et al., "Targeting Genes: Delivery and Persistent Expression of a Foreign Gene Drivin by Mammalian Regulatory Elements in vivo" *J. Biological Chemistry* 264:16985–16987, 1989.

Collins et al., "Primary Amino Acid Sequence of α–Trichosanthin and Molecular Models for Abrin A–chain and α–Trichosanthing" *J. Biological Chemistry* 265:8665–8669, 1990.

Acsadi et al., "Human Dystrophin Expression in mdx Mice After Intramuscular Injection of DNA Constructs" *Nature* 352:815–818, 1991.

Emi et al., "Human Formation of Murine Leukemia Virus with the G Protein of Vesicular Stomatisis Virus" *J. Virology* 65:1202–1207, 1991.

Evensen et al., "Direct Molecular Cloning and Expression of Two Distinct Abrin A–Chains" *J. Biological Chemistry* 266:6848–6852, 1991.

Hakura et al., "Cloning and Characterization of *Salmonella typhimurium* ada Gene Which Encodes $O^6$–Methlguanine–DNA Methyltransferase" *J. Bacteriology* 173:3663–3672, 1991.

Williams et al., "Introduction of Foreign Genes into Tissues of Living Mice by DNA–Coated Microprojectiles" *Proc. Natl. Acad. Sci. USA* 88:2726–2730, 1991.

Wolf et al., "Cloning of cDNA for Natural Killer Cell Stimulatory Factor, A Heterodimeric Cytokine with Multiple Biologic Effects on T and Natural Killer Cells" *J. Immunology* 146:3074–3081, 1991.

Wood et al., "Prepoabrin: Genomic Clonig, Characterisation and the Expression of the A–Chain in *Escherichia coli*" *Eur. J. Biochem.* 198:723–732, 1991.

Chen et al., "The Complete Primary Structure of Abbrin–A B Chain" *FEBS Letters* 309:115–118, 1992.

Curiel et al., "High Efficiency Gene Transfer Mediated by Adenovirus Coupled to DNA–Polylysine Complexes" *Human Gene Therapy* 3:147–154, 1992.

Singer et al., "Intercellular Communication and Cell–Cell Adhesion" *Science* 255:1671–1677, 1992.

Chada et al., "Cross–Reactive Lysis of Human Targets Infected with Prototype and Clinical Human Immunodeficiency Virus Type 1 (HIV–1) Strains by Murine Anti–HIV–1 IIIB env–Specific Cytotoxic T Lymphocytes" *J. Virology* 67:3409–3417, 1993.

Tchenio and Heidmann, "High–Frequency Intracellular Transposition of a Defective Mammalian Provirus Detected by an In Situ Colorimetric Assay" *J. Virology* 66(3):1571–1578, Mar., 1992.

Luo et al., "Template Switching by Reverse Transcriptase During DNA Synthesis" *J. Virology* 64:4321–4328, 1990.

Stuhlmann et al., "Homologous Recombination of Copackaged Retrovirus RNAs During Reverse Transcription" *J. Virology* 66:2378–2388, 1992.

Tchenio et al., "Defective Retroviruses Can Disperse in the Human Genome by Intracellular Transposition" *J. Virology* 65:2113–2118, 1991.

Chattopadhyay et al., "Genomes of Murine Leukemia Viruses Isolated from Wild Mice" *J. Virology* 39:777–791, 1981.

Fiers et al., "Complete Nucleotide Sequence of SV40 DNA" *Nature* 273:113–120, 1978.

Field et al., "Isolation and Characterization of Acycloviru–Resistant Mutants of Herpes Simplex Virus" *J. Gen. Virol.* 49:115–124, 1980.

Morgenstern et al., "Advanced Mammalian Gene Transfer: High Titre Retroviral Vectors with Multiple Drug Selection Markers and a Complementary Helper–Free Packaging Cell Line" *Nucleic Acids Research* 18(12):3587–3596, 1990.

Dougherty et al., "New Retrovirus Helper Cells with Almost no Nucleotide Sequence Homology to Retrovirus Vectors" *J. Virology* 63(7):3209–3212, 1989.

Salmons and Günzburg, "Targeting of Retroviral Vectors for Gene Therapy" *Human Gene Therapy* 4:129–141, 1993.

Jolly et al., *Biotechnology Therapeutics* 2(1–2):179–183, 1990–1991.

* cited by examiner

```
1    ATG GGC CAG ACT GTT ACC ACT CCC TTA AGT TTG ACC TTA GGT CAC TGG AAA
1    Met Gly Gln Thr Val Thr Thr Pro Leu Ser Leu Thr Leu Gly His Trp Lys

52   GAT GTC GAG CGG ATC GCT CAC AAC CAG TCG GTA GAT GTC AAG AAG AGA CGT
18   Asp Val Glu Arg Ile Ala His Asn Gln Ser Val Asp Val Lys Lys Arg Arg

103  TGG GTT ACC TTC TGC TCT GCA GAA TGG CCA ACC TTT AAC GGA TGG CCG
35   Trp Val Thr Phe Cys Ser Ala Glu Trp Pro Thr Phe Asn Val Gly Trp Pro

154  CGA GAC GGC ACC TTT AAC CGA GAC CTC ATC ACC CAG GTT AAG ATC ATC GTC
52   Arg Asp Gly Thr Phe Asn Arg Asp Leu Ile Thr Gln Val Lys Ile Ile Val

205  TTT TCA CCT GGC CCG CAT GGA CAC CCA GTC TAC CCC TTT ATC GTG ACC
69   Phe Ser Pro Gly Pro His Gly His Pro Val Gln Val Pro Tyr Ile Val Thr

256  TGG GAA GCC TTG GCT TTT GAC CCC CCT CCC TGG GTC AAG CCC TTT GTA CAC
86   Trp Glu Ala Leu Ala Phe Asp Pro Pro Pro Trp Val Lys Pro Phe Val His

307  CCT AAG CCT CCT CCT CCA TCC GCC CCG TCT CTC CCC CTC GAA
103  Pro Lys Pro Pro Pro Pro Pro Ser Ala Pro Ser Leu Pro Leu Glu

358  CCT CCT CGT TCG ACC TCG CCT CGA TCC TAT CCA GCC CTC ACT CCT
120  Pro Pro Arg Ser Thr Ser Pro Arg Ser Tyr Pro Ala Leu Thr Pro

Nar I (415)
409  TCT CTA GGC GCC
137  Ser Leu Gly Ala
```

FIG. 9

A TAT ATA TAT ATC GAT ACC   ATG GGG CAA ACC GTG ACT ACC CCT CTG TCC
                           ▲Met Gly Gln Thr Val Thr Thr Pro Leu Ser

CTC ACA CTG GGC CAT TGG AAG GAC GTG GAA AGA ATT GCC CAT AAT CAA AGC
▲Leu Thr Leu Gly His Trp Lys Asp Val Glu Arg Ile Ala His Asn Gln Ser

GTG GAC GTC AAA CGC AGG CGC AGG TGG GTG ACA TTT TGT AGC GCC GAG TGG CCC
▲Val Asp Val Lys Arg Arg Arg Trp Val Thr Phe Cys Ser Ala Glu Trp Pro

ACA TTC AAT GTT GGC TGG CCT AGG GAT GGA ACT TTC AAT CGC GAT CTG ATT
▲Thr Phe Asn Val Gly Trp Pro Arg Asp Gly Thr Phe Asn Arg Asp Leu Ile

ACT CAA GTG AAA ATT AAA GTG TTC AGC CCC GGA CCC CAC GGC CAT CCC GAT
▲Thr Gln Val Lys Ile Lys Val Phe Ser Pro Gly His Pro His Pro Asp

CAA GTT CCT TAT ATT GTC ACA TTC GTG GAG GCT CTC GCT TTC GAT CCA CCT
▲Gln Val Pro Tyr Ile Val Thr Phe Val Glu Ala Leu Ala Phe Asp Pro Pro

TGG GTG AAA CCA CTG CCC TTG CAT CCC GAG AAA CCC CCA CCC CTC CCA CCT
▲Trp Val Lys Pro Leu Pro Leu His Pro Glu Lys Pro Pro Pro Leu Pro Pro

GCT CCT AGC CTG CCT CTG ACC CCC AGC CTC GAG CCC CCA AGC CGA AGC AGC CCC AGG AGC AGC
▲Ala Pro Ser Leu Pro Leu Thr Pro Ser Leu Glu Pro Pro Ser Thr Pro Arg Ser Ser

NarI
TTG TAC CCT GCT CTG ACC CCC AGC CTC GGC GCC AAA  CCT AAA  C
▲Leu Tyr Pro Ala Leu Thr Pro Ser Leu Gly Ala Lys ?  ??????

FIG. 10

| VIRUS | SPECIES OF ISOLATION | TYPE[1] |
|---|---|---|
| AEV (Avian erthroblastosis virus) | chicken | C,X,T |
| ALV (avian leukosis virus) | chicken | C,N or X,N |
| AMV (avian myeloblastosis virus) | chicken | C,X,T |
| ASV (avian sarcoma virus) | chicken | C,X,T |
| BaEV (baboon endogenous virus) | baboon (*Papio ssp.*) | C,N,N |
| B1LN | *P. hamadryas* | |
| M7 | *P. cynocephalus* | |
| M28 | *P. cynocephalus* | |
| PP-1-Lu | *P. papio* | |
| TG-1-K | gelada | |
| BLV (bovine leukemia virus) | cow | C,X,N |
| BSV (bovine syncytial virus) | cow | S,X,N |
| CAEV (caprine arthritis-encephalitis virus) | goat | L,X,N |
| CERV-CI, CERV C-II | *Mus cervicolor* | C,N,N |
| CCC | cat | C,N,N |
| CPC-1 | colobus monkey | C,N,N |
| CSRV (corn snake retrovirus) | corn snake | C, |
| CSV (chick syncytial virus) | chicken | C,X,N |
| DIAV (duck infectious anemia virus) | duck | C,X,N |
| DKV (deer kidney virus) | black-tailed deer | C,N,N |
| DPC-1 | agouti | C,N,N |
| EIAV (equine infectious anemia virus) | horse | C,X,N |
| ESV (Esh sarcoma virus) | chicken | C,X,T |
| FeLV (feline leukemia virus) | cat | C,N or X,N |
| FeSV (feline sarcoma virus) | cat | C,X,T |
| GA (Gardner-Arnstein) | | |
| SM (McDonough) | | |
| ST (Snyder-Theilen) | | |
| FS-1 | *Felis sylvestris* (wildcat) | C,N,N |
| FSFV (feline syncytium-forming virus) | cat | S,X,N |
| FuSV (Fujinami sarcoma virus) | chicken | C,X,T |
| GALV (gibbon ape leukemia virus) | gibbon | C,X,N |
| GLV (goat leukoencephalitis virus) | see CAEV | |
| GPV (golden pheasant virus) | golden pheasant | C,N,N |
| HaLV (hamster leukemia virus) | hamster | C,N,N |
| IVL (induced leukemia virus) | chicken | C,N,N |
| LLV (lymphoid leukosis virus) | see ALV | |
| LPDV (lymphoproliferative disease of turkeys | turkey | C,X,T |
| M432 | *Mus cervicolor* | B,N,N |
| M832 | *Mus caroli* | B,N,N |

[1] The first letter denotes classification: (B) B-type oncovirus; (C) C-type oncovirus; (D) D-type oncovirus; (L) lentvirus; (S) spumavirus. The second letter denotes origin: (N) enogenous; (X) exogenous; (R) recombinant. The third letter denotes ability to indice morphological transformation: (T) transforming (i.e., containing an *onc* sequence); (N) nontransforming; (?) unknown.

FIG. 17A

| | | |
|---|---|---|
| MAC-1 | stumptail monkey | C,N,N |
| Maedi | sheep | L,X,N |
| MAV (myeloblastosis-associated virus) | chicken | C,X,N |
| MC29 (myelocytomatosis virus) | chicken | C,X,T |
| MCF (mink cell focus-inducing virus) | mouse | C,NR,N |
| MH2 (myelocytomatosis virus) | chicken | C,X,T |
| MiLV (mink leukemia virus) | mink | C,N,N |
| MLV (murine leukemia virus) | mouse | C,X or N,N |
|   Ab (Abelson) | | C,X,T |
|   Fr (Friend) | | C,X,N |
|   Graffi | | C,X,N |
|   Gross | | C,N,N |
|   Ki (Kirsten) | | C,X,N |
|   Mo (Moloney) | | C,X,N |
|   Ra (Rauscher) | | C,X,N |
| MMC-1 | rhesus monkey | C,N,N |
| MMTV (mouse mammary tumor virus) | mouse | B,X or N,N |
| MPMV (Mason-Pfizer monkey virus) | rhesus monkey | D,X,N |
| MSV (murine sarcoma virus) | mouse | C,X,T |
|   BALB | | |
|   FBJ (Finkel-Biskis-Jinkins) | | |
|   FBR | | |
|   Gz (Gazdar) | | |
|   Ha (Harvey) | | |
|   Ki (Kirsten) | | |
|   Mo (Moloney) | | |
|   MPV[1] (myeloproliferative) | | |
|   OS2 (osteosarcoma) | | |
| MyLV (myeloid leukemia) | mouse | C,X,N |
| OK10 (myelocytomatosis virus) | chicken | C,X,T |
| OMC-1 | owl monkey | C,N,N |
| PK-15 | pig | C,N,N |
| PO-1-Lu | langur | D,N,N |
| PPV (progressive pneumonia virus) | sheep | L,X,N |
| PRCII, PRCIV (Poultry Research Centre) | chicken | C,X,T |
| R-35 | rat | C,X?,T |
| RaLV (rat leukemia virus) | rat | C,X,N |
| RaSV (rat sarcoma virus) | rat | C,X,T |
| RAV-n (Rous-associated virus) | see ALV | |
| RAV-0 (Rous-associated virus 0) | chicken | C,N,N |
| RAV-60 (Rous-associated virus 60) | chicken | C,R,N |
| RAV-61 (Rous-associated virus 61) | ring-necked pheasant | C,R,N |
| RD114 | cat | C,N,N |
| REAV (reticuloendotheliosis-associated virus) | turkey | C,X,N |

FIG. 17B

| | | |
|---|---|---|
| REV (reticuloendotheliosis virus) | birds | C,X,N |
| REV-T (reticuloendotheliosis virus-transforming | turkey | C,X,T |
| RIF (Rous interference factor) | see ALV | |
| RPL-*n* (Regional Poultry Laboratory) | see ALV | |
| RPV (ring-necked pheasant virus) | ring-necked pheasant | C,R,N |
| RSV (Rous sarcoma virus) | chicken | C,X,T |
| B77 (Bratislava) | | |
| BH (Bryan high titer) | | |
| BS (Bryan standard) | | |
| CZ (Carr-Zilber) | | |
| EH (Engelbreth-Holm) | | |
| HA (Harris) | | |
| PR (Prague) | | |
| SR (Schmidt-Ruppin) | | |
| SFV-*n* (simian foamy virus) | monkey | S,X,N |
| SFFV (spleen focus-forming virus) | mouse | C,X, or R,N or T |
| Friend | | |
| MPV | | |
| Rauscher | | |
| SiSV (simian sarcoma virus) | see SSV | |
| SLV (simian lymphoma virus) | see GALV | |
| SMRV (squirrel monkey retrovirus) | squirrel monkey | D,N,N |
| SMV (simian myelogenous leukemia virus) | see GALV | |
| SSAV (simian sarcoma-associated virus) | woolly monkey | C,X,N |
| SSV (simian sarcoma virus) | woolly monkey | C,X,T |
| TRV-1 | tree shrew | C,N,N |
| UR-*n* (University of Rochester) | chicken | C,X,T |
| Vand C-I | tree mouse | C,N,N |
| Visna | sheep | L,X,N |
| VRV (viper retrovirus) | Russell's viper | C,N,? |
| WMV (woolly monkey virus) | see SSV | |
| WoLV (woolly monkey leukemia virus) | see SSAV | |
| Y73 (Yamaguchi 73) | chicken | C,X,T |

FIG. 17C

CMV Promoter — wobble gag — SVneo — LTR

CMV Promoter — normal gag — SVneo — LTR

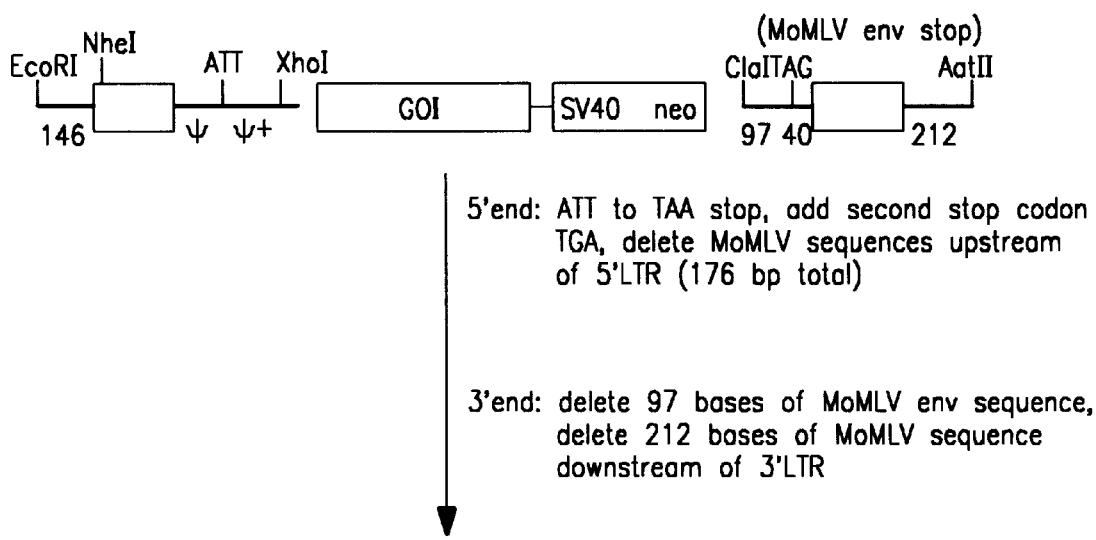
FIG. 20A
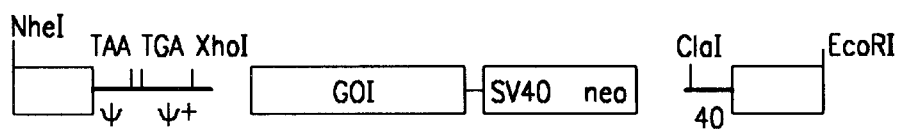
CROSS-LESS RETROVIRAL BACKBONE: pBA-5
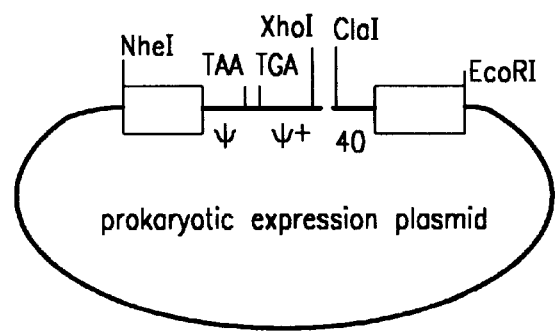
FIG. 20B Unmodified retroviral components (three areas of overlap)

Modified retroviral components (overlap 1 reduced, overlap 2 and 3 eliminated)

Modified retroviral components (overlap 1-3 eliminated)

CROSSLESS RETROVIRAL VECTORS

CROSS-REFERENCE TO RELATED APPLICATION

This application is a continuation of U.S. patent application Ser. No. 08/850,961, filed May 5, 1997, now U.S. Pat. No. 6,013,517, which application is a continuation-in-part of U.S. patent application Ser. No. 08/721,327, filed Sep. 26, 1996, now abandoned; which is a continuation-in-part of U.S. patent application Ser. No. 08/643,411, filed May 6, 1996, abandoned; which is a continuation-in-part of U.S. patent application Ser. No. 08/437,465, filed May 9, 1995, now abandoned; which is a continuation-in-part of U.S. patent application Ser. No. 08/240,030 filed May 9, 1994, now abandoned, all of which are hereby incorporated by reference in their entirety.

TECHNICAL FIELD

The present invention relates generally to retroviral vectors for use in gene transfer, and more specifically, to retroviral vectors which are constructed such that the formation of replication competent virus by recombination is precluded.

BACKGROUND OF THE INVENTION

Retroviruses are RNA viruses which can replicate and integrate into a host cell's genome through a DNA intermediate. This DNA intermediate, or provirus, may be stably integrated into the host's cellular DNA. Retroviruses are known to be responsible for a wide variety of diseases in both man and animals, including for example AIDS and a wide variety of cancers.

Although retroviruses can cause disease, they also have a number of properties that lead them to be considered as one of the most promising techniques for genetic therapy of disease. These properties include: (1) efficient entry of genetic material (the vector genome) into cells; (2) an active efficient process of entry into the target cell nucleus; (3) relatively high levels of gene expression; (4) minimal pathological effects on target cells; and (5) the potential to target particular cellular subtypes through control of the vector-target cell binding and tissue-specific control of gene expression. In using a retrovirus for genetic therapy, a foreign gene of interest may be incorporated into the retrovirus in place of normal retroviral RNA. When the retrovirus injects its RNA into a cell, the foreign gene is also introduced into the cell, and may then be integrated into the host's cellular DNA as if it were the retrovirus itself. Expression of this foreign gene within the host results in expression of foreign protein by the host cell.

Most retroviral vector systems which have been developed for gene therapy are based on murine retroviruses. Briefly, these retroviruses exist in two forms, as proviruses integrated into a host's cellular DNA, or as free virions. The virion form of the virus contains the structural and enzymatic proteins of the retrovirus (including reverse transcriptase), two RNA copies of the viral genome, and portions of the cell's plasma membrane in which is embedded the viral envelope glycoprotein. The genome is organized into four main regions: the Long Terminal Repeat (LTR), and the gag, pol, and env genes. The LTR may be found at both ends of the proviral genome, is a composite of the 5' and 3' ends of the RNA genome, and contains cis-acting elements necessary for the initiation and termination of transcription. The three genes gag, pol, and env are located between the terminal LTRs. The gag and pol genes encode, respectively, internal viral structures and enzymatic proteins (such as integrase). The env gene encodes the envelop glycoprotein (designated gp70 and p15e) which confers infectivity and host range specificity of the virus, as well as the "R" peptide of undetermined function.

An important consideration in using retroviruses for gene therapy is the availability of "safe" retroviruses. Packaging cell lines and vector producing cell lines have been developed to meet this concern. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

There are, however, several shortcomings with the current use of VCLs. One issue involves the generation of "live virus" (i.e., replication competent retrovirus; RCR) by the VCL. Briefly, RCR can be produced in conventional producer cells when: (1) The vector genome and the helper genomes recombine with each other; (2) The vector genome or helper genome recombines with homologous cryptic endogenous retroviral elements in the producer cell; or (3) Cryptic endogenous retroviral elements reactivate (e.g., xenotropic retroviruses in mouse cells).

Another issue is the propensity of mouse based VCLs to package endogenous retrovirus-like elements (which can contain oncogenic gene sequences) at efficiencies close to that with which they package the desired retroviral vector. Such elements, because of their retrovirus-like structure, are transmitted to the target cell to be treated at frequencies that parallel its transfer of the desired retroviral vector sequence.

A third issue is the ability to make sufficient retroviral vector particles at a suitable concentration to: (1) treat a large number of cells (e.g., $10^8$–$10^{10}$); and (2) manufacture vector particles at a commercially viable cost.

In order to construct safer PCLs, researchers have generated deletions of the 5' LTR and portions of the 3' LTR of helper elements (see, Miller and Buttimore, *Mol. Cell. Biol.* 6:2895–2902, 1986). When such cells are used, two recombination events are necessary to form the wild-type, replication competent genome. Nevertheless, results from several laboratories have indicated that even when several deletions are present, RCR may still be generated (see, Bosselman et al., *Mol. Cell. Biol.* 7:1797–1806, 1987; Danos and Mulligan, *Proc. Nat'l. Acad. Sci. USA* 81:6460–6464, 1988). In addition, cell lines containing both 5' and 3' LTR deletions which have been constructed have thus far not proven useful since they produce relatively low titers (Dougherty et al., *J. Virol.* 63:3209–3212, 1989).

One of the more recent approaches to constructing safer packaging cell lines involves the use of complementary portions of helper virus elements, divided among two separate plasmids, one containing gag and pol, and the other containing env (see, Markowitz et al., *J. Virol.* 62:1120–1124; and Markowitz et al., *Virology* 167:600–606, 1988. One benefit of this double-plasmid system is that three recombination events are required to generate a replication competent genome. Nevertheless, these double-plasmid vectors have also suffered from the drawback of including portions of the retroviral LTRs, and therefore remain capable of producing infectious virus.

The present invention overcomes the difficulties of recombination and lower titer associated with many of the prior packaging cell lines, and further provides other related advantages.

SUMMARY OF THE INVENTION

Briefly stated, the present invention provides compositions and methods for the construction of packaging cell lines which preclude the formation of RCR by homologous recombination. Within one aspect of the invention, recombinant retroviral vector constructs (RETROVECTOR™) are provided comprising a 5' LTR, a tRNA binding site, a packaging signal, an original of second strand DNA synthesis, and a 3' LTR, wherein the retroviral vector construct lacks gag/pol and env coding sequences. Within one embodiment of the invention, the retroviral vector construct lacks an extended packaging signal. Within one embodiment, the retroviral vector construct lacks a retroviral nucleic acid sequence upstream of the 5' LTR. Within a preferred embodiment, the retroviral vector constructs lack an env coding sequence upstream of the 5' LTR. Within another embodiment, the retroviral vector constructs lack an env coding and/or untranlated env sequence upstream of the 3' LTR.

Retroviral vector constructs of the present invention may be constructed from one or more retroviruses, including, for example, a wide variety of amphotropic, ecotropic, xenotropic, and polytropic viruses (see e.g., FIGS. 17A, B, and C).

As noted above, retroviral vector constructs of the present invention include one or more heterologous sequences. Within certain embodiments of the invention, the retroviral vector construct further comprising a heterologous sequence that is at least x kb in length, where x is selected from the group consisting of 1, 2, 3, 4, 5, 6, 7 and 8. Within one embodiment, the heterologous sequence is a gene encoding a cytotoxic protein, such as, for example, ricin, abrin, diphtheria toxin, cholera toxin, gelonin, pokeweed, antiviral protein, tritin, Shigella toxin, and Pseudomonas exotoxin A. Within other embodiments the heterologous sequence may be an antisense sequence, or an immune accessory molecule. Representative examples of immune accessory molecules include IL-1, IL-3, IL-4, IL-5, IL-6, IL-7, IL-8, IL-9, IL-10, IL-11, IL-13, and IL-14. Particularly preferred immune accessory molecules may be selected from the group consisting of IL-2, IL-12, IL-15 and gamma-interferon, or the group consisting of ICAM-1, ICAM-2, b-microglobin, LFA3, HLA class I and HLA class II molecules.

Within other embodiments of the invention, the heterologous sequence may encode a gene product that activates a compound with little or no cytotoxicity into a toxic product. Representative examples of such gene products include type I thymidine kinases such as HSVTK and VZVTK, as well as other prodrug-converting enzymes such as cytosine deaminase. Within another embodiment, the heterologous sequence may be a ribozyme. Within yet other embodiments, the heterologous sequence is a replacement gene, which encode proteins such as Factor VIII, ADA, HPRT, CF and the LDL Receptor. Within other embodiments, the heterologous sequence encodes an immunogenic portion of a virus selected from the group consisting of HBV, HCV, HPV, EBV, FeLV, FIV, and HIV.

Within other aspects of the present invention, gag/pol expression cassettes are provided, comprising a promoter operably linked to a gag/pol gene, and a polyadenylation sequence, wherein the gag/pol gene has been modified to contain codons which are degenerate for gag. Within one embodiment, the 5' terminal end of the gag/pol gene lacks a retroviral packaging signal sequence. Within other aspects gag/pol expression cassettes are provided comprising a promoter operably linked to a gag/pol gene, and a polyadenylation sequence, wherein the expression cassette does not co-encapsidate with a replication competent virus.

Within another aspect of the present invention, gag/pol expression cassettes are provided comprising a promoter operably linked to a gag/pol gene, and a polyadenylation sequence, wherein a 3' terminal end of the gag/pol gene has been deleted without effecting the biological activity of integrase. Within one embodiment, a 5' terminal end of the gag/pol gene has been modified to contain codons which are degenerate for gag. Within a further embodiment, the 5' terminal end of the gag/pol gene lacks a retroviral packaging signal sequence. Within other embodiments, the 3' terminal end has been deleted so that nucleotides downstream of nucleotide 5751 or any nucleotide between nucleotide 5751 and 5777 of SEQ ID NO: 1 are deleted.

Within other aspects of the present invention, env expression cassettes are provided, comprising a promoter operably linked to an env gene, and a polyadenylation sequence, wherein no more than 6 retroviral nucleotides are included upstream of the env gene. Within another aspect, env expression cassettes are provided comprising a promoter operably linked to an env gene, and a polyadenylation sequence, wherein the env expression cassette does not contain a consecutive sequence of more than 8 nucleotides which are found in a gag/pol gene. Within yet another aspect, env expression cassettes are provided comprising a promoter operably linked to an env gene, and a polyadenylation sequence, wherein a 3' terminal end of the env gene has been deleted without effecting the biological activity of env. Within one embodiment, the 3' terminal end of the gene has been deleted such that a complete R peptide is not produced by the expression cassette. Within a further embodiment, the env gene is derived from a type C retrovirus, and the 3' terminal end has been deleted such that the env gene includes less than 18 nucleic acids which encode the R peptide. Within a preferred embodiment, the 3' terminal end has been deleted downstream from nucleotide 7748 of SEQ ID NO: 1.

Within various embodiments of the invention, the promoters of the gag/pol and env expression cassettes described above are heterologous promoters, such as CMV IE, the HVTK promoter, RSV promoter, Adenovirus major-later promoter and the SV40 promoter. Within other embodiments, the polyadenylation sequence is a heterologous polyadenylation sequence, such as the SV40 late poly A Signal and the SV40 early poly A Signal.

Within another aspect of the present invention, packaging cell lines are provided, comprising a gag/pol expression cassette and an env expression cassette, wherein the gag/pol expression cassette lacks a consecutive sequence of greater than 20, preferably greater than 15, more preferably greater than 10, and most preferably greater than 8 consecutive nucleotides which are found in the env expression cassette. Within other aspects, producer cell lines are provided comprising a gag/pol expression cassette, env expression cassette, and a retroviral vector construct, wherein the gag/pol expression cassette, env expression cassette and retroviral vector construct lack a consecutive sequence of greater than 20, preferably greater than 15, more preferably greater than 10, and most preferably greater than 8 nucleotides in common. Representative examples of such retroviral vector constructs, gag/pol and env expression cassettes are described in more detail below.

Within yet another aspect of the present invention, producer cell lines are provided comprising a packaging cell line as described above, and a retroviral vector construct. Within another aspect of the present invention, producer cell lines are provided comprising a gag/pol expression cassette, env expression cassette and a retroviral vector construct, wherein the gag/pol expression cassette, env expression cassette and retroviral vector construct lack a consecutive sequence of greater than eight nucleotides in common.

Within particularly preferred embodiments of the invention, packaging cell lines are provided which 'mix and match' various elements of the above described retroviral vector constructs, gag/pol expression cassettes, and env expression cassettes. Briefly, many previous packaging cell lines have three areas of overlap: (1) between the retroviral vector construct and the gag/pol expression cassette; (2) between the gag/pol expression cassette and the env expression cassette; and/or (3) between the env expression cassette and the retroviral vector. As described herein, packaing cell lines and producer cell lines with reduced sequence overlap can be produced with no sequence overlap in area 1, area 2, or area 3 only, a combination of any two (e.g., no sequence overlap in areas 1 and 2 only, no sequence overlap in areas 1 and 3 only, or no sequence overlap in areas 2 and 3 only), or no sequence overlap in any of the three areas. For example, within one aspect of the present invention producer cell lines are provided comprising a gag/pol expression cassette, an env expression cassette and a retroviral vector construct, wherein a 3' terminal end of a gag/pol gene encoded within said gag/pol expression cassette lacks homology with a 5' terminal end of an env gene encoded within said env expression cassette, and wherein a 3' terminal end of said env gene lacks homology with said retroviral vector construct, with the proviso that said retroviral vector construct overlaps with at least 4 nucleotides (and as many as 8, 10, 15, 20, or more nucleotides) of a 5' terminal end of said gag/pol gene encoded within said gag/pol expression cassette. As utilized herein, the phase "lack homology" means that the two cassettes or cassette and construct lack at least 3 or 4, and preferably more than 8, 10, 15 or 20 consecutive nucleotides in common.

Within other aspects of the invention, methods of producing a packaging cell line are provided, comprising the steps of (a) introducing a gag/pol expression cassette as described above into an animal cell; (b) selecting a cell containing a gag/pol expression cassette which expresses high levels of gag/pol, (c) introducing an env expression cassette into said selected cell, and (d) selecting a cell which expresses high levels of env and thereby producing the packaging cell. Within other aspects of the invention, the env expression cassette may be introduced into the cell first, followed by the gag/pol expression cassette. Within other aspects, methods are provided for producing recombinant retroviral particles comprising the step of introducing a retroviral vector construct into a packaging cell as described above. Within preferred embodiments, the retroviral vector construct is one of the retroviral vector constructs described above. As noted above, within any of the methods described herein not all areas of sequence overlap must be eliminated.

Thus, within certain embodiments sequence overlap is not eliminated, for example, between the retroviral vector construct and the gag/pol expression cassette.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 9 is a representative "prewobble" sequence for a MoMLV gag/pol (see also SEQ I.D. Nos. 11 and 12).

FIG. 10 is a representative "wobble" sequence for a MoMLV gag/pol (see also SEQ. I.D. Nos. 9 and 10).

FIGS. 17A, B and C comprise a table which sets forth a variety of retroviruses which may be utilized to construct the retroviral vector constructs, gag/pol expression cassettes and env expression cassettes of the present invention.

FIG. 20 (Parts A–B) is a description of all modifications carried out on retroviral vector as shown in A), resulting in the cross-less retroviral vector shown in B). The cross-less retroviral backbone cloned into a prokaryotic vector is called pBA-5.

DETAILED DESCRIPTION OF THE INVENTION

Figure 1:
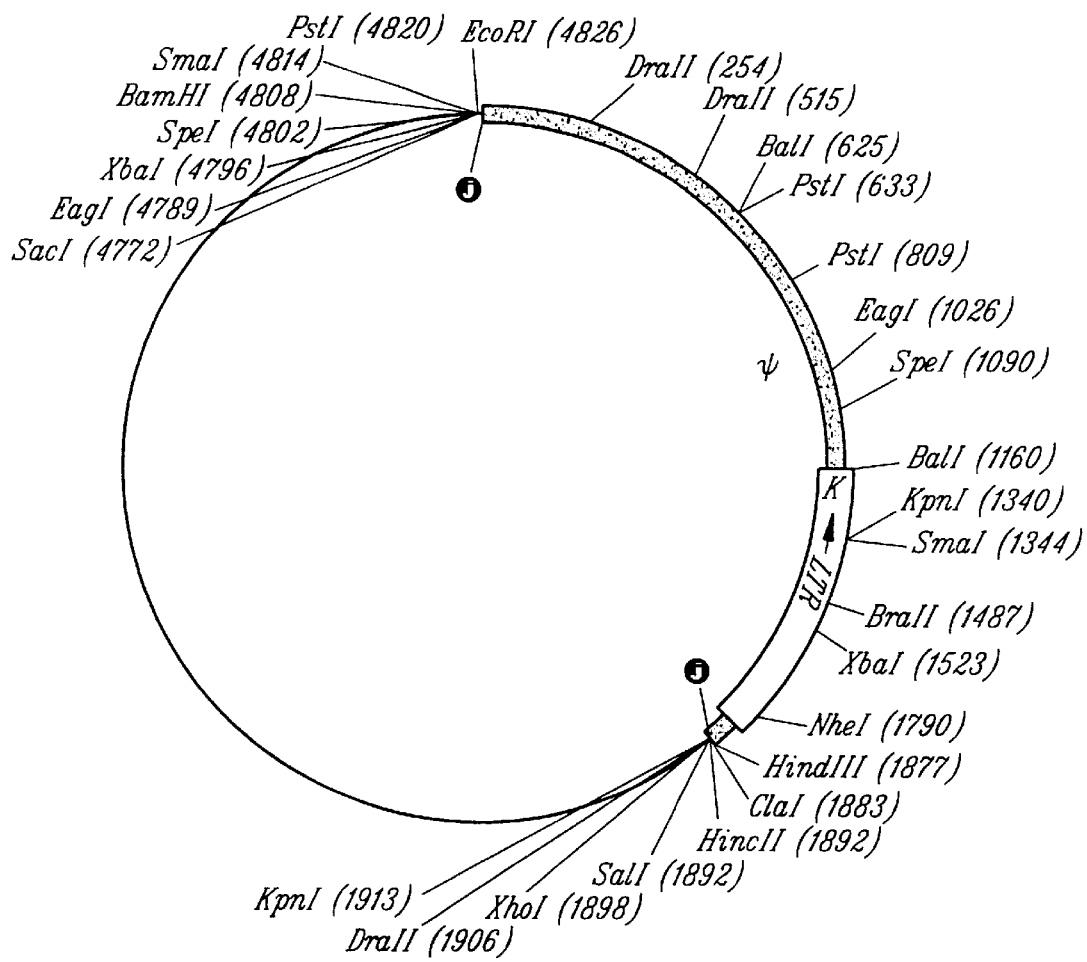
FIG. 1 is a schematic illustration of pKS2+Eco57I-LTR (+).

Prior to setting forth the invention, it may be helpful to an understanding thereof to first set forth definitions of certain terms that will be used hereinafter.

"Retroviral vector construct" refers to an assembly which is, within preferred embodiments of the invention, capable of directing the expression of a sequence(s) or gene(s) of interest. Briefly, the retroviral vector construct must include a 5' LTR, a tRNA binding site, a packaging signal, an original of second strand DNA synthesis and a 3' LTR. A variety of heterologous sequences may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence). Alternatively, the heterologous sequence may merely be a "stuffer" or "filler" sequence, which is of a size sufficient to allow production of viral particles containing the RNA genome. Preferably, the heterologous sequence is at least 1, 2, 3, 4, 5, 6, 7 or 8 kB in length.

The retroviral vector construct may also include transcriptional promoter/enhancer or locus defining element(s), or other elements which control gene expression by means such as alternate splicing, nuclear RNA export, post-translational modification of messenger, or post-transcriptional modification of protein. Optionally, the retroviral vector construct may also include selectable markers such as Neo, TK, hygromycin, phleomycin, histidinol, human placetal Alkaline Phosphatase, NGFR or DHFR, as well as one or more specific restriction sites and a translation termination sequence.

"Expression cassette" refers to an assembly which is capable of directing the expression of the sequence(s) or gene(s) of interest. The expression cassette must include a promoter which, when transcribed, is operably linked to the sequence(s) or gene(s) of interest, as well as a polyadenylation sequence. Within preferred embodiments of the invention, both the promoter and the polyadenylation sequence are from a source which is heterologous to the helper elements (i.e., gag/pol and env). Expression cassettes of the present invention may be utilized to express a gag/pol gene or an env gene. In addition, the expression cassettes may also be utilized to express one or more heterologous sequences either from a gag/pol and/or env expression cassette, or from a entirely different expression cassette.

Within preferred embodiments of the invention, the expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

Preparation of Retroviral vector constructs, Gag/Pol Expression Cassettes and Env Expression Cassettes As noted above, the present invention provides compositions and methods for constructing packaging cells which prelude the formation of replication competent virus by homologous recombination. The following sections describe the preparation of retroviral vector constructs, gag/pol expression cassettes, and env expression cassettes.

1. Construction of retroviral vector constructs

Within one aspect of the present invention, retroviral vector constructs are provided comprising a 5' LTR, a tRNA binding site, a packaging signal, an origin of second strand DNA synthesis and a 3' LTR, wherein the vector construct lacks gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located with U3. LTR's may be readily identified in the provirus due to their precise duplication at either end of the genome.

The tRNA binding site and origin of second strand DNA synthesis are also important for a retrovirus to be biologically active, and may be readily identified by one of skill in the art. For example, tRNA binds to a retroviral tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the original of second strand DNA synthesis is, as its name implies, important for the second strand DNA synthesis of a retrovirus. This region, which is also referred to as the poly-purine tract, is located just upstream of the 3' LTR.

In addition to 5' and 3' LTRs, a tRNA binding site, and an origin of second strand DNA synthesis, retroviral vector constructs of the present invention also comprise a packaging signal, as well as one or more heterologous sequences, each of which is discussed in more detail below.

Retroviral vector constructs of the present invention may be readily constructed from a wide variety of retroviruses, including for example, B, C, and D type retroviruses as well as spumaviruses and lentiviruses (see RNA Tumor Viruses, Second Edition, Cold Spring Harbor laboratory, 1985). Briefly, viruses are often classified according to their morphology as seen under electron microscopy. Type "B" retroviruses appear to have an eccentric core, while type "C" retroviruses have a central core. Type "D" retroviruses have a morphology intermediate between type B and type C retroviruses. Representative examples of suitable retroviruses include those set forth below in FIGS. 17A, B and C (see RNA Tumor Viruses at pages 2–7), as well as a variety of xenotropic retroviruses (e.g., NZB-X1, NZB-X2 and $NZB_{9-1}$ (see O'Neill et al., *J. Vir.* 53:100–106, 1985)) and polytropic retroviruses (e.g., MCF and MCF-MLV (see Kelly et al., *J. Vir.* 45(1):291–298, 1983)). Such retroviruses may be readily obtained from depositories or collections such as the American Type Culture Collection ("ATCC"; Rockville, Md.), or isolated from known sources using commonly available techniques.

Particularly preferred retroviruses for the preparation or construction of retroviral vector constructs of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus, Gibbon Ape Leukemia Virus, Mason Pfizer Monkey Virus, and Rous Sarcoma Virus. Particularly preferred Murine Leukemia Viruses include 4070A and 1504A (Hartley and Rowe, *J. Virol.* 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Particularly preferred Rous Sarcoma Viruses include Bratislava, Bryan high titer (e.g., ATCC Nos. VR-334, VR-657, VR-726, VR-659, and VR-728), Bryan standard, Carr-Zilber, Engelbreth-Holm, Harris, Prague (e.g., ATCC Nos. VR-772, and 45033), and Schmidt-Ruppin (e.g. ATCC Nos. VR-724, VR-725, VR-354).

Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning:*

A Laboratory Manual, 2d ed., Cold Spring Harbor Laboratory Press, 1989; Kunkle, PNAS 82:488, 1985). Further, within certain embodiments of the invention, portions of the retroviral vector construct may be derived from different retroviruses. For example, within one embodiment of the invention, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus. Similarly, portions of a packaging cell line may be derived from different viruses (e.g., a gag/pol expression cassette may be constructed from a Moloney Murine Leukemia Virus, and an env expression cassette from a Mason Pfizer Monkey virus).

As noted above, within various aspects of the present invention, retroviral vector constructs are provided which have packaging signals, and which lack both gag/pol and env coding sequences. As utilized within the context of the present invention, a packaging signal should be understood to refer to that sequence of nucleotides which is not required for synthesis, processing or translation of viral RNA or assembly of virions, but which is required in cis for encapsidation of genomic RNA (see Mann et al., Cell 33:153–159, 1983; RNA Tumor Viruses, Second Edition, supra). Further, as utilized herein, the phrase "lacks gag/pol or env coding sequences" should be understood to refer to retrovectors which contain less than 20, preferably less than 15, more preferably less than 10, and most preferably less than 8 consecutive nucleotides which are found in gag/pol or env genes, and in particular, within gag/pol or env expression cassettes that are used to construct packaging cell lines for the retroviral vector construct. Representative examples of such retroviral vector constructs are set forth in more detail below and in Example 1.

As an illustration, within one embodiment of the invention construction of retroviral vector constructs which lack gag/pol or env sequences may be accomplished by preparing retroviral vector constructs which lack an extended packaging signal. As utilized herein, the phrase "extended packaging signal" refers to a sequence of nucleotides beyond the minimum core sequence which is required for packaging, that allows increased viral titer due to enhanced packaging. As an example, for the Murine Leukemia Virus MoMLV, the minimum core packaging signal is encoded by the sequence (counting from the 5' LTR cap site) from approximately nucleotide 144 of SEQ. I.D. No. 1, up through the Pst I site (nucleotide 567 of SEQ. I.D. No. 1). The extended packaging signal of MoMLV includes the sequence beyond nucleotide 567 up through the start of the gag/pol gene (nucleotide 621), and beyond nucleotide 1040. Thus, within this embodiment retroviral vector constructs which lack extended packaging signal may be constructed from the MoMLV by deleting or truncating the packaging signal downstream of nucleotide 567.

Within other embodiments of the invention, retroviral vector constructs are provided wherein the packaging signal that extends into, or overlaps with, retroviral gag/pol sequence is deleted or truncated. For example, in the representative case of MoMLV, the packaging signal is deleted or truncated downstream of the start of the gag/pol gene (nucleotide 621 of SEQ ID NO: 1). Within preferred embodiments of the invention, the packaging signal is terminated at nucleotide 570, 575, 580, 585, 590, 595, 600, 610, 615 or 617 of SEQ ID NO: 1.

Within other aspects of the invention, retroviral vector constructs are provided which include a packaging signal that extends beyond the start of the gag/pol gene (e.g., for MoMLV, beyond nucleotide 621 of SEQ ID NO: 1). When such retroviral vector constructs are utilized, it is preferable to utilize packaging cell lines for the production of recombinant viral particles wherein the 5' terminal end of the gag/pol gene in a gag/pol expression cassette has been modified to contain condons which are degenerate for gag. Such gag/pol expression cassettes are described in more detail below in section 2, and in Example 3.

Within certain embodiments, the packaging signal that extends beyond the start of the gag/pol gene was modified in order to contain one, two or more stop codons within the gag/pol reading frame. Most preferably, one of the stop codons eliminates the start site and/or has two or three base pair substitutions. One representative example of such modifications is provided below in Example 9.

Within other aspects of the present invention, retroviral vector constructs are provided comprising a 5' LTR, a tRNA binding site, a packaging signal, an origin of second strand DNA synthesis and a 3' LTR, wherein the retrovector plasmid construct does not contain a retroviral nucleic acid sequence upstream of the 5' LTR. As utilized within the context of the present invention, the phrase "does not contain a retroviral nucleic acid sequence upstream of the 5' LTR" should be understood to mean that the retrovector plasmid construct contains less than 20, preferably less than 15, more preferably less than 10, and most preferably less than 8 consecutive nucleotides which are found in a retrovirus, and more specifically, in a retrovirus which is homologous to the retroviral vector construct, upstream of and/or contiguous with the 5' LTR. Within preferred embodiments, the retrovector plasmid constructs do not contain an env coding sequence (as discussed below) upstream of the 5' LTR. A particularly preferred embodiment of such retrovector plasmid constructs is set forth in more detail below in Example 1.

Within a further aspect of the present invention, retrovector plasmid constructs are provided comprising a 5' LTR, a tRNA binding site, a packaging signal, an origin of second strand DNA synthesis and 3' LTR, wherein the retrovector plasmid construct does not contain a retroviral packaging signal sequence downstream of the 3' LTR. As utilized herein, the term "packaging signal sequence" should be understood to mean a sequence sufficient to allow packaging of the RNA genome. A representative example of such a retroviral vector construct is set forth in more detail below in Example 1.

Within other aspects of the present invention, retrovector plasmid constructs are provided comprising a 5' LTR, a tRNA binding site, a packaging signal, an origin of second strand DNA synthesis and a 3' LTR, wherein the retrovector plasmid construct does not contain envelope sequences upstream of the 3' LTR. As utilized within this context, the term "envelope sequence" should be understood to mean envelope coding as well as flanking untranslated sequences. A representative example of such a retroviral vector construct is set forth in more detail below in Example 9.

2. Construction of gag/pol expression cassettes

As noted above, the present invention also provides a variety of gag/pol expression cassettes which, in combination with the retroviral vector constructs and env expression cassettes of the present invention, enable the construction of packaging cell lines and producer cell lines which preclude the formation of replication competent virus. Briefly, retroviral gag/pol genes contain a gag region which encodes a variety of structural proteins that make up the core matrix and nucleocapsid, and a pol region which contains genes which encode (1) a protease for the processing of gag/pol and env proteins, (2) a reverse transcriptase polymerase, (3) an RNase H, and (4) an integrase, which is necessary for integration of the retroviral provector into the host genome. Although retroviral gag/pol genes may be utilized to construct the gag/pol expression cassettes of the present invention, a variety of other non-retroviral (and non-viral) genes may also be utilized to construct the gag/pol expression cassette. For example, a gene which encodes retroviral RNase H may be replaced with genes which encode bacterial (e.g., *E. coli* or *Thermus thermophilus*) RNase H. Similarly, a retroviral integrase gene may be replaced by other genes with similar function (e.g., yeast retrotransposon TY3 integrase).

Within one aspect of the invention, gag/pol expression cassettes are provided comprising a promoter operably linked to a gag/pol gene, and a polyadenylation sequence, wherein the gag/pol gene has been modified to contain codons which are degenerate for gag. Briefly, as noted above, in wild-type retrovirus the extended packaging signal of the retrovirus overlaps with sequences which encode gag and pol. Thus, in order to eliminate the potential of crossover between the retroviral vector construct and the gag/pol expression cassette, as well as to eliminate the possiblity of co-encapsidation of the gag/pol expression cassette and replication competent virus or retroviral vector constructs, sequences of overlap should be eliminated. Within one embodiment of the invention, elimination of such overlap is accomplished by modifying the gag/pol gene (and more specifically, regions which overlap with the retroviral vector construct, such as the extended packaging signal) to contain codons that are degenerate (i.e., that "wobble") for gag. In particular, within preferred embodiments of the invention codons are selected which encode biologically active gag/pol protein (i.e., capable of producing a competent retroviral particle, in combination with an env expressing element, and a RNA genome), and which lack any packaging signal sequence, including in particular, extended packaging signal sequence. As utilized herein, the phrase "lacks any retroviral packaging signal sequence" should be understood to mean that the gag/pol expression cassette contains less than 20, preferably less than 15, more preferably less than 10, and most preferably less than 8 consecutive nucleotides which are identical to a sequence found in a retroviral packaging signal (e.g., in the case of MoMLV, extending up and through the Xho I site at approximately nucleotide number 1561). A particularly preferred example of such modified codons which are degenerate for gag is shown in FIG. 10, and in Example 3, although the present invention should not be so limited. In particular, within other embodiments, at least 25, 50, 75, 100, 125 or 135 gag codons are modified or "wobbled" from the native gag sequence within the gag/pol expression cassettes of the present invention.

In addition to eliminating overlap between the retroviral vector construct and the gag/pol gene, it is also preferable to eliminate any potential overlap between the gag/pol gene and the env gene in order to prohibit the possibility of homologous recombination. This may be accomplished in at least two principal ways: (1) by deleting a portion of the gag/pol gene which encodes the integrase protein, and in particular, that portion of the gene which encodes the integrase protein which overlaps with the env coding sequence, or (2) by selecting codons which are degenerate for integrase and/or env.

Thus, within one aspect of the present invention gag/pol expression cassettes are provided comprising a promoter operably linked to a gag/pol gene, and a polyadenylation sequence or signal, wherein a 3' terminal end of the gene has been deleted without effecting biological activity of the integrase. (The biological activity of integrase may be readily determined by detection of an integration event, either by DNA analysis or by expression of a transduced gene; see Roth et al., *J. Vir.* 65(4):2141–2145, 1991.) As an example, in the Murine Leukemia Virus MoMLV (SEQ ID. NO. 1), the gag/pol gene is encoded by nucleotides 621 through 5834. Within this sequence, the protein integrase is encoded by nucleotides 4610 through nucleotide 5834. A portion of the gag/pol sequence which encodes integrase also encodes env (which begins at nucleotide 5776). Thus, within one embodiment of the invention, the 3' terminal end of the gag/pol gene is deleted or truncated in order to prevent crossover with the env gene, without effecting the biological activity of the integrase. Within other preferred embodiments, the gag/pol gene is deleted at any nucleotide downstream (3') from the beginning of the integrase coding sequence, and preferably prior to the start of the env gene sequence. Within one embodiment, the sequence encoding gag/pol is a MoMLV sequence, and the gag/pol gene is deleted at any nucleotide between nucleotides 4610 and 5776 (of SEQ. I.D. No. 1), including for example, at nucleotides 5775, 5770, 5765, 5760, 5755, 5750.

Within other embodiments of the invention, the gag/pol expression cassette contains sequences encoding gag/pol (and including integrase), while lacking any sequence found in an env gene. The phrase "lacking any sequence found in an env gene" should be understood to mean that the gag/pol expression cassette does not contain at least 20, preferably at least 15, more preferably at least 10, and most preferably less than 8 consecutive nucleotides which are identical to an env sequence, and preferably which are found in an env expression cassette which will be utilized along with the gag/pol expression cassette to form a packaging cell. Such expression cassettes may be readily prepared by selecting codons which are degenerate for integrase, and which do not encode biologically active env. (See *Morgenstern and Land, Nuc. Acids Res.* 18:3587–3596, 1990.)

Within other embodiments of the invention, the gag/pol expression cassette contains a heterologous promoter, and/or heterologous polyadenylation sequence. As utilized herein, "heterologous" promoters or polyadenylation sequences refers to promoters or polyadenylation sequences which are from a different source from which the gag/pol gene (and preferably the env gene and retroviral vector construct) is derived from. Representative examples of suitable promoters include the Cytomegalovirus Immediate Early ("CMV IE") promoter, the Herpes Simplex Virus Thymidine Kinase ("HSVTK") promoter, the Rous Sarcoma Virus ("RSV") promoter, the Adenovirus major-late promoter and the SV 40 promoter. Representative examples of suitable polyadenylation signals include the SV 40 late polyadenylation signal and the SV 40 early polyadenylation signal.

Within preferred aspects of the present invention, gag/pol expression cassettes such as those described above will not co-encapsidate along with a replication competent virus. One representative method for determination of co-encapsidation is set forth below in Example 8.

3. Construction of env expression cassettes

Within other aspects of the present invention, env expression cassettes are provided which, in combination with the gag/pol expression cassettes and retroviral vector constructs described above, preclude formation of replication competent virus by homologous recombination, as well as to confer a particular specificity of the resultant vector particle (e.g., amphotropic, ecotropic, xenotropic or polytropic; see FIG. 17, as well as the discussion above). Briefly, in a wild-type retrovirus the env gene encodes two principal proteins, the surface glycoprotein "SU" and the transmembrane protein "TM", which are translated as a polyprotein, and subsequently separated by proteolytic cleavage. Representative examples of the SU and TM proteins are the gp120 protein and gp41 protein in HIV, and the gp70 protein and p15e protein in MoMLV. In some retroviruses, a third protein designated the "R" peptide" of undetermined function, is also expressed from the env gene and separated from the polyprotein by proteolytic cleavage. In the Murine Leukemia Virus MoMLV, the R peptide is designated "p2".

A wide variety of env expression cassettes may be constructed given the disclosure provided herein, and utilized within the present invention to preclude homologous recombination. Within one aspect of the present invention, env expression cassettes are provided comprising a promoter operably linked to an env gene, wherein no more than 6, 8, 10, 15, or 20 consecutive retroviral nucleotides are included upstream (5') of and/or contiguous with said env gene. Within other aspects of the invention, env expression cassettes are provided comprising a promoter operably linked to an env gene, wherein the env expression cassette does not contain a consecutive sequence of greater than 20, preferably less than 15, more preferably less than 10, and most preferably less than 8 or 6 consecutive nucleotides which are found in a gag/pol gene, and in particular, in a gag/pol expression cassette that will be utilized along with the env expression cassette to create a packaging cell line.

Within another aspect of the present invention, env expression cassettes are provided comprising a promoter operably linked to an env gene, and a polyadenylation sequence, wherein a 3' terminal end of the env gene has been deleted without effecting the biological activity of env. As utilized herein, the phrase "biological activity of env" refers to the ability of envelope protein to be expressed on the surface of a virus or vector particle, and to allow for a successful infection of a host cell. One practical method for assessing biological activity is to transiently transfect the env expression cassette into a cell containing a previously determined functional gag/pol expression cassette, and a retroviral vector construct which expresses a selectable marker. Another method for assessing biological activity is to either stably transfect the env expression cassette together with a retroviral vector construct coding for a selectable marker into a cell containing a previously determined functional gag/pol expression cassette, or, transducing this gag/pol expressing cell in a transient and/or stable manner with a retroviral vector coding for the env gene and a selectable marker. A biologically functional env expression cassette will allow vector particles produced in that transfected cell, to transmit the selectable marker to a naive sensitive cell such that it becomes resistant to the marker drug selection. Within a preferred embodiment of the invention, the 3' terminal end of the env gene is deleted or truncated such that a complete R peptide is not produced by the expression cassette. In the representative example of MoMLV, sequence encoding the R peptide (which begins at nucleotide 7734) is deleted, truncated, or, for example, terminated by insertion of a stop codon at nucleotide 7740, 7745, 7747, 7750, 7755, 7760, 7765, 7770, 7775, 7780, or any nucleotide in between.

Within another aspect of the present invention, env expression cassettes are provided which contain a heterologous promoter, a heterologous leader sequence and/or heterologous polyadenylation sequence. As utilized herein, "heterologous" promoters, leaders or polyadenylation sequences refers to sequences which are from a different source from which the gag/pol gene (and preferably the env gene and retroviral vector construct) is derived from. Representative examples of suitable promoters include the CMV IE promoter, the HSVTK promoter, the RSV promoter, the Adenovirus major-late promoter and the SV 40 promoters. Representative examples of suitable polyadenylation signals include the SV 40 late polyadenylation signal and the SV 40 early polyadenylation signal, and the bovine growth hormone termination/polyadenylation sequence. Preferably any such termination/polyadenylation sequence will not have any 10 bp stretch which has more than 80% homology to a retroviral construct.

Envelope expression cassettes that contain no MoMLV noncoding sequences can also be created. For example, analogous to the 3' end modifications described in example 12, noncoding bases on the 5' of envelope prior to the start AUG codon can be deleted as described in Example 4. another method of 5' end modification is to substitute the 5' untranslated RNA leader of MoMLV envelope with an alternate leader. The 5' untranslated RNA sequence can be a leader from another protein or an entirely synthetic leader. The leader may also contain one or more introns. The only requirements for the leader are that it contains a Kozak sequence sufficient for efficient translation of the amphotropic envelope. Representative leader sequences may also include untranslated RNA leaders for envelope proteins from other viruses. Examples of these include Vesicular Stomatitis Virus —G protein (VSV-g), Herpes Simplex Virus(HSV) gB protein, or HSV-gD protein. The 5' untranslated leader sequence is inserted so that it spans the sequence between the eucaryotic promoter start site and the amphotropic envelope start codon.

HETEROLOGOUS SEQUENCES

As noted above, the retroviral vector constructs, gag/pol expression cassettes, and env expression cassettes of the present invention may contain (and express) one or more heterologous sequences. As utilized within the context of the present invention, it should be understood that the heterologous sequence need not code for a particular protein, but may be merely included in order to improve efficiency of viral particle production. In this regard, heterologous sequences of at least 1 kb or greater are particularly preferred.

A wide variety of heterologous sequences may be utilized within the context of the present invention, including for example, cytotoxic genes, antisense sequences, sequences which encode gene products that activate a compound with little or no cytotoxicity (i.e., a "prodrug") into a toxic product, sequences which encode immunogenic portions of disease-associated antigens and sequences which encode immune accessory molecules. Representative examples of cytotoxic genes include the genes which encode proteins such as ricin (Lamb et al., *Eur. J. Biochem.* 148:265–270, 1985), abrin (Wood et al., *Eur. J. Biochem.* 198:723–732, 1991; Evensen, et al., *J. of Biol. Chem.* 266:6848–6852, 1991: Collins et al., *J. of Biol. Chem.* 265:8665–8669, 1990; Chen et al., *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez & Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), antiviral protein (Barbieri et al., *Biochem. J.* 203:55–59, 1982; Irvin et al., *Arch. Biochem. & Biophys.* 200:418–425, 1980; Irvin, *Arch. Biochem. & Biophys.* 169:522–528, 1975), tritin, Shigella toxin (Calderwood et al., *PNAS* 84:4364–4368, 1987; Jackson et al., *Microb. Path.* 2:147–153, 1987), and Pseudomonas exotoxin A (Carroll and Collier, *J. Biol. Chem.* 262:8707–8711, 1987).

Within further embodiments of the invention, antisense RNA may be utilized as a cytotoxic gene in order to induce a potent Class I restricted response. Briefly, in addition to binding RNA and thereby preventing translation of a specific mRNA, high levels of specific antisense sequences may be utilized to induce the increased expression of interferons (including gamma-interferon), due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

Within other embodiments of the invention, antisense sequences are provided which inhibit, for example, tumor cell growth, viral replication, or a genetic disease by preventing the cellular synthesis of critical proteins needed for cell growth. Examples of such antisense sequences include antisense thymidine kinase, antisense dihydrofolate reductase (Maher and Dolnick, *Arch. Biochem. & Biophys.* 253:214–220, 1987; Bzik et al., *PNAS* 84:8360–8364, 1987), antisense HER2 (Coussens et al., *Science* 230:1132–1139, 1985), antisense ABL (Fainstein, et al., *Oncogene* 4:1477–1481, 1989), antisense Myc (Stanton et al., *Nature* 310:423–425, 1984) and antisense ras, as well as antisense sequences which block any of the enzymes in the nucleotide biosynthetic pathway.

Within other aspects of the invention, retroviral vector constructs, gag/pol expression cassettes and env expression cassettes are provided which direct the expression of a gene product that activates a compound with little or no cytotoxicity (i.e., a "prodrug") into a toxic product. Representative examples of such gene products include varicella zoster virus thymidine kinase (VZVTK), herpes simplex virus thymidine kinase (HSVTK) (Field et al., *J. Gen. Virol.* 49:115–124, 1980; Munir et al., *Protein Engineering* 7(1): 83–89, 1994; Black and Loeb, *Biochem* 32(43): 11618–11626, 1993), and *E. coli.* guanine phosphoribosyl transferase (see U.S. patent application Ser. No. 08/155,944, entitled "Compositions and Methods for Utilizing Conditionally Lethal Genes," filed Nov. 18, 1993, abandoned; see also WO 93/10218 entitled "Vectors Including Foreign Genes and Negative Selection Markers", WO 93/01281 entitled "Cytosine Deaminase Negative Selection System for Gene Transfer Techniques and Therapies", WO 93/08843 entitled "Trapped Cells and Use Thereof as a Drug", WO 93/08844 entitled "Transformant Cells for the Prophylaxis or Treatment of Diseases Caused by Viruses, Particularly Pathogenic Retroviruses", and WO 90/07936 entitled "Recombinant Therapies for Infection and Hyperproliferative Disorders.") Within preferred embodiments of the invention, the retroviral vector constructs direct the expression of a gene product that activates a compound with little or no cytotoxicity into a toxic product in the presence of a pathogenic agent, thereby affecting localized therapy to the pathogenic agent (see WO 94/13304).

Within one embodiment of the invention, retroviral vector constructs are provided which direct the expression of a HSVTK gene downstream, and under the transcriptional control of an HIV promoter (which is known to be transcriptionally silent except when activated by HIV tat protein). Briefly, expression of the tat gene product in human cells infected with HIV and carrying the vector construct causes increased production of HSVTK. The cells (either in vitro or in vivo) are then exposed to a drug such as ganciclovir, acyclovir or its analogues (FIAU, FIAC, DHPG). Such drugs are known to be phosphorylated by HSVTK (but not by cellular thymidine kinase) to their corresponding active nucleotide triphosphate forms. Acyclovir and FIAU triphosphates inhibit cellular polymerases in general, leading to the specific destruction of cells expressing HSVTK in transgenic mice (see Borrelli et al., *Proc. Natl. Acad. Sci. USA* 85:7572, 1988). Those cells containing the recombinant vector and expressing HIV tat protein are selectively killed by the presence of a specific dose of these drugs.

Within further aspects of the present invention, retroviral vector constructs, gag/pol expression cassettes and env expression cassettes of the present invention may also direct the expression of one or more sequences which encode immunogenic portions of disease-associated antigens. As utilized within the context of the present invention, antigens are deemed to be "disease-associated" if they are either associated with rendering a cell (or organism) diseased, or are associated with the disease-state in general but are not required or essential for rendering the cell diseased. In addition, antigens are considered to be "immunogenic" if they are capable, under appropriate conditions, of causing an immune response (either cell-mediated or humoral). Immunogenic "portions" may be of variable size, but are preferably at least 9 amino acids long, and may include the entire antigen.

A wide variety of "disease-associated" antigens are contemplated within the scope of the present invention, including for example immunogenic, non-tumorigenic forms of altered cellular components which are normally associated with tumor cells (see WO 93/10814). Representative examples of altered cellular components which are normally associated with tumor cells include ras* (wherein "*" is understood to refer to antigens which have been altered to be non-tumorigenic), p53*, Rb*, altered protein encoded by Wilms' tumor gene, ubiquitin*, mucin, protein encoded by the DCC. APC, and MCC genes, as well as receptors or receptor-like structures such as neu, thyroid hormone receptor, Platelet Derived Growth Factor ("PDGF") receptor, insulin receptor. Epidermal Growth Factor ("EGF") receptor, and the Colony Stimulating Factor ("CSF") receptor.

"Disease-associated" antigens should also be understood to include all or portions of various eukaryotic, prokaryotic or viral pathogens. Representative examples of viral pathogens include the Hepatitis B Virus ("HBV") and Hepatitis C Virus ("HCV"; see WO 93/15207), Human Papiloma Virus ("HPV"; see WO 92/05248; WO 90/10459; EPO 133,123), Epstein-Barr Virus ("EBV"; see EPO 173,254; JP 1,128, 788; and U.S. Pat. Nos. 4,939,088 and 5,173,414), Feline Leukemia Virus ("FeLV"; see WO 93/09070; EPO 377,842; WO 90/08832; WO 93/09238), Feline Immunodeficiency Virus ("FIV"; U.S. Pat. No. 5,037,753; WO 92/15684; WO 90/13573; and JP 4,126,085), HTLV I and II, and Human Immunodeficiency Virus ("HIV"; see WO 93/02805).

Within other aspects of the present invention, the retroviral vector constructs, gag/pol expression cassettes and env expression cassettes described above may also direct the expression of one or more immune accessory molecules. As utilized herein, the phrase "immune accessory molecules" refers to molecules which can either increase or decrease the recognition, presentation or activation of an immune response (either cell-mediated or humoral). Representative examples of immune accessory molecules include a interferon, b interferon, IL-1, IL-2, IL-3, IL-4, IL-5, IL-6, IL-7 (U.S. Pat. No. 4,965,195), IL-8, IL-9, IL-10, IL-11, IL-12 (Wolf et al., *J. Immun.* 46:3074, 1991; Gubler et al., *PNAS* 88:4143, 1991; WO 90/05147; EPO 433,827), IL-13 (WO 94/04680), IL-14, IL-15, GM-CSF, M-CSF-1, G-CSF, CD3 (Krissanen et al., *Immunogenetics* 26:258–266, 1987), CD8, ICAM-1 (Simmons et al., *Nature* 331:624–627, 1988), ICAM-2 (Singer, *Science* 255:1671, 1992), b-microglobulin (Parnes et al., *PNAS* 78:2253–2257, 1981), LFA-1 (Altmann et al., *Nature* 338: 521, 1989), LFA3 (Wallner et al., *J. Exp. Med.* 166(4):923–932, 1987), HLA Class I, HLA Class II molecules B7 (Freeman et al., *J. Immun.* 143:2714, 1989), and B7-2. Within a preferred embodiment, the heterologous gene encodes gamma-interferon.

Within preferred aspects of the present invention, the retroviral vector constructs described herein may direct the expression of more than one heterologous sequence. Such multiple sequences may be controlled either by a single promoter, or preferably, by additional secondary promoters (e.g., Internal Ribosome Binding Sites or "IRBS" also known as Internal Ribosome Entry Sites or "IRES"). Within preferred embodiments of the invention, retroviral vector constructs direct the expression of heterologous sequences which act synergistically. For example, within one embodiment retroviral vector constructs are provided which direct the expression of a molecule such as IL-15, IL-12, IL-2, gamma interferon, or other molecule which acts to increase cell-mediated presentation in the $T_H1$ pathway, along with an immunogenic portion of a disease-associated antigen. In such embodiments, immune presentation and processing of the disease-associated antigen will be increased due to the presence of the immune accessory molecule.

Within other aspects of the invention, retroviral vector constructs are provided which direct the expression of one or more heterologous sequences which encode "replacement" genes. As utilized herein, it should be understood that the term "replacement genes" refers to a nucleic acid molecule which encodes a therapeutic protein that is capable of preventing, inhibiting, stabilizing or reversing an inherited or noninherited genetic defect. Representative examples of such genetic defects include disorders in metabolism, immune regulation, hormonal regulation, and enzymatic or membrane associated structural function. Representation examples of diseases caused by such defects include Cystic Fibrosis ("CF", see Dorin et al., *Nature* 326:614,), Parkinson's Disease, Adenosine Deaminase deficiency ("ADA"; Hahma et al., *J. Bact.* 173:3663–3672, 1991), b-globin disorders, Hemophilia A & B (Factor VIII-deficiencies; see Wood et al., *Nature* 312:330, 1984), Gaucher disease, diabetes, forms of gouty arthritis and Lesch-Nylan disease (due to "HPRT" deficiencies; see Jolly et al., *PNAS* 80:477–481, 1983) and Familial Hypercholesterolemia (LDL Receptor mutations; see Yamamoto et al., *Cell* 39:27–38, 1984).

Sequences which encode the above-described heterologous genes may be readily obtained from a variety of sources. For example, plasmids which contain sequences that encode immune accessory molecules may be obtained from a depository such as the American Type Culture Collection (ATCC, Rockville, Md.), or from commercial sources such as British Bio-Technology Limited (Cowley, Oxford England). Representative sources sequences which encode the above-noted immune accessory molecules include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No. 67024 (which contains a sequence which encodes Interleukin-1), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6). It will be evident to one of skill in the art that one may utilize either the entire sequence of the protein, or an appropriate portion thereof which encodes the biologically active portion of the protein.

Alternatively, known cDNA sequences which encode cytotoxic genes or other heterologous genes may be obtained from cells which express or contain such sequences. Briefly, within one embodiment mRNA from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159. See also PCR Technology: Principles and Applications for DNA Amplification, Erlich (ed.), Stockton Press, 1989 all of which are incorporated by reference herein in their entirety) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Sequences which encode the above-described genes may also be synthesized, for example, on an Applied Biosystems Inc. DNA synthesizer (e.g., ABI DNA synthesizer model 392 (Foster City, Calif.).

PREPARATION OF RETROVIRAL PACKAGING CELL LINES, AND GENERATION OF RECOMBINANT VIRAL PARTICLES

As noted above, the gag/pol expression cassettes and env expression cassettes of the present invention may be used to generate transduction competent retroviral vector particles by introducing them into an appropriate parent cell line in order to create a packaging cell line, followed by introduction of a retroviral vector construct, in order to create a producer cell line (see WO 92/05266). Such packaging cell lines, upon introduction of an N2-type vector construct (Armentano et al., *J. of Vir.* 61(5):1647–1650, 1987) produce a titer of greater than $10^5$ cfu/ml, and preferably greater than 10-fold, 20-fold, 50-fold, or 100-fold higher titer than similar transduced PA317 cells (Miller and Buttimore, *Mol. and Cell. Biol.* 6(8):2895–2902, 1986).

Within one aspect of the present invention, methods for creating packaging cell lines are provided, comprising the steps of (a) introducing a gag/pol expression cassette according into an animal cell, (b) selecting a cell containing a gag/pol expression cassette which expresses high levels of gag/pol, (c) introducing an env expression cassette into the selected cell, and (d) selecting a cell which expresses high levels of env, and thereby creating the packaging cell. Within other aspects of the present invention, methods for creating packaging cell lines are provided comprising the steps of (a) introducing an env expression cassette into an animal cell (b) selecting a cell which expressed high levels of env, (c) introducing a gag/pol expression cassette into the selected cell, and (D) selecting a cell containing a gag/pol expression cassette which expresses high levels of gag/pol, and thereby creating the packaging cell. As utilized herein, it should be understood that "high" levels of gag/pol or env refers to packaging cells which produce at least z times greater gag/pol or env protein than PA317 cells, wherein z is selected from the group consisting of 1, 2, 3, 4, 5, 6, 7, 8, 9 or 10.

A wide variety of animal cells may be utilized to prepare the packaging cells of the present invention, including for example cells obtained from vertebrates, warm-blooded animals, or, mammals such as human, feline, goat, bovine, sheep, caprine, macaque, dog, rat and mouse cells. Particularly preferred cell lines for use in the preparation of packaging cell lines of present invention are those that lack genomic sequences which are homologous to the retroviral vector construct, gag/pol expression cassette and env expression cassette to be utilized. Methods for determining homology may be readily accomplished by, for example, hybridization analysis (see *Martini et al., PNAS* 78:4892–4896, 1981; see also WO 92/05266).

Expression cassettes of the present invention may be introduced into cells by numerous techniques, including for example, transfection by various physical methods, such as electroporation, DEAE dextran, lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991), liposomes of several types (see e.g., Wang et al., *PNAS* 84:7851–7855, 1987); CaPO$_4$ (Dubensky et al., *PNAS* 81:7529–7533, 1984), DNA ligand (Wu et al, *J. of Biol. Chem.* 264:16985–16987, 1989), administration of nucleic acids alone (WO 90/11092), or administration of DNA linked to killed adenovirus (Curiel et al., *Hum. Gene Ther.* 3:147–154, 1992).

Producer cell lines (also called vector-producing lines or "VCLs") may then be readily prepared by introducing a retroviral vector construct into a packaging cell line via transfection as described above, or, via transduction. Within preferred embodiments of the invention, producer cell lines are provided comprising a gag/pol expression cassette, an env expression cassette, and a retroviral vector construct wherein the gag/pol expression cassette, env expression cassette and retroviral vector construct lack a consecutive sequence of greater than 20, preferably 15, more preferably 10, and most preferably 10 or 8 nucleotides in common.

PHARMACEUTICAL COMPOSITIONS

Within another aspect of the invention, pharmaceutical compositions are provided, comprising a recombinant viral particle as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for topical administration, injection, or oral, nasal, vaginal, sub-lingual, inhalant or rectal administration.

Pharmaceutically acceptable carriers or diluents are non-toxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a retroviral vector construct or recombinant viral particle in 1 mg/ml HSA, 18.75 mM Tris, pH 7.2, 37.5 mM NaCl and 40.0 mg/ml lactose. In this case, since the recombinant vector represents approximately 1 mg of material, it may be less than 1% of high molecular weight material, and less than 1/100,000 of the total material (including water). This composition is stable at −70° C. for at least six months.

Pharmaceutical compositions of the present invention may also additionally include factors which stimulate cell division, and hence, uptake and Melanocyte Stimulating Hormone (MSH), for melanomas or epidermal growth factor for breast or other epithelial carcinomas.

Particularly preferred methods and compositions for preserving recombinant viruses are described in U.S. applications entitled "Methods for Preserving Recombinant Viruses" (see WO 94/11414).

METHODS OF ADMINISTRATION

Within other aspects of the present invention, methods are provided for inhibiting or destroying pathogenic agents in a warm-blooded animal, comprising administering to a warm-blooded animal a recombinant viral particle as described above, such that the pathogenic agent is inhibited or destroyed. Within various embodiments of the invention, recombinant viral particles may be administered in vivo, or ex vivo. Representative routes for in vivo administration include intradermally ("i.d."), intracranially ("i.e."), intraperitoneally ("i.p."), intrathecally ("i.t."), intravenously ("i.v."), subcutaneously ("s.c."), intramuscularly ("i.m.") or even directly into a tumor.

Alternatively, the cytotoxic genes, antisense sequences, gene products, retroviral vector constructs or viral particles of the present invention may also be administered to a warm-blooded animal by a variety of other methods. Representative examples include transfection by various physical methods, such as lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991); liposomes of several types (see e.g., Wang et al., *PNAS* 84:7851–7855, 1987); CaPO$_4$ (Dubensky et al., *PNAS* 81:7529–7533, 1984); DNA ligand (Wu et al, *J. of Biol. Chem.* 264:16985–16987, 1989); administration of nucleic acids alone (WO 90/11092); or administration of DNA linked to killed adenovirus (Curiel et al., *Hum. Gene Ther.* 3:147–154, 1992).

Within a preferred aspect of the present invention, retroviral particles (or retroviral vector constructs alone) may be utilized in order to directly treat pathogenic agents such as a tumor. Within preferred embodiments, the retroviral particles or retroviral vector constructs described above may be directly administered to a tumor, for example, by direct injection into several different locations within the body of tumor. Alternatively, arteries which serve a tumor may be identified, and the vector injected into such an artery, in order to deliver the vector directly into the tumor. Within another embodiment, a tumor which has a necrotic center may be aspirated, and the vector injected directly into the now empty center of the tumor. Within yet another embodiment, the retroviral vector construct may be directly administered to the surface of the tumor, for example, by application of a topical pharmaceutical composition containing the retroviral vector construct, or preferably, a recombinant retroviral particle.

Within another aspect of the present invention, methods are provided for inhibiting the growth of a selected tumor in a warm-blooded animal, comprising the steps of (a) removing tumor cells associated with the selected tumor from a warm-blooded animal, (b) infecting the removed cells with a retroviral vector construct which directs the expression of at least one anti-tumor agent, and (c) delivering the infected cells to a warm-blooded animal, such that the growth of the selected tumor is inhibited by immune responses generated against the gene-modified tumor cell. Within the context of the present invention, "inhibiting the growth of a selected tumor" refers to either (1) the direct inhibition of tumor cell division, or (2) immune cell mediated tumor cell lysis, or both, which leads to a suppression in the net expansion of tumor cells. Inhibition of tumor growth by either of these two mechanisms may be readily determined by one of ordinary skill in the art based upon a number of well known methods (see U.S. Ser. No. 08/032,846, U.S. Pat. No. 5,662,896). Examples of compounds or molecules which act as anti-tumor agents include immune accessory molecules, cytotoxic genes, and antisense sequences as discussed above (see also U.S. Ser. No. 08/032,846, U.S. Pat. No. 5,662,896).

Cells may be removed from a variety of locations including, for example, from a selected tumor. In addition, within other embodiments of the invention, a vector construct may be inserted into non-tumorigenic cells, including for example, cells from the skin (dermal fibroblasts), or from the blood (e.g., peripheral blood leukocytes). If desired, particular fractions of cells such as a T cell subset or stem cells may also be specifically removed from the blood (see, for example, PCT WO 91/16116, an application entitled "Immunoselection Device and Method"). Vector constructs may then be contacted with the removed cells utilizing any of the above-described techniques, followed by the return of the cells to the warm blooded animal, preferably to or within the vicinity of a tumor. Within one embodiment of the present invention, subsequent to removing tumor cells from a warm-blooded animal, a single cell suspension may be generated by, for example, physical disruption or proteolytic digestion. In addition, division of the cells may be increased by addition of various factors such as melanocyte stimulating factor for melanomas or epidermal growth factor for breast carcinomas, in order to enhance uptake, genomic integration and expression of the recombinant viral vector.

Within the context of the present invention, it should be understood that the removed cells may not only be returned to the same animal, but may also be utilized to inhibit the growth of selected tumor cells in another, allogeneic, animal. In such a case it is generally preferable to have histocompatibility matched animals (although not always, see, e.g., Yamamoto et al., "Efficacy of Experimental FIV Vaccines," 1st International Conference of FIV Researchers, University of California at Davis, September 1991).

The above-described methods may additionally comprise the steps of depleting fibroblasts or other non-contaminating tumor cells subsequent to removing tumor cells from a warm-blooded animal, and/or the step of inactivating the cells, for example, by irradiation.

As noted above, within certain aspects of the present invention, several anti-tumor agents may be administered either concurrently or sequentially, in order to inhibit the growth of a selected tumor in accordance with the methods of the present invention. For example, within one embodiment of the invention, an anti-tumor agent such as g-IFN may be co-administered or sequentially administered to a warm blooded animal along with other anti-tumor agents such as IL-2, or IL-12, in order to inhibit or destroy a pathogenic agent. Such therapeutic compositions may be administered directly utilizing a single vector construct which directs the expression of at least two anti-tumor agents, or, within other embodiments, expressed from independent vector constructs. Alternatively, one anti-tumor agent (e.g., g-IFN) may be administered utilizing a vector construct, while other tumor agents (e.g., IL-2) are administered directly (e.g., as a pharmaceutical composition intravenously).

Within a particularly preferred embodiment, retroviral vector constructs which deliver and express both a g-IFN gene and another gene encoding IL-2, may be administered to the patient. In such constructs, one gene may be expressed from the retrovector LTR and the other may utilize an additional transcriptional promoter found between the LTRs, or may be expressed as a polycistronic mRNA, possibly utilizing an internal ribosome binding site. After in vivo gene transfer, the patient's immune system is activated due to the expression of g-IFN. Infiltration of the dying tumor with inflammatory cells, in turn, increases immune presentation and further improves the patient's immune response against the tumor.

Within other aspects of the present invention, methods are provided for generating an immune response against an immunogenic portion of an antigen, in order to prevent or treat a disease (see, e.g., U.S. Ser. Nos. 08/104,424, abandoned; 08/102,132, abandoned, 07/948,358, abandoned; 07/965,084, abandoned), for suppressing graft rejection. (see U.S. Ser. No. 08/116,827, abandoned), for suppressing an immune response (see U.S. Ser No. 08/116,828, abandoned), and for suppressing an autoimmune response (see U.S. Ser. No. 08/116,983, abandoned).

As will be understood by one of ordinary skill in the art given the disclosure provided herein, any of the retroviral vector constructs described herein may be delivered not only as a recombinant viral particle, but as direct nucleic acid vectors. Such vectors may be delivered utilizing any appropriate physical method of gene transfer, including for example, those which have been discussed above.

The following examples are offered by way of illustration, and not by way of limitation.

EXAMPLE 1

CONSTRUCTION OF RETROVECTOR BACKBONES

A. Preparation of a Retroviral vector construct That Does Not Contain an Extended Packaging Sequence (Y)

This example describes the construction of a retroviral vector construct using site-specific mutagenesis. Within this example, a MoMLV retroviral vector construct is prepared wherein the packaging signal "Y" of the retrovector is terminated at basepair 617 of SEQ ID NO: 1, thereby eliminating the ATG start of gag. Thus, no crossover can occur between the retroviral vector construct and the gag/pol expression cassette which is described below in Example 3.

Figure 2:
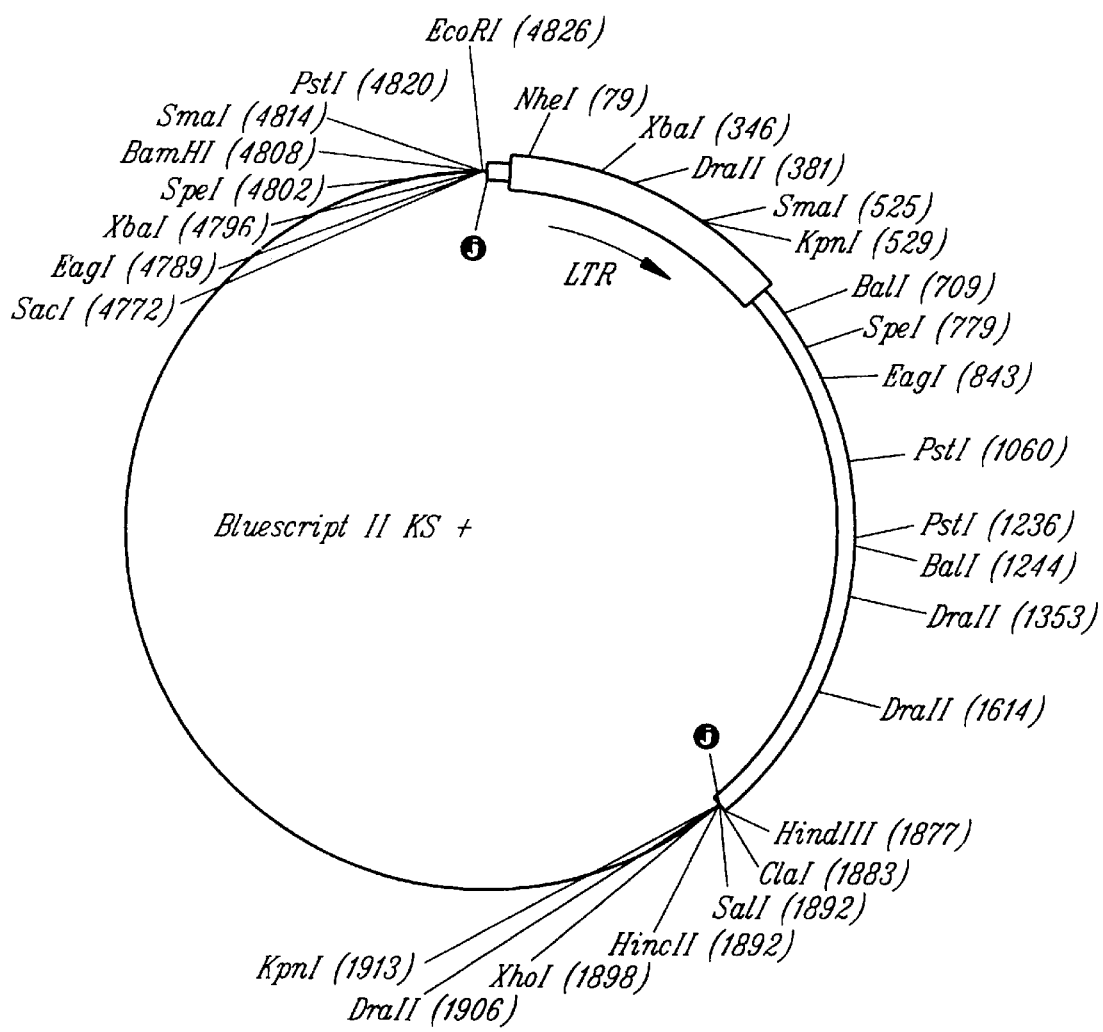
FIG. 2 is a schematic illustration of pKS2+Eco57I-LTR (−).

Briefly, pMLV-K (Miller, *J. Virol* 49:214–222, 1984—an infectious clone derived from pMLV-1 Shinnick et al., *Nature*, 293:543–548, 1981) is digested with Eco57I, and a 1.9 kb fragment is isolated. (Eco571 cuts upstream from the 3' LTR, thereby removing all env coding segments from the retroviral vector construct.) The fragment is then blunt ended with T4 polymerase (New England Biolabs), and all four deoxynucleotides, and cloned into the EcoRV site of phagemid pBluescript II KS+(Stratagene, San Diego, Calif.). This procedure yields two constructs, designated pKS2+Eco71I-LTR(+) (FIG. 1) and pKS2+Eco57I-LTR(−) (FIG. 2), which are screened by restriction analysis. When the (+) single stranded phagemid is generated, the sense sequence of MoMLV is isolated.

Figure 3:
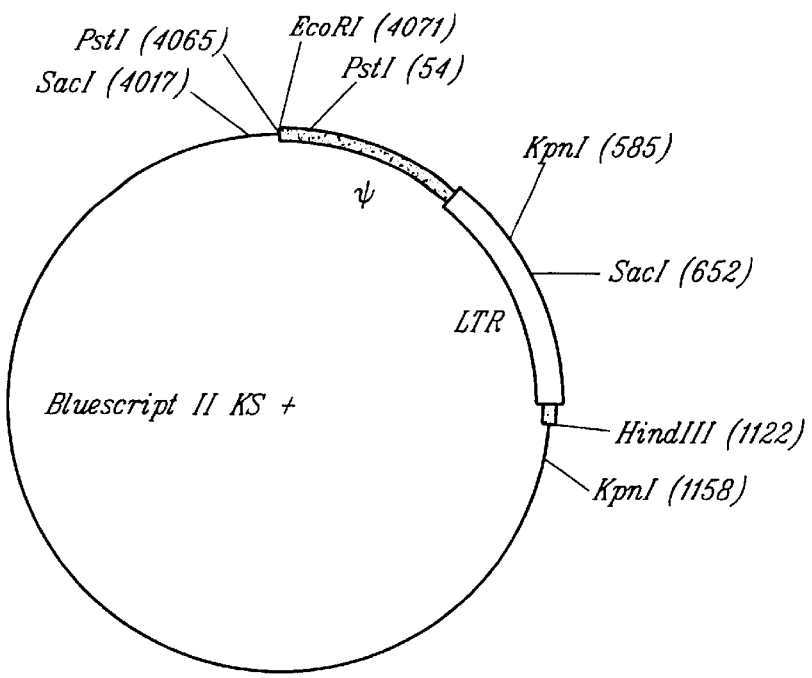
FIG. 3 is a schematic illustration of pKS2+LTR-EcoRI.

A new EcoRI site is then created in construct pKS2+ Eco57I-LTR(+) in order to remove the ATG start codon of gag. In particular, an EcoRI site is created using the single stranded mutagenesis method of Kunkle (*PNAS* 82:488, 1985). pKS2+Eco57I–LTR(+) is a pBluescript™II+ phagemid (Strategene, San Diego, Calif.) containing an Eco57I fragment from pMLV-K. It includes the MoMLV LTR and downstream sequence to basepair 1378. When single stranded phagemid is generated the sense sequence of MoMLV is isolated. The oligonucleotide 5'-GGT AAC AGT CTG GCC C<u>GA ATT C</u>TC AGA CAA ATA CAG (SEQ ID NO: 2), is created and used to generate an EcoRI site at basepairs 617–622. This construct is designated pKS2+LTR-EcoRI (FIG. 3).

B. Substitution of Nonsense Codons in the Extended Packaging Sequence (Y+)

This example describes modification of the extended packaging signal (Y+) by site-specific mutagenesis. In particular, the modification will substitute a stop codon, TAA, at the normal ATG start site of gag (position 621–623 of SEQ ID NO: 1), and an additional stop codon TAG at position 637–639 of SEQ ID NO: 1.

Briefly, an Eco57I—EcoRI fragment (MoMLV basepairs 7770 to approx. 1040) from pN2 (Amentano et al., J. Virol. 61:1647–1650, 1987) is first cloned into pBluescript II KS+ phagemid at the SacII and EcoRI sites (compatible). Single stranded phagemid containing antisense MoMLV sequence, is generated using helper phage M13K07 (Stratagene, San Diego, Calif.). The oligonucleotide 5'-CTG TAT TTG TCT GAG AAT <u>TAA</u> GGC <u>TAG</u> ACT GTT ACC AC (SEQ ID NO: 3) is synthesized, and utilize according to the method of Kunkle as described above, in order to modify the sequence within the Y region to encode stop codons at nucleotides 621–623 and 637–639.

C. Removal of Retroviral Packaging Sequence Downstream from the 3' LTR

Retroviral packaging sequence which is downstream from 3' LTR is deleted essentially as described below. Briefly, pKS2+Eco57I-LTR(−) (FIG. 2) is digested with BalI and HincII, and relegated excluding the BAlI to HincII DNA which contains the packaging region of MoMLV.

D. Construction of Vector Backbones

Constructs prepared in sections A and C above, or alternatively from sections B and C above, are combined with a plasmid vector as described below, in order to create a retrovector backbone containing all elements required in cis, and excluding all sequences of 8 nucleic acids or more contained in the retroviral portion of the gag-pol and env expression elements (see Examples 3 and 4).

Figure 4:
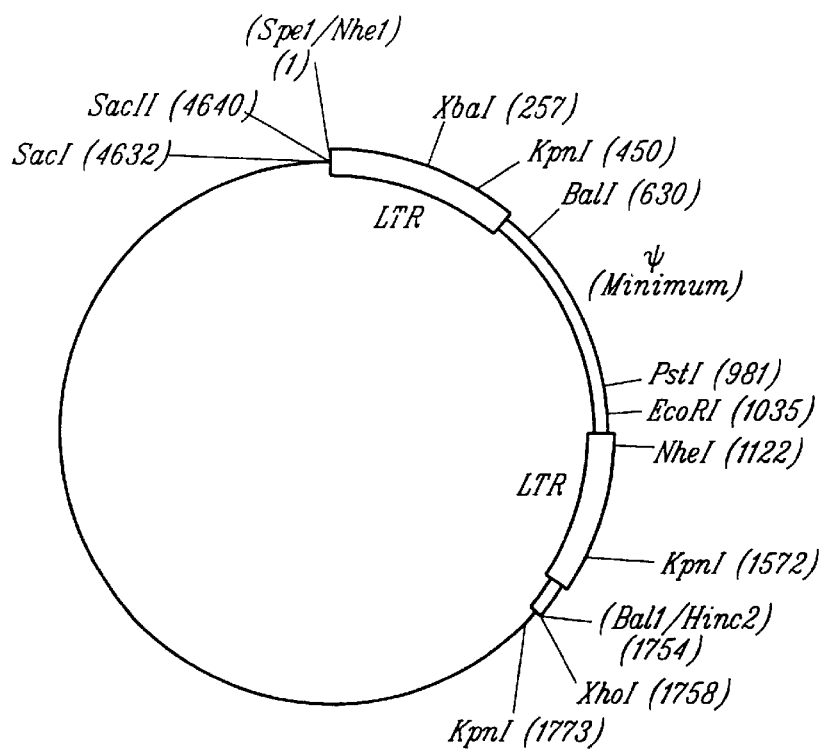
FIG. 4 is a schematic illustration of pR1.

1. Parts A and C are combined as follows: The product of A is digested with NheI and EcoRI, and a 1034 basepair fragment containing the LTR and minimal Y is isolated. The fragment is ligated into the product of part C at the unique (compatible) restriction sites SpeI and EcoRI. The resultant construct is designated pR1 (FIG. 4)

Figure 5:
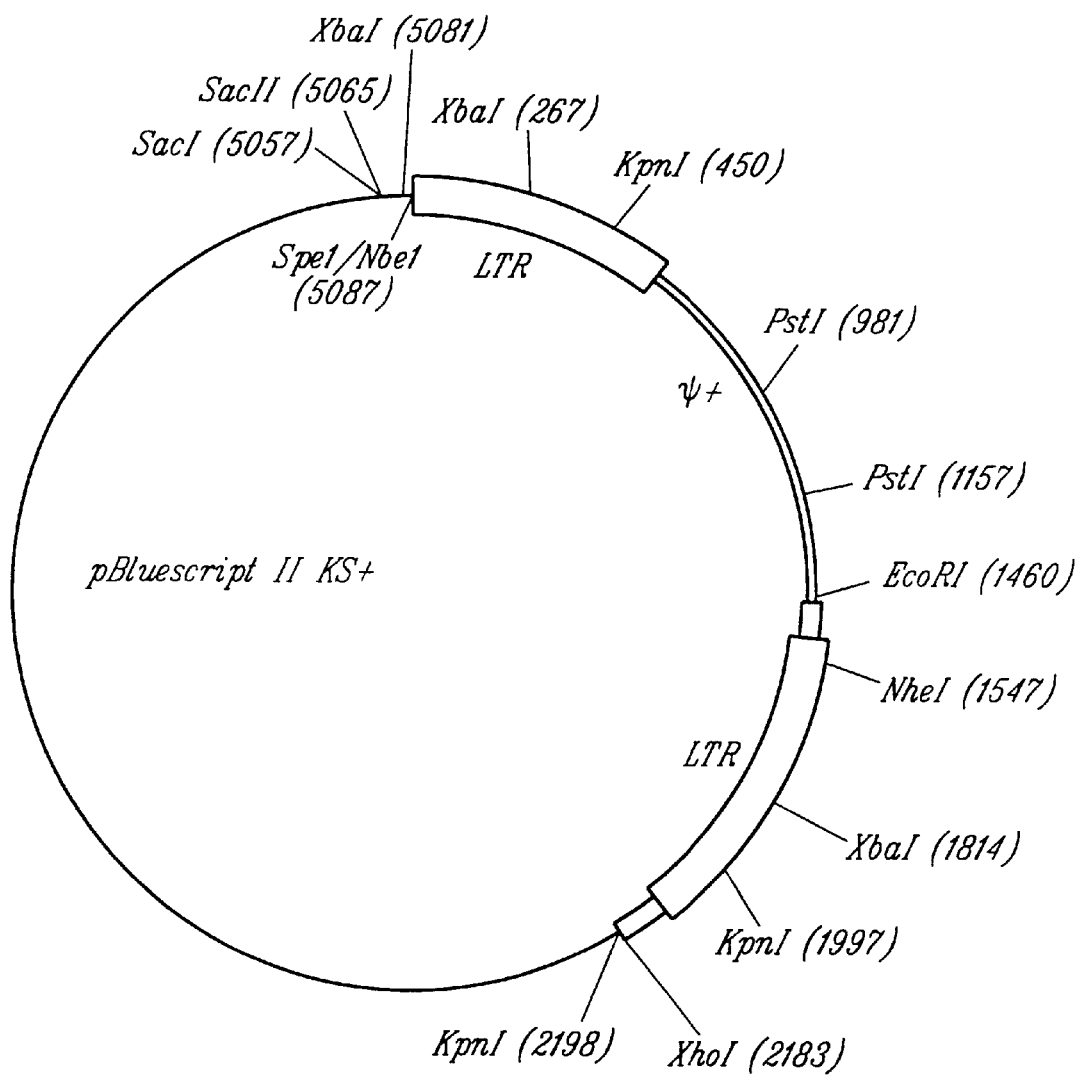
FIG. 5 is a schematic illustration of pR2.

2. Parts B and C are combined as follows: The product of B is digested with NheI and EcoRI and a 1456 basepair fragment containing the LTR and modified Y+ region is isolated. The fragment is ligated into the product of C at the unique (compatible) restriction sites SpeI and EcoRI. The resultant construct is designated pR2 (FIG. 5).

EXAMPLE 2

INSERTION OF A GENE OF INTEREST INTO pR1 and pR2

Figure 6:
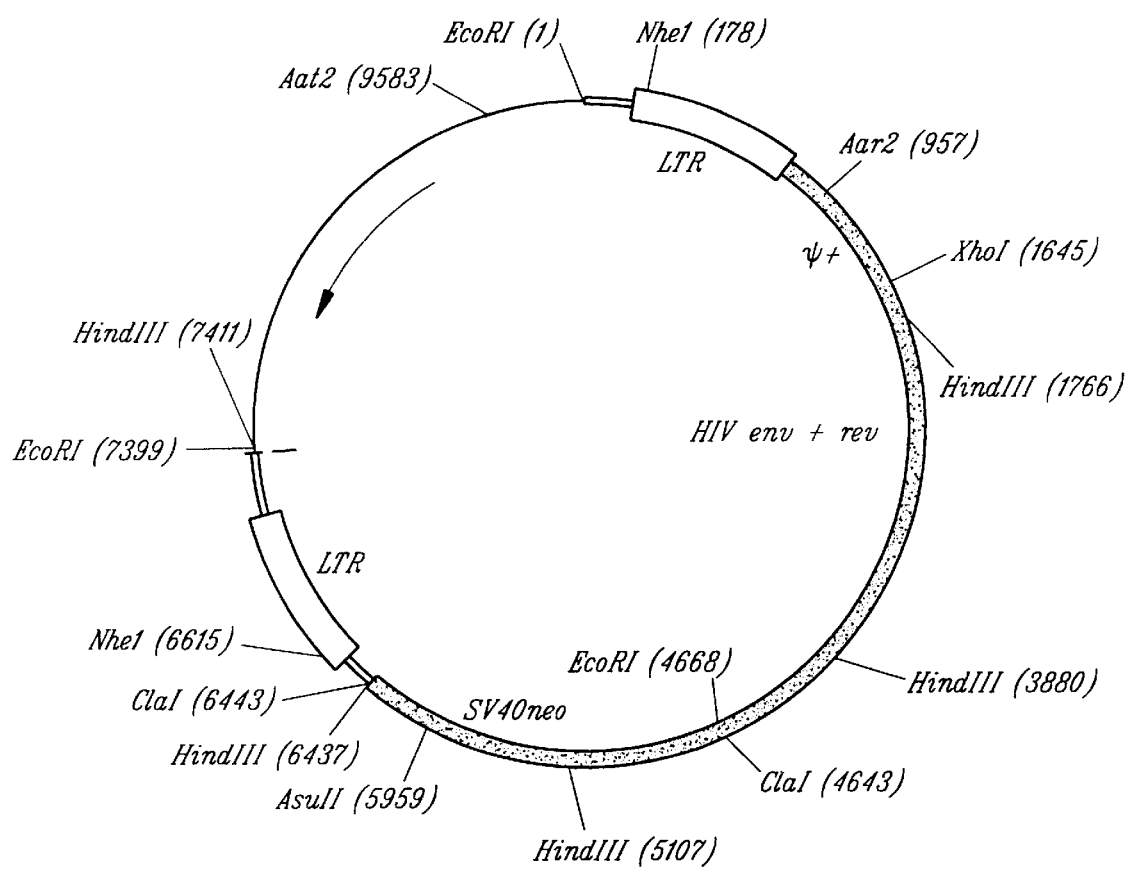
FIG. 6 is a schematic illustration of pKT1.
Figure 7:
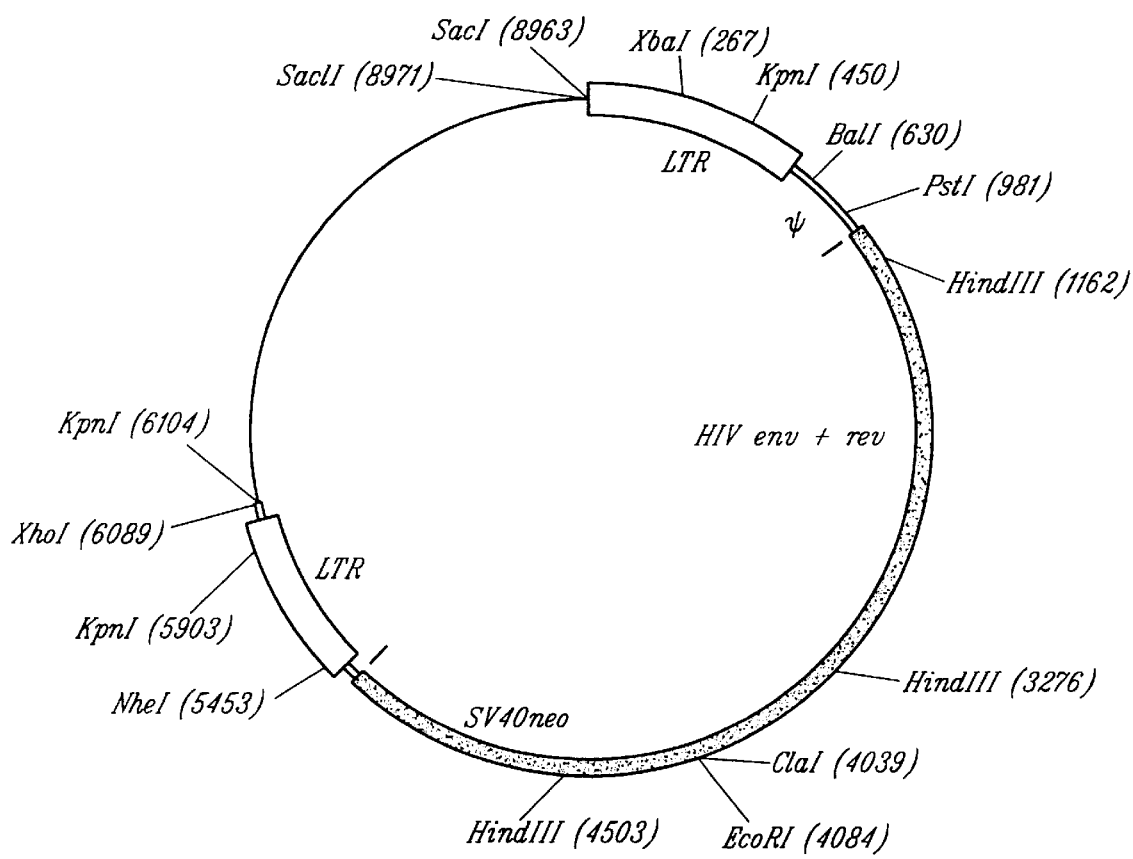
FIG. 7 is a schematic illustration of pRI-HIVenv.
Figure 8:
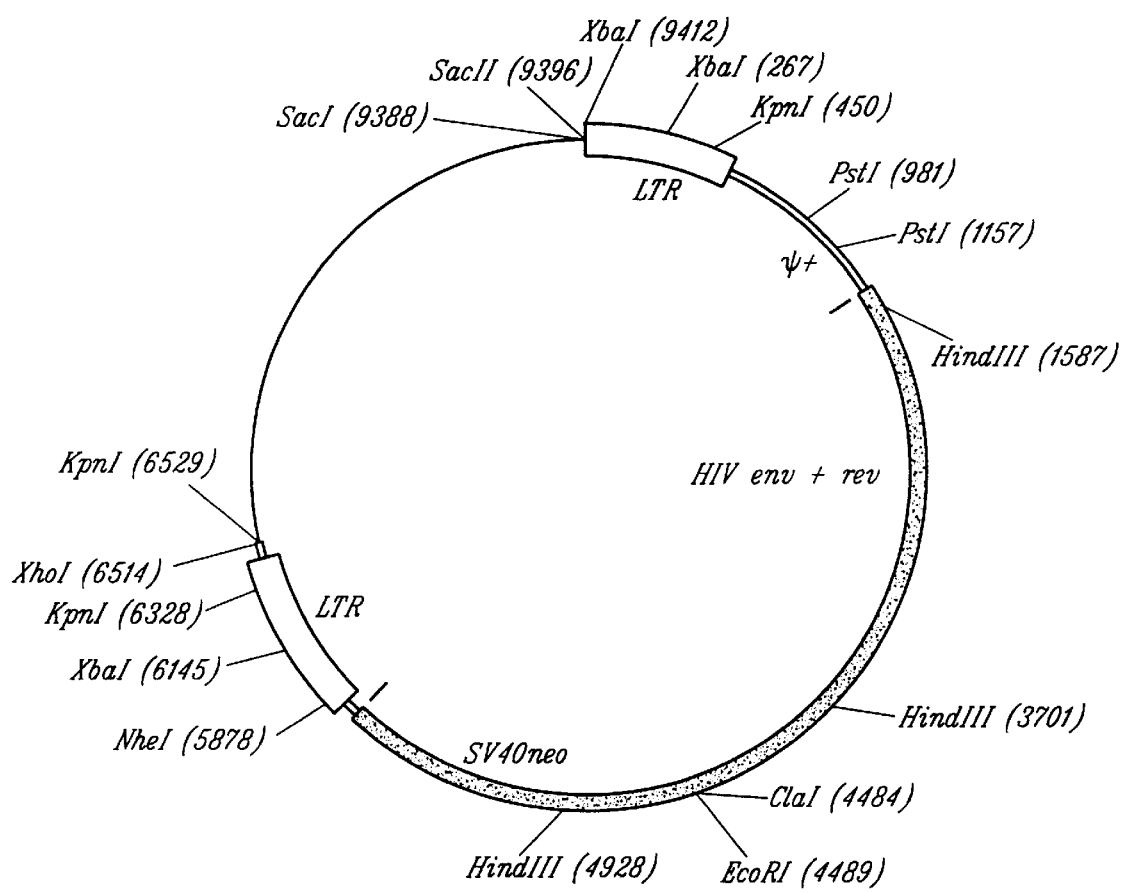
FIG. 8 is a schematic illustration of pR2-HIVenv.

This example describes the insertion of a gene of interest, gp120, gp41, and rev along with a selectable marker into either pR1 and pR2. Briefly, the sequence encoding gp120, gp41 and rev is taken from construct pKT1 (FIG. 6, see also Chada et al., J. Vir. 67:3409–3417, 1993); note that this vector is also referred to as N2IIIBenv. In particular, pKT1 is first digested at the unique AsuII site (position 5959). The ends are blunted, and an Xho I linker is ligated at that site. (New England Biolabs). The construct is then digested with Xho I, and a 4314 bp fragment containing HIV envelope (gp120 and gp41), rev, SV40 early promoter and G418 resistance genes is isolated.

pR1 and pR2 is digested at the unique Eco R1 restriction site, blunted, and Sal I linkers (New England Biolabs) are ligated in. The 4314 bp KT1 fragment is then ligated into pR1 and pR2 at the new Sal sites, and the correct orientation is determined (see FIGS. 7 and 8). In both of these constructs, (pR1-HIV env and pR2-HIV env) the HIV genes are expressed from the MLV LTR, and G418 resistance is expressed from the SV40 promoter.

EXAMPLE 3

CONSTRUCTION OF GAG-POL EXPRESSION CASSETTES

A. Construction of an Expression Cassette Backbone, pHCMU-PA

A vector is first created in order to form the backbone for both the gag/pol and env expression cassettes. Briefly, pBluescript SK-phagemid (Stratagene, San Diego, Calif.; GenBank accession number 52324; referred to as "SK-") is digested with SpeI and blunt ended with Klenow. A blunt end DraI fragment of SV40 (Fiers et al., "Complete nucleotide sequence of SV40 DNA" Nature 273:113–120, 1978) from DraI (bp 2366) to DraI (bp2729) is then inserted into SK—, and a construct isolated in which the SV40 late polyadenylation signal is oriented opposite to the LacZ gene of SK-. This construct is designated SK-SV40A.

Figure 11:
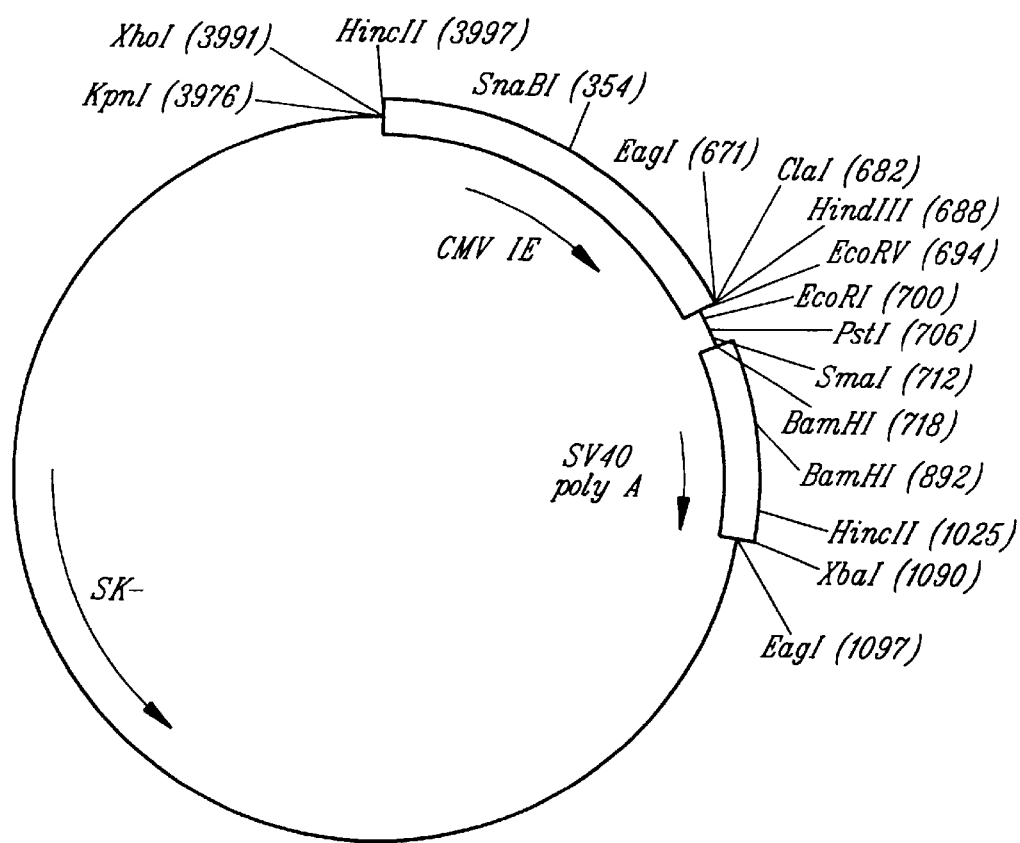
FIG. 11 is a schematic illustration of pHCMV-PA.

A Human Cytomegalovirus Major Immediate Early Promoter ("HCMV-IE"; Boshart et al., Cell 41:521–530, 1985) (HineII, bp 140, to EagI, bp814) is isolated after digestion with HincII and EagI, and the EagI site blunt ended. The 674 blunt ended fragment is ligated into SK-SV40A. The final construct, designated pHCMV-PA is then isolated (see FIG. 11). This construct contains the HCMV promoter oriented in opposite orientation to the LacZ gene, and upstream from the late polyadenylation signal of SV40.

B. Creation of New Codons for the 5' Gag

This example describes gag/pol expression cassettes that lack non-coding sequences upstream from the gag start, thereby reducing recombination potential between the gag-pol expression element and Y+ sequence of a retroviral vector construct, and inhibiting co-packaging of the gag-pol expression element along with the retrovector. In order to construct such an expression cassette, 448 bp of DNA is synthesized with the following features: 5' ATATATATAT ATCGAT(ClaI site) ACCATG(start codon, position 621) (SEQ ID NO: 4), followed by 410 bp encoding 136+ amino acid residues using alternative codons (see FIGS. 9 and 10), followed by GGCGCC(NarI site)AAACCTAAAC 3' (SEQ ID NO: 5).

Briefly, each of oligos 15 and 24 (set forth below in Table 1) are added to a PCR reaction tube such that the final concentration for each is 1 µM. Oligos 25 and 26 are added to the tube such that the final concentration for each is 3 µM. 1.2 µL of 2.5 mM stock deoxynucleotide triphosphates (dG, dA, dT, dC) are added to the tube. 5 µL of 10× PCR buffer (Perkin Elmer). Water is added to a final volume of 50 µL. Wax beads are added and melted over the aqueous layer at 55° C. and then cooled to 22° C. A top aqueous layer is added as follows: 5 µL 10× PCR buffer, 7.5 µL dimethylsulfoxide, 1.5 µL Tag polymerase (Perkin-Elmer) and 36 µL water. Forty cycles of PCR are then performed as follows 94_C, 30 seconds; 56_C, 30 seconds; and 72_C, 30 seconds. The PCR product is stored at −20_C until assembly of the gag/pol expression cassette.

TABLE 1

| SEQ. ID No. | Sequence |
|---|---|
| 15 | 5' ATA TAT ATA TAT CQA TAC CAT GGG GCA MC CGT GAC TAC CCC TCT GTC CCT GA C ACT GGC CCA A 3' |
| 16 | 5' TTG ATT ATG GGC AAT TCT TTC CAC GTC CTT CCA ATG GCC CAG TGT GAG GGA C 3' |
| 17 | 5' AGA ATT GCC CAT AAT CAA AGC GTG GAC GTC AAA AAA CGC AGG TGG GT G ACA TTT TGT AGC GCC GAG TGG CCC 3' |
| 18 | 5' MG TTC CAT CCC TAG GCC AGC CAA CAT TGA ATG TGG GCC ACT CGG CGC TAC A 3' |
| 19 | 5' GGC CTA GGG ATG GAA CTT TCA ATC GCG ATC TGA TTA CTC AAG TGA AA A TTA AAG TGT TCA GCC CCG GAC CCC 3' |
| 20 | 5' GT ACA ATA TAA GGA ACT TGA TCG GGA TGG CCG TGG GGT CCG GGG CTG AAC A 3' |
| 21 | 5' AGT TCC TTA TAT TGT CAC ATC GGA GGC TCT CGC TTT CGA TCC ACC ACC TTG GGT GAA ACC ATT CGT GCA TCC 3' |
| 22 | 5' AGG AGC GCT GGG TGG GAG GGG TGG AGG TGG TTT GGG ATG CAC GAA TGG TTT C 3' |
| 23 | 5' CTC CCA CCC AGC GCT CCT AGC CTG CCC TTG GAG CCC CCA CGA AGC ACA CCA CCC AGG AGC AGC TTG TAC CCT 3' |
| 24 | 5' GTT TAG GTT TGG CGC CGA GGC TGG GGG TCA GAG CAG GGT ACA AGQ TGC TCC T 3' |
| 25 | 5' ATA TAT ATA TAT CGA TAC C 3' |
| 26 | 5' GTT TAG GTT TGG CGC CGA GG 3' |

C. Creation of a New 3' End for Pol

Figure 12:
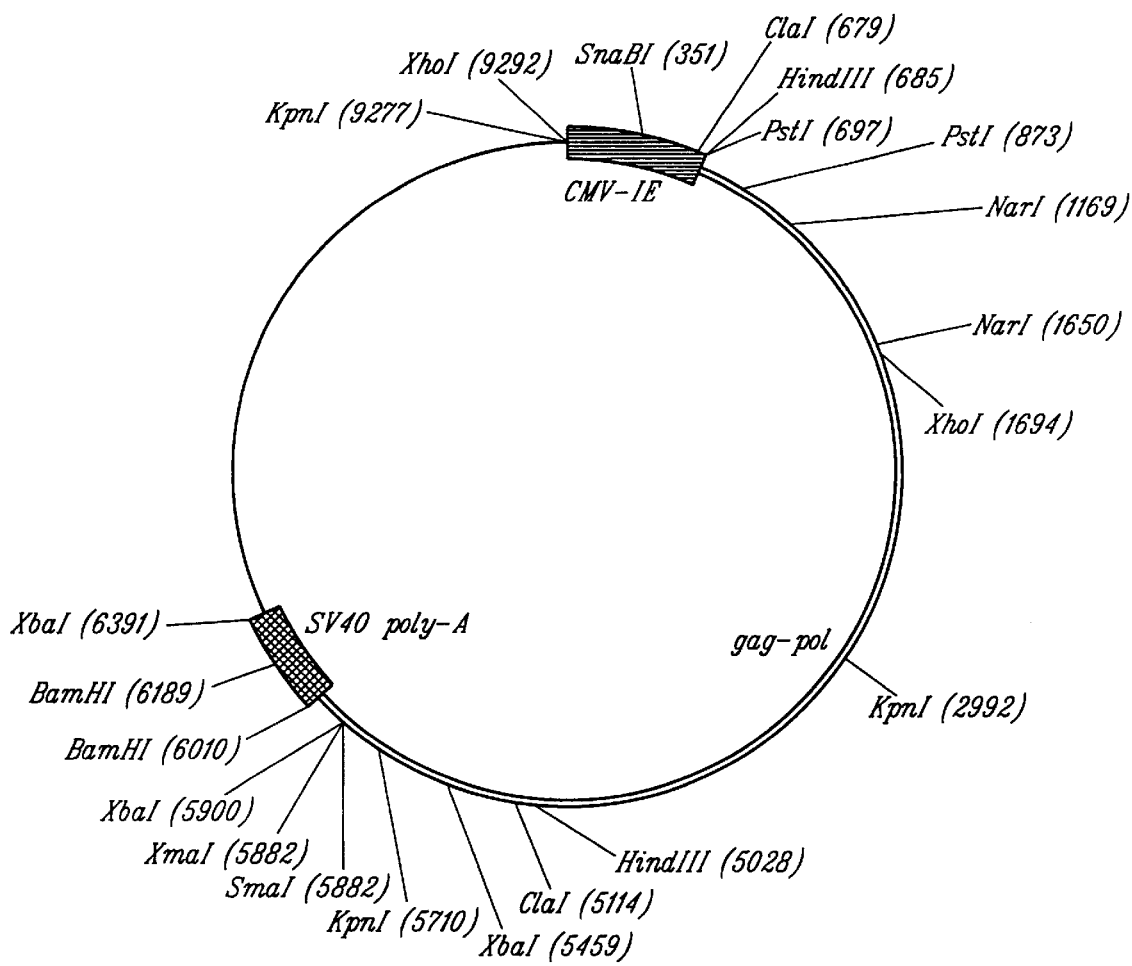
FIG. 12 is a schematic illustration of pCMV gag/pol.
Figure 13:
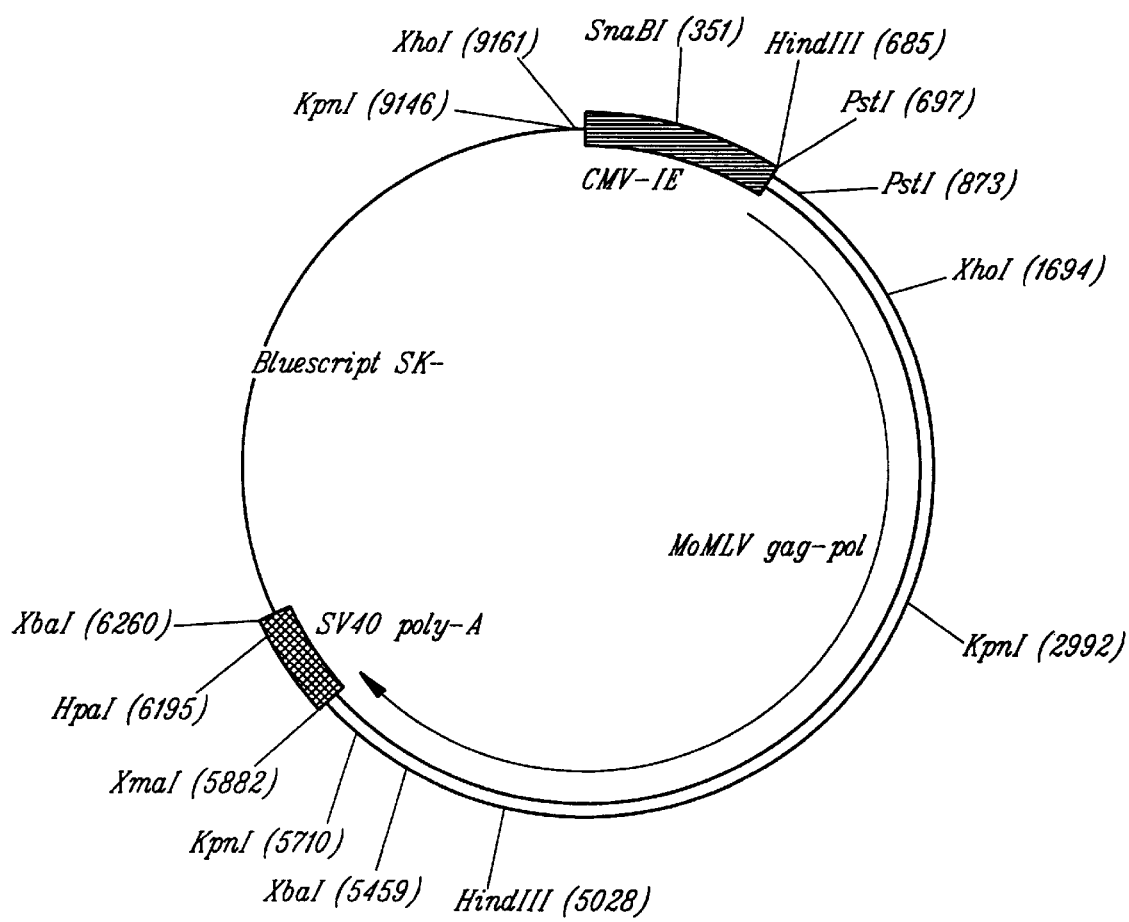
FIG. 13 is a schematic illustration of pCMVgpSma.

In order to prepare a gag/pol expression cassette which expresses full length gag/pol, pCMV gag/pol is constructed. Briefly, MoMLV sequence from PstI (BP567) to NheI (bp 7847) is cloned into the PstI-XbaI sites of pUC19 (New England Biolabs). The resultant intermediate is digested with HindIII and XhoI, and a 1008 bp fragment containing the gag leader sequence is isolated. The same intermediate is also digested with XhoI and ScaI, and a 4312 bp fragment containing the remaining gag and pol sequences is isolated. The two isolated fragments are then cloned into the HindIII and SmaI sites of pHCMV-PA, described above. The resultant construct, designated CMV gag/pol (FIG. 12) expresses MoMLV gag and pol genes.

In order to truncate the 3' end of the pol gene found in pCMV gag-pol, a 5531 basepair SnaBI—XmaI fragment containing a portion of the CMV IE promoter and all of gag-pol except the final 28 codons, is isolated from pCMV gag-pol. This fragment is cloned into the SnaBI and XmaI sites of pHCMV-PA. This construct expresses five new amino acids at the carboxy-terminus (Ser-Lys-Asn-Tyr-Pro) (SEQ ID NO: 6) pCMV gpSma).

Alternatively, these five amino acids may be eliminated by digesting pCMVgp SmaI and SmaI and adding an NheI (termination codons in three phases) linker (5'- CTA GCT ACG TAG) (SEQ ID NO: 14; New England Biolabs) at the end of the truncated pol sequence. This construct is designated pCMV gp Nhe. Both of these constructs eliminates potential crossover between gag/pol and env expression cassettes.

D. Gag-Pol Expression Cassette

Figure 14:
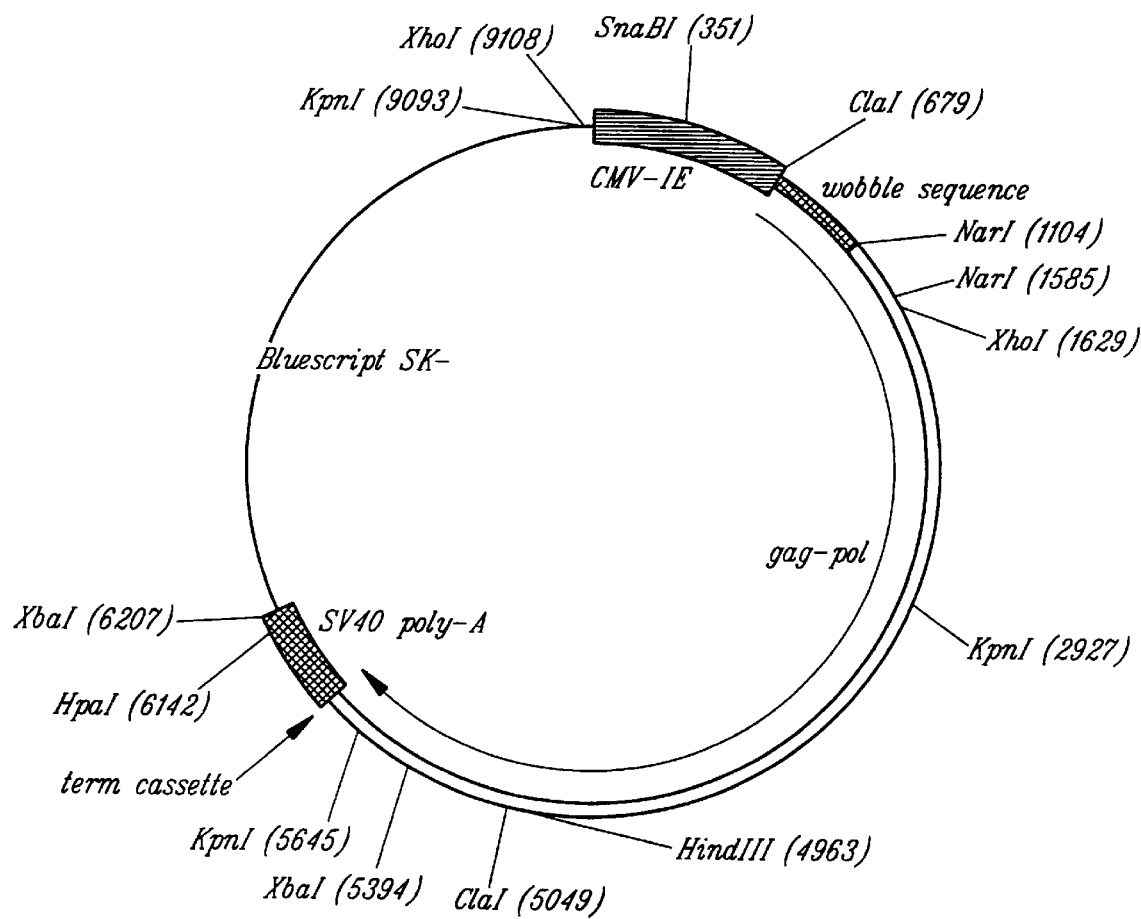
FIG. 14 is a schematic illustration of pCMVgp-X.

Parts B and C from above are combined to provide an expression vector containing a CMV IE promoter, gag-pol sequence starting from the new ClaI site (followed by ACC ATG and 412 bp of alternative or "wobble" gag coding sequence) and terminating at the SmaI site (MoMLV position 5750) followed by an SV40 polyadenylation signal, essentially as described below. Briefly, the approximately 451 bp double stranded wobble fragment from part A is ligated into PCR'II TA cloning vector (Invitrogen Corp.). The wobble PCR product naturally contains a 3' A-overhang at each end, allowing for cloning into the 3' T-overhang of pCR'II. The 422 bp ClaI-NarI wobble fragment from the pCR'II clone is removed and is ligated into the ClaI (Position 679, Figure pCMV gp Sma) and NarI (Position 1585) sites of pCMV gp Sma1 (Part B) (or pCMV gp Nhe). The ClaI site at position 5114 is methylated and not cut with ClaI). The product of that ligation is digested with NarI, and the MLV-K NarI fragment (positions 1035 to 1378) is inserted (SEQ ID NO: 1). This construct is designated pCMVgp-X (FIG. 14).

EXAMPLE 4

CONSTRUCTION OF ENV EXPRESSION CASSETTES

A. Creation of New 5' EagI Restriction Site

Starting with an EagI- EcoRI 626 bp subfragment from a 4070A amphotropic envelope (Chattopodhyay et al., *J. Vir.* 39:777, 1981; GenBank accession #MLV4070A, and #MLVENVC; SEQ ID NO: 13) cloned in a pBluescript II Ks+vector (containing the start codon), site directed mutagensis is performed upstream of the translation start site in order to change ACCATCCTCT GGACGGAC<u>AT G</u>. . . (SEQ ID NO: 7; position 19–39 of Genebank sequence #MLVENVC) to ACCCGGCCGT GGACGGAC<u>AT G</u> . . .

(SEQ ID NO: 8) and create new EagI site at position 23. This modification allows cloning of the amphotropic envelope sequence into an expression vector eliminating upstream 4070A sequence homologous to the gag-pol expression element is described in Example 2A.

B. Creation of a New 3' End for Env

Figures 18, 19A, 19B:
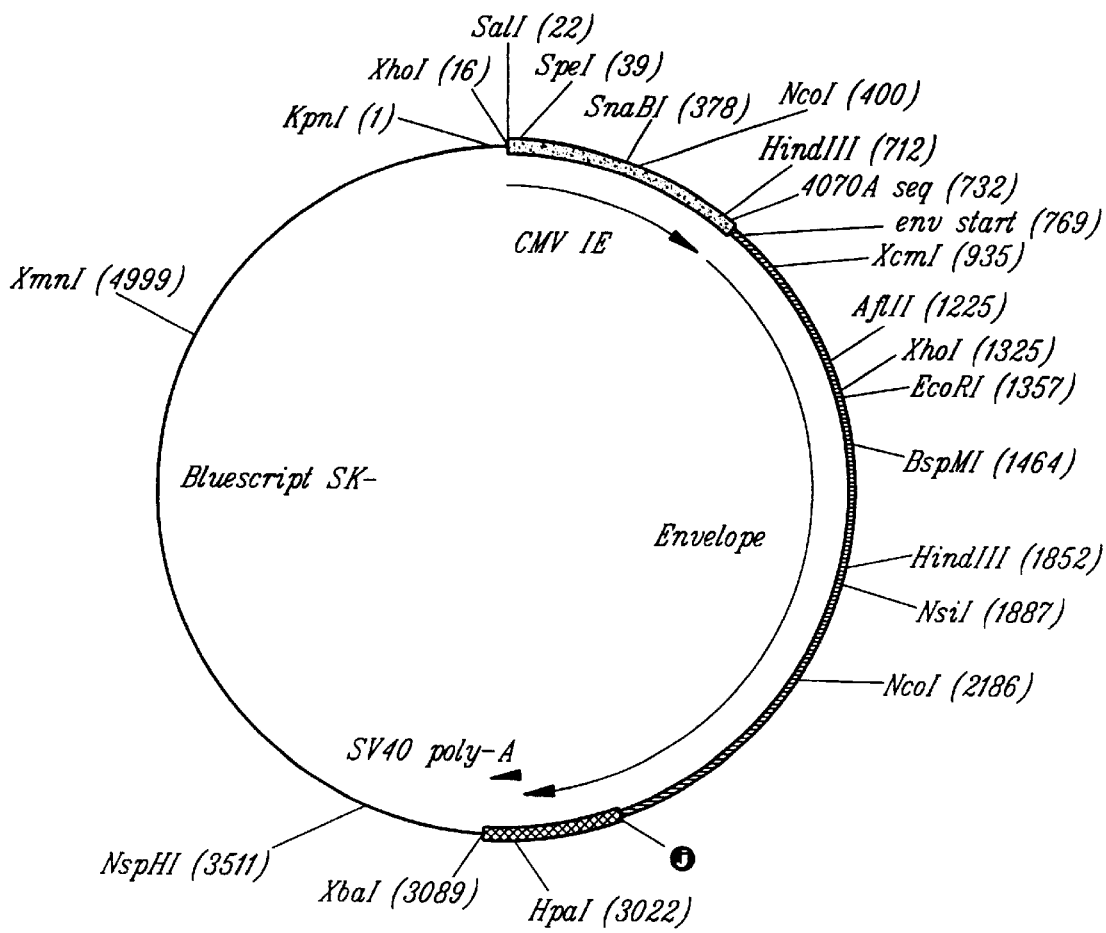
FIG. 18 is a schematic illustration of pCMV Envam-Eag-X-less.
FIG. 19A is a diagrammatic illustration of a "wobble" -gag construct.
FIG. 19B is a diagrammatic illustration of a "normal" -gag construct.
Figure 21:
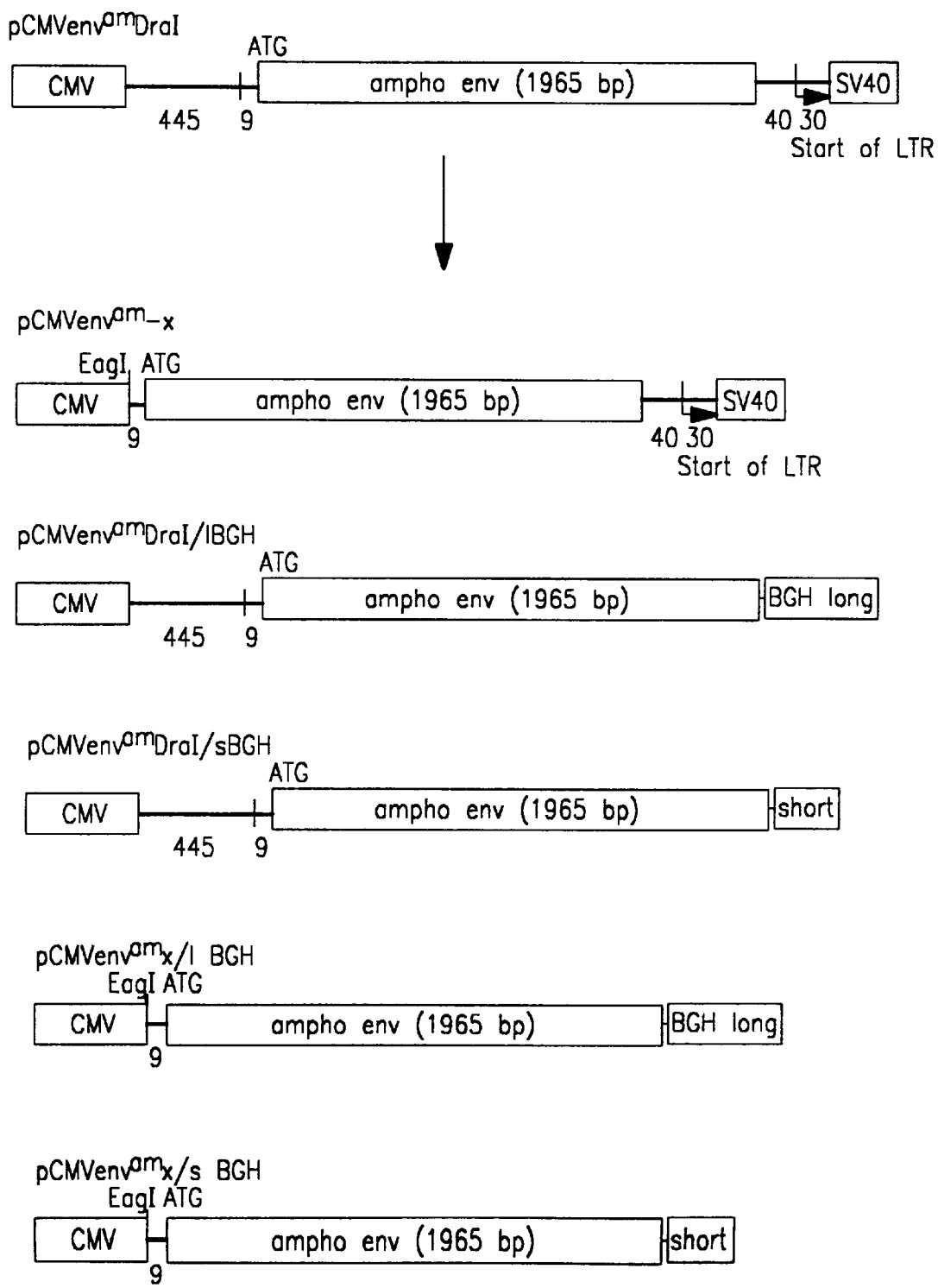
FIG. 21 depicts retroviral amphotropic envelope constructs starting with the pCMVenvAMDraI at the top of the page and modifications thereof. The exact modifications in the envelope constructs are described in the examples.

A new 3' end of the envelope expression element is created by terminating the sequence which enodes the R-peptide downstream from the end of the transmembrane region (p15E). Briefly, construct pHCMV-PA, described above, is first modified by digestion with NotI (position 1097), blunted and relegated to obliterate the overlapping Bluescript EagI site at the same position. pCMV Envam-Eag-X-less is then constructed by digesting the modified pHCMV-PA with EagI (position 671 and SmaI (position 712) and ligating in two fragments. The first is an EagI-NcoI fragment from 4070A (positions 1–1455) (SEQ ID NO: 13). The second is an MLV-K envelope fragment, NcoI-PvuII (positions 7227–7747) (SEQ ID NO: 1). The resultant construct from the three-way ligation contains the HCMV promoter followed by the SU (GP70) coding sequence of the 4070A envelope, the TM (p15e) coding sequence of MoMLV, and sequence encoding 8 residues of the R-peptide. In addition, this envelope expression cassette (pCMV Env am-Eag-X-less) (FIG. 18) shares no sequence with crossless retrovector backbones described in Example 1.

C. Envelope Expression Element

Figure 15:
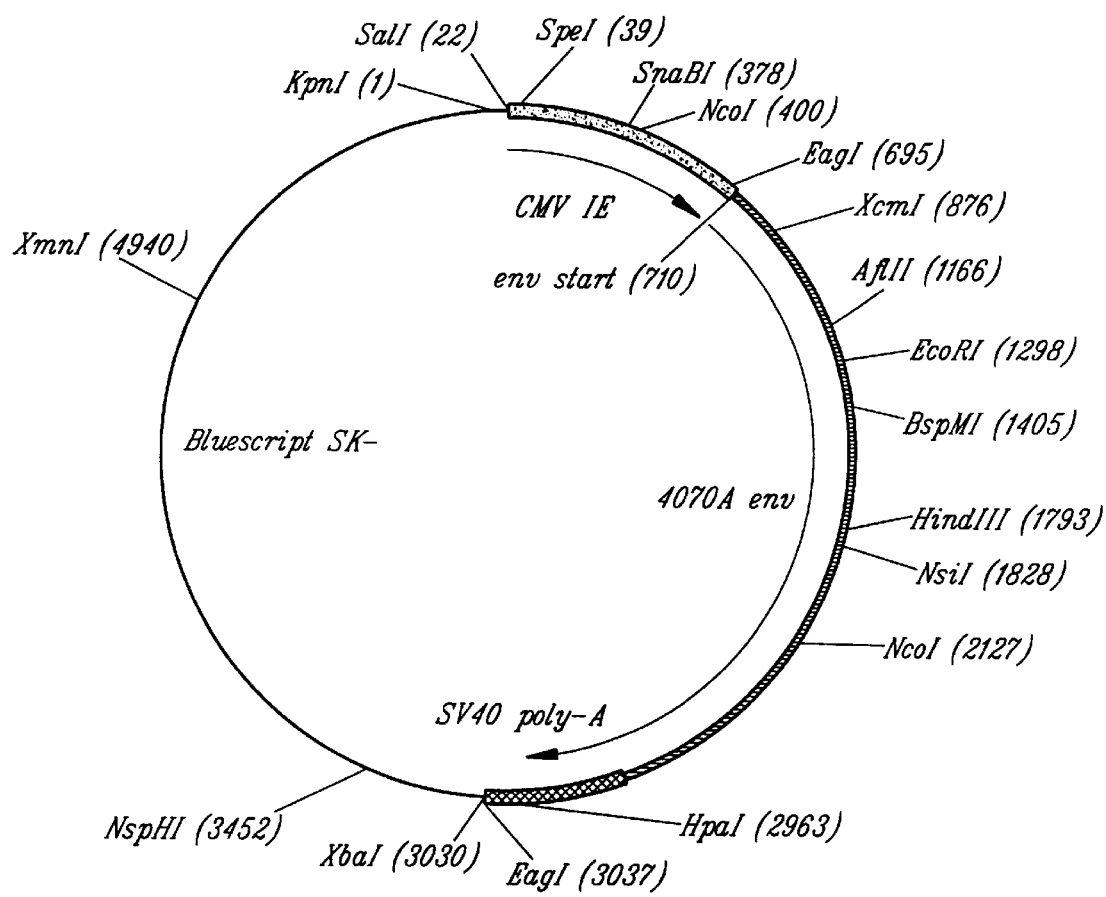
FIG. 15 is a schematic illustration of pCMV env-X.

Parts A and B from are combined to complete an amphotropic expression element containing the CMV promoter, 4070A SU, MoMLV TM and SV40 polyadenylation signal in a Bluescript SK- plasmid vector. This construct is called pCMVenv-X (FIG. 15). Briefly, the construct described in part A with a new EagI restriction site is digested with EagI and XhoI, and a 571 bp fragment is isolated. pCMV Envam-Eag-X-less (from part B) is digested with KpnI and EagI and the 695 bp fragment is reserved. pCMV Envam-Eag-X-less (from part B) is digested with KpnI and XhoI and the 4649 bp fragment is reserved. These two fragments are ligated together along with the 571 bp EagI to XhoI fragment digested from the PCR construct form part A. pCMVenv-X shares no sequence with crossless retrovector backbones nor the gag-pol expression element pCMV gp-X.

EXAMPLE 5

FUNCTIONALITY TESTS FOR GAG-POL AND ENV EXPRESSION CASSETTES

Figure 16:
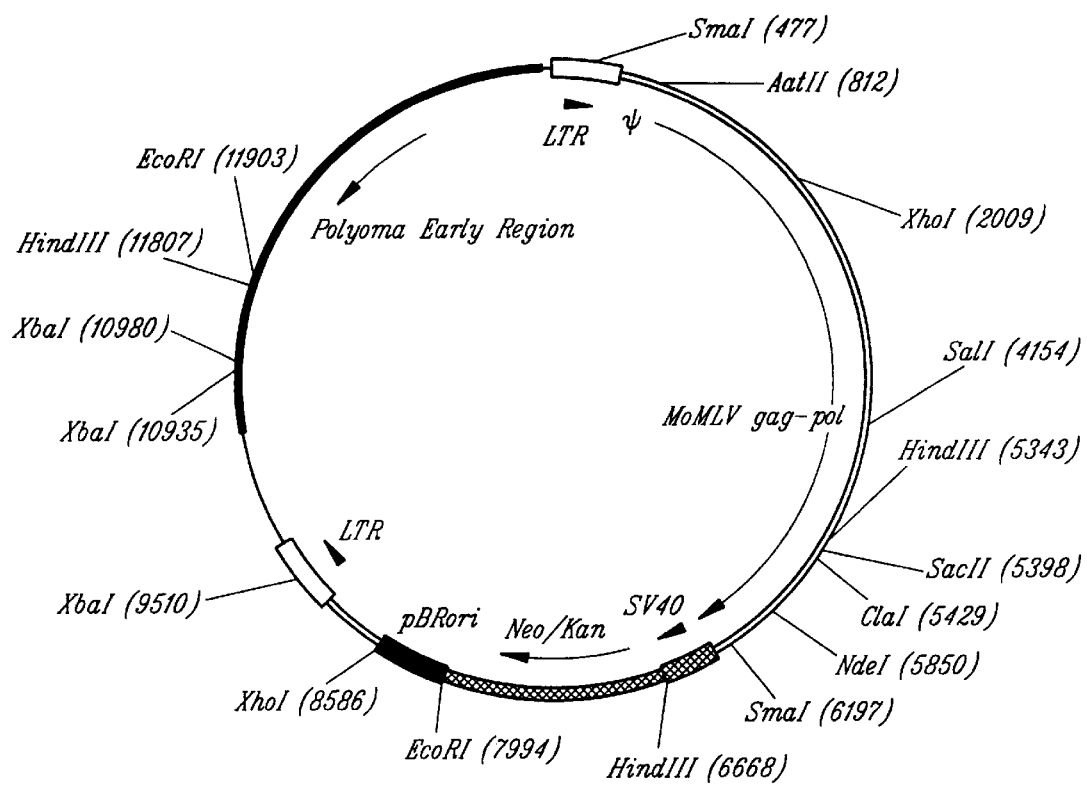
FIG. 16 is a schematic illustration of pRgpNeo.

Rapid tests have been developed in order to ensure that the gag-pol and env expression cassettes are biologically active. The materials for these tests consist of a cell line used for transient expression (typically 293 cells, ATCC, #CRL 1573), a target cell line sensitive to infection (typically HT 1080 cells, ATCC #CCL 121 ) and either pRGpNeo (FIG. 16) or pLARNL (Emi et al., *J. Virol* 65:1202–1207, 1991). The two later plasmids express rescuable retrovectors that confer G418 resistance and also express gag-pol, in the case of RgpNeo or env, in the case of pLARNL. For convenience, the organization of RgpNeo (FIG. 16) is set forth below.

In order to test expression cassettes such as pCMVgp-X for functionality of gag/pol, the plasmid is co-transfected with pLARNL at a 1:1 ratio into 293 cells. After 12 hours, the media is replaced with normal growth media. After an additional 24 hours, supernatant fluid is removed from the 293 cells, filtered through a 0.45 mm filter, and placed on HT 1080 target cells. Twenty-four hours after the treatment, the media is replaced with growth media containing 800 µg/ml G418. G418 resistant colonies are scored after one week. The positive appearance of colonies indicates that all elements are functional and active in original co-transfection.

For convenience, the organization of RgpNeo (FIG. 16) is set forth below: Position 1=left end of 5' LTR; Positions 1–6320=MoMLV sequence from 5'LTR to Sca 1 restriction site; Positions 6321–6675=SV40 early promoter; Positions 6676–8001=Neo resistance gene from Tn 5 (including prokaryotic promoter); and Positions 8002–8606=pBR origin of replication.

EXAMPLE 6

PACKAGING CELL LINE AND PRODUCER CELL LINE DEVELOPMENT

This example describes the production of packing and producer cell lines utilizing the above described retroviral vector constructs, gag/pol expression cassettes, and env expression cassettes, which preclude the formation of replication competent virus.

Briefly, for amphotrophic MoMLV-based retroviral vector constructs, a parent cell line is selected which lacks sequences which are homologous to Murine Leukemia Viruses, such as the dog cell line D-17 (ATCC No. CCL 183). The gag/pol expression cassettes are then introduced into the cell by electroporation, along with a selectable marker plasmid such as DHFR (Simonsen et al., *PNAS* 80:2495–2499, 1983). Resistant colonies are then selected, expanded in 6 well plates to confluency, and assayed for expression of gag/pol by Western Blots. Clones are also screened for the production of high titer vector particles after transduction with pLARNL.

The highest titer clones are then electroporated with an env expression cassette and a selectable marker plasmid such as hygromycin (see Gritz and Davies, *Gene* 25:179–188, 1983). Resistant colonies are selected, expanded in 6 well plates to confluency, and assayed for expression of env by Wester Blots. Clones are also screened for the production of high titer vector particles after transduction with a retroviral vector construct.

Resultant packaging cell lines may be stored in liquid Nitrogen at $10 \times 10^6$ cells per vial, in DMEM containing 10% irradiated Fetal Bovine Serum, and 8% DMSO. Further testing may be accomplished in order to confirm sterility, and lack of helper virus production. Preferably, both an S+L- assay and a *Mus dunni* marker rescue assay should be performed in order to confirm a lack of helper virus production.

In order to construct a producer cell line, retroviral vector construct as described above in Example 1 is electroporated into a xenotropic packaging cell line made utilizing the methods described above. After 24–48 hours, supernatant fluid is removed from the xenotropic packaging cell line, and utilized to transduce a second packaging cell line, thereby creating the final producer cell line.

EXAMPLE 7

HELPER DETECTION ASSAY COCULTIVATION, AND MARKER RESCUE

This example describes a sensitive assay for the detection of replication competent retrovirus ("RCR"). Briefly, $5 \times 10^5$ vector-producing cells are cocultivated with an equal number of *Mus dunni* cells (Lander and Chattopadhyay, *J. Virol.* 52:695, 1984). *Mus dunni* cells are particularly preferred for helper virus detection because they are sensitive to nearly all murine leukemia-related viruses, and contain no known endogenous viruses. At three, six, and nine days after the initial culture, the cells are split approximately 1 to 10, and $5 \times 10^5$ fresh *Mus dunni* cells are added. Fifteen days after the initial cocultivation of *Mus dunni* cells with the vector-producing cells, supernatant fluid is removed from cultures, filtered through a 0.45 mm filter, and subjected to a marker rescue assay.

Briefly, culture fluid is removed from a MdH tester cell line (*Mus dunni* cells containing pLHL (a hygromycin resistance marker retroviral vector; see Palmer et al., *PNAS* 84(4): 1055–1059, 1987) and replaced with the culture fluid to be tested. Polybrene is added to a final concentration of 4 mg/ml. One day 2, medium is removed and replaced with 2 ml of fresh DMEM containing 10% Fetal Calf Serum. One day 3, supernatant fluid is removed, filtered, and transferred to HT1080 cells. Polybrene is added to a final concentration of 4 mg/ml. On day 4, medium in the HT1080 cells is replaced with fresh DMEM containing 10% Fetal Calf Serum, and 100 mg/ml hygromycin. Selection is continued on days 5 though 20 until hygromycin resistant colonies can be scored, and all negative controls (e.g., mock infected MdH cells) are dead.

EXAMPLE 8

ASSAY FOR ENCAPSIDATION OF WOBBLE RNA SEQUENCE

This example describes a sensitive assay for the detection of encapsidation of RNA from constructs containing wobble or normal gag sequence. Briefly, a fragment of DNA from a "wobble" gag/pol expression cassette (Example 3), containing the CMV promoter and gag sequence to the XhoI site (MoMLV position 1561) is ligated to a SV40 neo-3' LTR DNA fragment from N2 (Armentano et al., supra) or KT-3 (see WO 91/02805 or WO 92/05266). This construct is diagrammatically illustrated in FIG. 19A, and is not expected to be encapsidated in packaging cell lines such as DA or HX (see (WO 92/05266) because it lacks a 5' LTR and primer binding site.

A second construct is also made, similar to the first except that the wobble sequence is replaced by normal gag sequence. Similar to the first construct, the RNA transcribed from this DNA is not expected to be encapsidated. This construct is diagrammatically illustrated in FIG. 19B.

The above constructs are separately transfected into a packaging cell line. The culture is then assayed for the ability to generate transducible G418-resistant retrovector. Neither construct results in transducible vector.

Cell cultures containing the above constructs are then transduced with the retrovector LHL (see Example 7). The cell culture, after selection, will now generate retrovector conferring hygromycin resistance to target cells. Further, if co-encapsidation is allowed by interaction between LHL RNA and the transcripts from the above constructs, statistically significant RT-mediated recombination can occur resulting in the transfer of G418 resistance to target cells.

EXAMPLE 9

CONSTRUCTION OF RETROVIRAL BACKBONES

This example describes several modifications of the retroviral vector pKT1 (FIG. 6) resulting in decreased sequence homology to the retroviral gag/pol and envelope expression constructs. In addition, two stop codons were introduced in the DNA sequence of the packaging signal sequence in order to increase the safety of these vectors. All modifications are summarized in FIG. 20 and the resulting retroviral backbone is called pBA-5b.

A. Substitution of Nonsense Codons in the Extended Packaging Sequence (Ψ+)

This example describes modification of the extended packaging signal (Ψ+) by PCR on the template KT-1 using primers that introduce two stop codons in the extended packaging signal sequence.—In particular, the template pKT-1 contains the modification ATT at the normal ATG start site of gag (position 621–623 of SEQ ID NO: 1). Here the start site was further modified to the stop codon, TAA, and an additional stop codon TGA was added to replace the codon TTA at position 645–647 of SEQ ID NO: 1.

Briefly, two sets of PCR reactions were carried out on pKT1, each introducing one stop codon. The primers for the PCR were designed such that the two PCR product had overlapping regions and a splice-overlap extension PCR (SOE-PCR) was carried out with the two PCR products in order to combine the two introduced stop codons on one strand. The first set of oligonucleotides introducing the change from ATT to TAA were 5'-GGG-AGT-GGT-AAC-AGT-CTG-GCC-TTA-ATT-CTC-AG (SEQ ID NO: 27) and 5'-CGG-TCG-ACC-TCG-AGA-ATT-ATT-TC (SEQ ID NO: 28) and the second set of oligonucleotides introducing the change from TTA to TGA were 5'CTG-GGA-GAC-GTC-CCA-GGG-ACT-TC (SEQ ID NO: 29) AND 5'GGC-CAG-ACT-GTT-ACC-ACT-CCC-TGA-ACT-TTG-AC (SEQ ID NO: 30). The flanking primers of the final 708 base pair PCR product introduced the AatII and the XhoI sites, at the 5' and 3', respectively.

The ends of the 708 base pair product were blunted and phosphorylated and the product introduced into the SmaI and EcoRV digested vector pBluescript SK-(Stratagene, San Diego, Calif.). The resulting plasmid was designated pBA-2, and is shown diagramatically in FIG. 20.

B. Removal of Retroviral Sequences Upstream and Downstream from the 3' LTR and Upstream and within 5' LTR Retroviral envelope sequence was removed upstream of the 3' LTR between the ClaI site and the TAG3 stop codon of the envelope coding sequence. The DNA sequence was modified by PCR such that the TAG stop codon was replaced by a ClaI site and the 97 nucleotides upstream from this new ClaI site to the original ClaI site were deleted, as well as the 212 base pairs of retroviral sequence downstream of the 3' LTR.

Briefly, the following two oligonucleotides were used for the PCR: 5'-CATCGATAAA ATAAAAGATT TTATT-TAGTC (SEQ ID NO: 31) and 5'-CAAATGAAAG ACCCCCGCTG AC (SEQ ID NO: 32) and the template was pKT1. The PCR product was cloned into pPCRII (Invitrogen, San Diego, Calif.) using the TA cloning kit (Invitrogen, San Diego, Calif.) and called pBA-1.

Subsequently, pBA-2 (described in section A above) was digested with XbaI and AatII which deleted a part of the multiple cloning site and into this linearized vector the 780 base pair fragment from NheI and AatII from pKT1 was cloned, resulting in the plasmid pBA-3. This plasmid pBA-3 combined the shortened 5' LTR with the above described packaging region including the two introduced stop codons.

Subsequently, pBA-1 was digested with ClaI and ApaI resulting in a 640 base pair fragment that was cloned into the ClaI and ApaI digested pBA-3 resulting in the plasmid pBA-4. This plasmid combines the above described 5' LTR and the packaging signal with the 3' LTR.

Subsequently, pBA-4 was digested with ApaI and EcoRI, ends blunted and religated in order to remove extraneous 3' polylinker sites, resulting in plasmid pBA-5a.

Subsequently, pBA-5a was cut with NotI (blunted) and EcoRI and introduced into SmaI and EcoRI digested pUC18 (GIBCO/BRL, Gaithersburg, Md.) resulting in pBA-5b. This construct moved the retroviral vector from a pBluescript into an alternate pUC18 vector.

EXAMPLE 10

Insertion of Genes of Interest into Cross-less Retroviral Vector Backbone pBA-5b This example describes the insertion of two genes of interest, gp120(HIV env/rev) and HSV-TK along with the neomycin gene into pBA-5b. Briefly, the sequence encoding gp120 was taken from construct pKT1 (FIG. 6; see also Chada et al., *J. Vir.* 67:3409–3417, 1993). This vector is also referred to as N2IIIBenv.

A. Introduction of HSV-TK and Neomycin into the Retroviral Vector pBA-5b

The HSV-TK gene was retrieved by digesting pBH-1 (PCY#UU 091-02805) with XhoI and EcoRI resulting in a 1.2 kb fragment. The neomycin gene driven by the SV40 promoter was retrieved by digesting pKT1 with EcoRI and BstBI resulting in a 1.3 kb fragment. Both fragments were cloned into a XhoI and ClaI digested pBA-5b resulting in the retroviral vector pMO-TK.

B. Introduction of HIV env/rev and neomycin into the retroviral vector pBA-5b

The HIV env/rev and neomycin genes were retrieved by digesting pKT1 with XhoI and BstBI resulting in a 4.4 kb fragment which was cloned into the XhoI and ClaI digested pBA-5b resulting in the retroviral vector pBA-6b.

EXAMPLE 11

Functionality Tests for the Cross-less Retroviral Backbones pBA-6b and pMO-TK

Rapid tests are described in more detail below which ensure that the retroviral vectors coding for HIV env/rev and neomycin (pBA-6b) and HSV-Tk and neomycin (pMO-TK) are comparable to the original retroviral vectors with regard to expression levels the genes of interest (HIV env/rev and HSV-TK) and titers.

A. Comparison of Transient and Stable Neo titer from pKT1 Versus pBA-6 in Transfected Non-clonal Vector Producing Pools Retroviral vectors pKT1 or pBA-6 were transfected into DA packaging cells via $CaPO_4$-precipitation using the Pro-Fection kit from Promega according to manufacturer's protocol (Promega, Madison, Wis.). The transient supernatant was collected 48 hours posttransfection, sterile-filtered (0.45 mm) and placed on HT 1080 target cells (HT 1080 cells, ATCC #CCL 121) in the presence of 8 mg polybrene/ml. Twenty-four hours after that treatment, the media is replaced with growth media containing 800 µg/ml G418. G418 resistant colonies are scored after one week. The positive appearance of colonies indicates that all elements are functional and active in the original co-transfection.

For the stable neo titer, the transfected DA cells were cultured in selection media containing 800 µg/ml G418 for two weeks or until the untransfected control cells were dead. Titer of the supernatants from the confluent vector producing pools was determined as described above.

Results of transient and stable neo titers are presented in Table 2.

TABLE 2

Transient and stable neo titer of pKT-1 versus pBA-6b retroviral vectors in transfected and selected non-clonal DA vector producing pools Retroviral vector coding for HIV env/rev plus neo

|  | Transient neo titer in CFU/ml |
| --- | --- |
| pKT-1 | $5.0 \times 10^4$ |
| pBA-6b (cross-less retroviral vector) | $2.5 \times 10^4$ |
|  | Stable neo titer in CFU/ml |
| pKT-1 | $5.6 \times 10^6$ |
| pBA-6b (cross-less retroviral vector) | $6.7 \times 10^6$ |

B. Comparison of gp120 and rev expression levels of pKT1 versus pBA-6b in vector producing pools and target cells The supernatants from the above described selected non-clonal pools DA/KT1 and DA/BA-6b were used to transduced HT 1080 target cells as described above. G-418 resistant colonies were selected as described above and the pools were named HT 1080/KT1 and HT 1080/BA-6b.

The DA/KT1, DA/BA-6b vector producer pools as well as the HT 1080/KT1 and HT 1080/BA-6b pools were lysed and gp120 and rev protein levels were estimated by Western Blot analysis according to standard procedures.

Results are presented in Table 3.

TABLE 3

Comparison of pKT1 and pBA-6b retroviral vector with regard to gp120 and rev expression levels in transduced and selected non-clonal DA vector producing pools and transduced and selected target cells

| G-418 selected pools analyzed | gp120 expression levels | Rev expression levels |
| --- | --- | --- |
| DA | − | − |
| DA/KT1 | + | + |
| DA/BA-6b | ++ | + |
| HT-1080 | − | − |
| HT-1080/KT1 | +++ | + |
| HT-1080/BA-6b | +++ | + |

C. Comparison of Stable Neo Titer from pKT1 Versus pBA-6 in Transduced Non-Clonal Vector Producing Pools The retroviral vectors pBH1 or pMO-TK were transduced into various packaging cell lines using transient transfection produced VSV-G pseudotyped vectors as described in PCT/US91/06852 entitled "Packaging Cells" and PCT/US91/05699 entitled "Viral Particles Having Altered Host Range." The following packaging cell lines were used: DA, HA, HP, HX, 2A, 2X, as described in PCT/US91/06852 and PCT/US91/05699.

For the stable neo titer, the transduced packaging cell line pools were cultured in selection media containing 800 µg/ml G418 for two weeks or until the untransfected control cells were dead. Titers of the supernatants from the confluent vector producing pools were determined as described above.

TK expression levels were determined by Western Blot analysis of lysates of the specified vector producing pools.

Results of stable neo titers as well as TK expression levels in the various vector producing pools are presented in Table 4.

TABLE 4

Comparison of pBH-1 and pMO-TK in various packaging cell lines with regard to neo titers and TK expression levels in the transduced and selected vector producing pools

| G-418 selected pools analyzed | Stable neo titers (CFU/ml) | TK expression levels |
|---|---|---|
| DA/BH-1 | $6.0 \times 10^5$ | ++ |
| DA/MO-TK | $1.3 \times 10^6$ | ++ |
| HA/BH-1 | $3.7 \times 10^5$ | +++ |
| HA/MO-TK | $1.6 \times 10^5$ | +++ |
| HP/BH-1 | $<1 \times 10^3$ | ++ |
| HP/MO-TK | $<1 \times 10^3$ | ++ |
| HX/BH-1 | $3.5 \times 10^5$ | ++ |
| HX/MO-TK | $1.0 \times 10^5$ | ++ |
| 2A/BH-1 | $1.3 \times 10^5$ | + |
| 2A/MO-TK | $1.7 \times 10^5$ | + |
| 2X/BH-1 | $3.2 \times 10^5$ | + |
| 2X/MO-TK | $5.2 \times 10^5$ | + |

EXAMPLE 12

Construction of ENV Expression Cassettes

A. Cloning of Long and Short Bovine Growth Hormone Termination-Polyadenylation Sequences The Long Bovine Growth Hormone (BGH) termination-polyadenylation sequence (positions 2330–2551 of Genebank sequence #BOVGHGH) was PCR amplified from the plasmid pCDNA3 (Invitrogen Corp, San Diego Calif.) using the forward primer 5'CCTAT<u>GAGCT</u>CGCCTTCTAG TTGCCAGC (SEQ ID NO: 33) (positions 2330–2346 of Genebank sequence #BOVGHGH) containing a restriction site for Sac I restriction endonuclease (underlined) and the reverse primer 5'CCTAT<u>GAATT</u><u>C</u>GC<u>GGCCGCC</u> ATAGAGCCCA CCGCATCC (SEQ ID NO: 34) (positions 2551–2531 of Genebank sequence #BOVGHGH) containing restriction sites for EcoR I and Not I (underlined). The PCR fragment was digested with Sac I and EcoR I and inserted into Sac I/EcoR I digested pBGS131 vector (American Type Culture Collection #37443) to create pBGS-long BGH. Similarly, the short BGH termination-polyadenylation sequence (positions 2415–2463 of Genebank sequence #BOVGHGH) was PCR amplified using the forward primer 5'TATATAT<u>GAG</u><u>CT</u>CTAATAAA ATGAGGAAAT TGCATCGCAT TGTC (SEQ ID NO: 35) (positions 2415–2445 of Genebank sequence #BOVGHGH) containing a restriction site for Sac I restriction endonuclease (underlined) and the reverse primer 5'CCTAT<u>GAATT</u> <u>CGCGGCCGCA</u> TAGAATGACA CCTACTCAGA CAATGCGA (SEQ ID NO: 36) (positions 2463–2436 of Genebank sequence #BOVGHGH) containing the restriction sites for EcoR I and Not I (underlined). A template was not required because the primer sequences overlap. The PCR fragment was digested with Sac I and EcoR I and inserted into Sac I/EcoR I digested pBGS131 vector to create pGBS-short BGH.

B. Creation of a New 3' End for Env

The entire MoMLV amphotropic envelope coding region was PCR amplified from the plasmid pCMVenvAmDra (described in PCT/US91/06852 example 2) using the forward primer GCTCGTTTAG TGAACCGTCA G (SEQ ID NO: 37) (positions 606–631 of pCMVenvAmDra) and the reverse primer TATCC<u>GAGCT</u> CATGGCTCGT ACTCTATGG (SEQ ID NO: 38) (positions 3136–3118 of pCMVenvAmDra). The reverse primer contains the restriction site for Sac I restriction endonuclease (underlined) directly after the stop codon of amphotropic envelope (bold). The PCR fragment was digested with Sac I and Bgl II and inserted into Sac I/Bgl II digested pBGS-long BGH and pBGS-short BGH vector to create pBGSAmEnv-long BGH and pBGSAmENV-short BGH respectively. These constructs contain amphotropic envelope with no MoMLV sequence past the termination codon, followed by the BGH termination-polyadenylation sequence.

C. Insertion of Env-BGH into an Expression Plasmid

The plasmid pCMVenvAmDra (described in PCT/US91/06852, Example 2) was digested with BstB I and Not I restriction endonucleases. This digest removes approximately 210 bases of the 3' coding region of amphotropic envelope, approximately 75 MoMLV 3'noncoding bases, and the SV40 termination-polyadenylation sequence. The small BstB I/Not I fragment of the plasmids pBGSAmEnv-long BGH and pBGSAmENV-short BGH was inserted into the BstB I/Not I digested pCMVenvAmDra expression plasmid to create pCMVenvAmDra/LBGH and pCMVenvAmDra/SBGH respectively. The small BstB I/Not I fragment of the plasmids pBGSAmEnv-long BGH and pBGSAmENV-short BGH was also inserted into BstB I/Not I digested plasmid pCMVenv-X (Example 4) to create the plasmids pCMVenvX-long BGH and plasmids pCMVenvX-short BGH.

D. Construction of the envelope gene truncated in the 5' and 3' non-coding regions of pCI The entire MoMLV amphotropic envelope coding region was PCR amplified from the plasmid pCMVenvAmDra (described in PCT/US91/06852, Example 2) using the forward primer 5' CACCTAT<u>GCT AGC</u>CACCATG GCGCGTTCAA CGCTCTC (SEQ ID NO: 39) containing a restriction site for NheI restriction endonuclease (underlined) and the reverse primer 5' CACCTAT<u>GCG GCCGC</u>TCATG GCTCGTACTC TATGGG (SEQ ID NO: 40) containing a restriction site for NotI restriction endonuclease (underlined). The PCR fragment was digested with NotI and NheI and inserted into a NotI/NheI digested pCI vector (Promega Corp, Madison Wis.) to create pCI/envam. The PCR fragment contains the entire coding region of the envelope gene including the NheI site followed by the Kozak sequence CACC upstream of the ATG start codon and the TCA stop codon followed by the NotI site.

E. Construction of the envelope gene truncated in the 5' and 3' non-coding regions in pCMVb Similarly to pCI/envam, the entire MoMLV amphotropic envelope coding region was PCR amplified from the plasmid pCMVenvAmDra (described in PCT/US91/06852, Example 2) using the forward primer 5' CACCTAT<u>GCG</u> <u>GCCGC</u>CACCA TGGCGCGTTC AACGCTCTC (SEQ ID NO: 41) containing a restriction site for NotI restriction endonuclease (underlined) and the reverse primer 5' CACCTAT<u>GCG GCCGC</u>TCATG GCTCGTACTC TATGGG (SEQ ID NO: 40) containing a restriction site for NotI restriction endonuclease (underlined). The PCR fragment was digested with NotI and inserted into the NotI digested pCMVb vector (Clontech Laboratories Inc., Palo Alto, Calif.) deleting the b-galactosidase gene from pCMVb to create pCMV-b/envam. The PCR fragment contains the entire coding region of the envelope gene including the NotI site followed by the Kozak sequence CACC upstream of the ATG start codon and the TCA stop codon followed by the NotI site.

F. Construction of the envelope gene truncated in the 5' and 3' non-coding regions in pCMVenvAmDra/LBGH/EAG del The plasmid pCMVenvAmDra/LBGH/EAG del was constructed from the plasmid pCMVenvAmDra/LBGH (described in example 12-c) by deletion of 441 base pairs from the agI site at position 695 to the EagI site at position at 1136 just upstream of the env start codon. This was accomplished by digesting pCMVenvAmDra/LBGH with agI and gel purifying the resulting bands of 2,227 and 3,573 base pairs. These two fragments were then ligated together and screened for correct orientation, such that the env start site was positioned downstream of the CMV promoter. The resulting construct was named pCMVenvAmDra/LBGH/EAG del.

EXAMPLE 13

Construction of Various gag/pol Expression Plasmids with Partially or Completely Reduced Sequence Overlap to the Cross-less Retroviral Backbone and Envelope This example describes several modifications of the MoMLV gag/pol expression plasmid pSCV10 (PCT/US91/06852, WO 92/05266) resulting in decreased or eliminated sequence homology to the retroviral backbone and envelope expression constructs.

A. Creation of New Codons for the 5'Gag

This example describes the gag/pol expression plasmid cassette that contains wobbled non-coding sequences upstream from the gag start site, thereby reducing recombination potential between the gag/pol expression element and the extended packaging signal of a retroviral vector construct, and inhibiting co-packaging of the gag/pol expression element along with the retrovector. In order to construct such an expression cassette a 406 bp DNA fragment with a ClaI site at the 5' end (underlined) and a NarI site at the 3' end (underlined) was synthesized by Operon (Operon Technologies Inc, Alameda Calif.). The sequence of the 406 bp DNA fragment was verified and is provided in Table 5. The synthesized DNA was transferred to a shuttle plasmid as a ClaI-NarI fragment to create the plasmid pWOB.

TABLE 5

ATCGATACCATGGGGCAAACCGTGACTACCCCTCTGTCCCTCACACTGGGCC (SEQ ID NO: 42)
ATTGGAAGGACGTGGAAAGAATTGCCCATAATCAAAGCGTGGACGTCAAAA
AACGCAGGTGGGTGACATTTTGTAGCGCCGAGTGGCCCACATTCAATGTTG
GCTGGCCTAGGGATGGAACTTTCAATCGCGATCTGATTACTCAAGTGAAAA
TTAAAGTGTTCAGCCCCGGACCCCACGGCCATCCCGATCAAGTTCCTTATAT
TGTCACATGGGAGGCTCTCGCTTTCGATCCACCACCTTGGGTGAAACCATTC
GTGCATCCCAAACCACCTCCACCCCTCCCACCCAGCGCTCCTAGCCTGCCCT
TGGAGCCCCCACGAAGCACACCACCCAGGAGCAGCTTGTACCCTGCTCTGA
CCCCCAGCCTCGGCGCC

The ClaI-NarI fragment from pWOB was isolated by ClaI-NarI digest, and the 406 bp fragment cloned into the ClaI-NarI site of pSV10 to create the plasmid pSCV10/wob (-NarI fragment) which resulted in the loss of the 481 bp NarI-NarI fragment just downstream of the wobbled ClaI-NarI fragment.

B. Creation of a 5' truncated gag/pol construct without MoMLV sequence upstream of the start codon in pSCV10

This example describes the gag/pol expression plasmid cassette that eliminated the MoMLV sequence upstream of the ATG start codon in order to prevent sequence overlap to the retroviral backbone.

Briefly, a new ClaI site followed by an ideal Kozak translational start sequence was introduced upstream of the start codon of the gag/pol construct pSCV10 by PCR using the forward primer 5' CGA<u>ATCGATA</u> CCATGGGCCA GACTGTTACC AC (SEQ ID NO: 43) (the ClaI site is underlined) and the reverse primer 5' CATT<u>CTGCAG</u> AGCAGAAGGT AAC (SEQ ID NO: 44) containing a restriction site for PstI (underlined). The PCR fragment was digested with ClaI and PstI and the 131 bp fragment cloned into pSCV10 replacing the existing ClaI-PstI DNA fragment to create the plasmid pSCV10/5' truncated g/p.

C. Creation of a 5' truncated gag/pol construct without MoMLV sequence upstream of the start codon in pCI This example describes the construction of the 5' truncated gag/pol construct analogous to that described under section B above in the pCI (Promega Corp, Madison, Wis.) vector backbone.

Briefly, fragments were prepared for a three-way ligation as follows: pCI was digested with SmaI and NotI and the 4 kb fragment was isolated. pSCV10 was digested with XhoI and NotI and the 4.7 kb fragment was isolated. pSCV10/5' truncated g/p as described in section B was digested with ClaI, filled in with Klenow to blunt, then digested with XhoI and the 0.95 kb fragment was isolated. These three fragments were then ligated together to give the final plasmid pCI/5' truncated g/p.

D. Creation of a 5' truncated and wobbled gag/pol construct in pCI

This example describes the construction of the 5' truncated and wobbled gag/pol construct in the pCI vector where the 5' truncation as described in section C and the wobbled gag sequences as described in section A were combined.

Briefly, the wobbled gag/pol sequence (0.47 kb) was retrieved from plasmid pSCV10/wob (-NarI fragment) as described in section A above by digestion with ClaI and XhoI. This fragment was cloned into the ClaI-XhoI digested pBluescript SK- (Stratagene, San Diego, Calif.) to create pBluescript/wob (-NarI fragment). This plasmid was digested with EcoRI and NarI to retrieve the wobbled gag sequence and the EcoRI-NarI fragment cloned into the EcoRI-NarI digested pCI/5' truncated g/p described in section C above in order to create pCI/5' truncated wob g/p.

E. Creation of a 5' and 3' truncated gag/pol construct in pCI and pSCV10

This example describes the construction of the 5' and 3' truncated gag/pol construct in the pCI vector where the 5' truncation as described in section C is combined with the following 3' truncation upstream of the stop codon eliminating the DNA sequence coding for the last 28 amino acids of the pol protein.

Briefly, the plasmid pCI/5' truncated g/p described in section C was linearized with the restriction enzyme SmaI which is located 84 bases upstream of the gag/pol termination codon in the open reading frame of gag/pol. The linearized plasmid was ligated to the oligonucleotide 5' TAAGCGGCCG CTTA (SEQ ID NO: 45). This oligonucleotide is self-complementary and forms a palindromic duplex containing a TAA termination codon and a NotI restriction endonuclease site. After ligation of 100 ng vector and 5 µM oligo in the presence of T4 DNA ligase, the reaction was purified by GeneClean and digested with SmaI to recut any vector that did not contain an insert. The reaction was used to transform XL1 Blue *E. coli* (Stratagene, San Diego, Calif.) and plasmid DNA from a correct clone was then digested with NotI. NotI cuts in the inserted oligonucleotide as well as just upstream of the SV40 termination/ polyadenylation site of the pCI vector. The digested plasmids were purified by Geneclean and religated to recircularize. Bacteria were transformed and clones were identified which deleted the sequences between the NotI site introduced by the oligonucleotide and the NotI site in the pCI vector. These sequences include sequences encoding the last 28 amino acids of gag/pol as well as MoMLV sequences and vector sequences carried over from pSCV10. The resulting gag/pol construct was named pCI-GPM. The identically shortened gag/pol region was cloned by standard techniques into a pSCV10 background expression cassette. This expression plasmid was named pSCV10/5',3'tr.

F. Creation of a 5' and 3' truncated and wobbled gag/pol construct in pCI

This example describes the construction of the 5' and 3' truncated and wobbled gag/pol construct in the pCI vector combining the 5' truncation and wobbled gag/pol sequence from section D above with the 3' truncation described in section E above.

Briefly, pCI/5' truncated wob g/p was linearized with SmaI and all further steps leading to the 3' truncation of gag/pol were carried out as described in section E above, leading to the 5' and 3' truncated and wobbled gag/pol construct in pCI named pCI-WGPM.

EXAMPLE 14

Figure 22A:
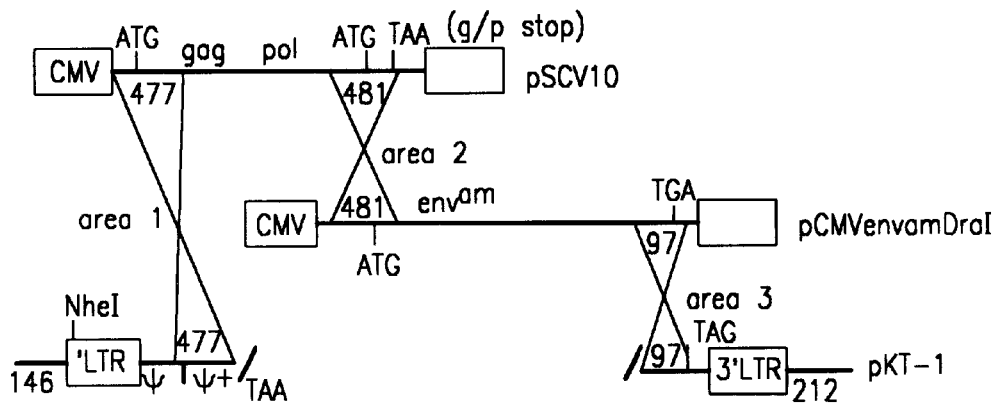
FIGS 22A, 22B and 22C are schematics showing retrovirus with three regions (A), one region (B) and no region (C) of sequence overlap.

Construction and Testing Titer Potential of PCLs with Various Combinations of gag/pol and env Expression Cassettes Resulting in PCLs with Various Degrees of DNA Sequence Overlap Between the Retroviral Components: gag/pol, env and Retroviral Vector This example describes the production of PCLs based on various combinations of the gag/pol and env expression cassettes described above and in Examples 12 and 13. The three unmodified retroviral components gag/pol, env and retroviral vector (PCT Application No. WO 92/05266) result in three areas of sequence overlap (area 1–3) in a VCL as shown in FIG. 22A. PCLs/VCLs with reduced sequence overlap can be produced with elimination of any combination of these three sequence overlap areas for example, a PCL/VCL may eliminate sequence overlap of area 1, area 2 or area 3 only, a combination of any two or all three areas. Production and potential titer analysis of PCLs with all three overlaps eliminated (FIG. 22C) as well as PCLs with the first area of overlap reduced and area 2 and 3 eliminated (FIG. 22B) are described below. A critical issue in the production of PLCs with reduced sequence overlap is the maintenance of high titer potential. Therefore, the titer potential of the PCLs with reduced sequence overlap were analyzed and compared extensively to existing PCLs with unmodified PCL components such as the DA and HA PCLs described in PCT Application No. WO 92/05266.

A. Production of PCLs with one area of sequence overlap between PCL components

Figure 22B:
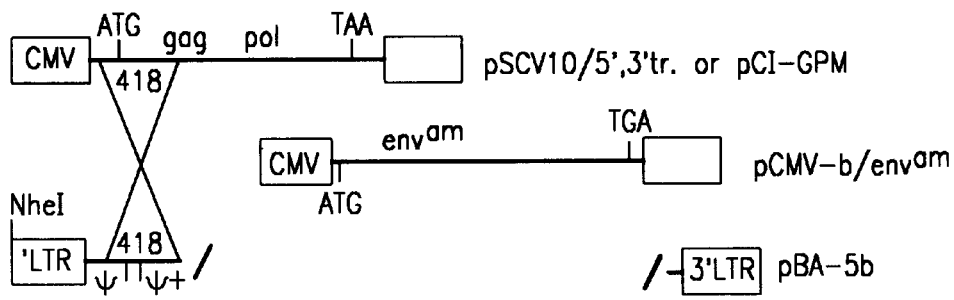
Figure 22C:
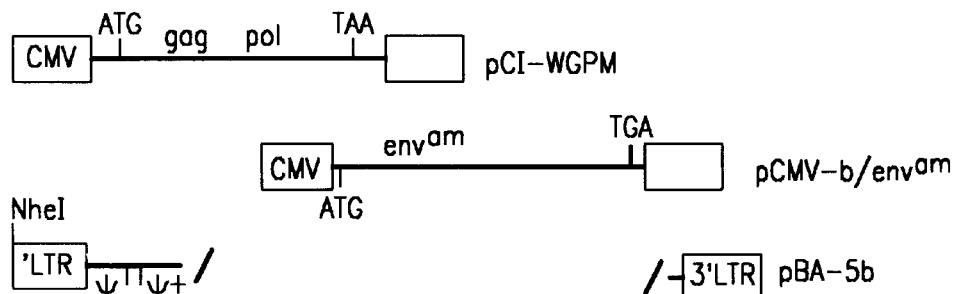

This example describes the production of PCLs with the gag/pol expression plasmid cassette pSCV10/5',3'tr. or pCI-GPM described in Example 13 E and the env expression plasmid pCMV-b/envam described in Example 12 E. PCLs with these gag/pol and env expression plasmids in conjunction with a retroviral vector derived from pBA-5b (Example 9) result in VCLs where sequence overlap areas 2 and 3 are eliminated and area 1 is reduced (FIG. 22B). The cell lines HT 1080 (ATCC #CCL 121) and D17 (ATCC #CCL 183) were used as parent cell lines to establish the PCLs.

Briefly, either gag/pol plasmid pSCV10/5',3'tr. or pCI-GMP was co-transfected together with a phleomycin$^r$ expressing marker plasmid into HT 1080 and D17 cells, respectively, via $CaPO_4$-precipitation using the ProFection kit from Promega according to manufacturer's protocol (Promega, Madison, Wis.). The transfected cells were selected with media containing zeocin™ (Invitrogen, Carlsbad, Calif.) at a concentration of 150 mg/ml for HT 1080 cells and 170 mg/ml for D17 cells until untransfected control cells were dead. HT 1080 and D17 gag/pol pools were dilution cloned into 96-well microtiter plates according to standard protocols where clonality was ensured by seeding cell densities that yield a maximum of 30% of wells with cell growth. HT 1080 and D17 derived gag/pol intermediate clones were isolated and analyzed for intracellular p30 expression levels in a standard Western blot using primary p30-specific goat antibodies and secondary, HRP-labeled rabbit anti-goat antibodies. These gag/pol clones were compared to HTSCV21 and D17 4-15 which are the HT 1080 and D17 gag/pol intermediate clones for the PCLs HA and DA, respectively (PCT #WO 92/05266). DA and HA have all three areas of sequence overlap (FIG. 22A). Results of the p30 Western are shown below in Table 6.

TABLE 6

HT 1080 and D17 derived clones screened for intracellular p30 levels after introduction of gag/pol expression cassettes pSCV10/5',3'tr. or pCI-GPM

| Gag/pol intermediates | #clones screened for p30 | #clones positive for p30 — (%) | p30 expression levels |
|---|---|---|---|
| D17gag/pol (pCI-GPM) | 80 | 32 (40%) | 3–4 clones have p30 levels comparable to D17 4-15 |
| HT 1080gag/pol (pSCV10/5',3'tr.) | 100 | 24 (24%) | 15 clones have p30 levels comparable or higher than HTSCV21 |

The 18 HT 1080 and 12 D17 gag/pol intermediates with the highest p30 expression levels were analyzed for titer potential.

Briefly, a retroviral ecotropic env expressing vector and a retroviral vector coding for β-gal and neo$^r$ were co-introduced into the gag/pol intermediate clones, transient and stable supernatants harvested and β-gal titers determined on 3T3 target cells using either a standard blue X-gal staining procedure or a "Galactolight assay." Briefly, this assay allows rapid determination of β-gal vector titers by chemi-luminescent detection of transfer of β-gal expression to HT 1080 target cells. (Tripix, New Bedford, Mass.). Expression was compared to a standard curve for transfer of expression versus titer generated by serial dilutions of a known titer reference β-gal vector.

The titer results for the HT 1080 gag/pol intermediates are shown below in Table 7.

TABLE 7

Transient β-gal titers from
transduced pools of HT 1080 gag/pol intermediates

| Clone# | Transient β-gal titer (CFU/ml) | x-fold titer decrease (HTSCV21:HT 1080 gag/pol intermediate) |
|---|---|---|
| 1 | 178 | 11 |
| 2 | 750 | 3 |
| 6 | 345 | 6 |
| 12 | 728 | 3 |
| 14 | 545 | 4 |
| 18 | 113 | 18 |
| 38 | 263 | 8 |
| 41 | 1100 | 2 |
| 42 | (3) | (660) |
| 47 | 83 | 24 |
| 53 | 573 | 3 |
| 57 | 95 | 21 |
| 59 | 850 | 2 |
| 62 | 518 | 4 |
| 67 | 440 | 5 |
| 69 | 0 | — |
| 70 | 375 | 5 |
| 90 | 1300 | 2 |
| HTSCV21 | 1975 | |

11 out of 18 clones gave a titer potential that was 2–6 fold lower in comparison to HTSCV21. The titer results for the D17 gag/pol intermediate clones are shown below in Table 8.

TABLE 8

Transient β-gal titers from transduced pools of D17gag/pol intermediates and stable β-gal titers from transduced and G-418 selected D17gag/pol intermediates

| Clone# | Transient β-gal titer (CFU/ml) | x-fold titer decrease (D17 4-15: D17 gag/pol intermediates) | Stable β-gal titer (light units) | x-fold titer decrease |
|---|---|---|---|---|
| 2 | 165 | 473 | 80.1 | 14 |
| 10 | 95 | 821 | 44.3 | 25 |
| 42 | 270 | 289 | 27.8 | 40 |
| 55 | 990 | 79 | 246.7 | 5 |
| 60 | 220 | 354 | 67.8 | 16 |
| 65 | 495 | 158 | 280.5 | 4 |
| 71 | 605 | 129 | 77.0 | 14 |
| 72 | 0 | — | 95.9 | 12 |
| 74 | 1.7E4 | 5 | 1497.3 | no decrease |
| 75 | 2100 | 37 | 1180.3 | no decrease |
| 84 | 3400 | 23 | 300.3 | 4 |
| 92 | 1600 | 49 | 2013.7 | no decrease |
| D17 4-15 | 7.8E4 | | 1112.3 | |

The transient titers show a strong decrease in titer potential when compared to D17 4-15, but for the stable titers, six out of the 12 gag/pol intermediates show 0–6 fold decrease in comparison to D17 4-15.

A total of 6 D17 and 4 HT 1080 gag/pol intermediates with the highest titer potential were co-transfected with the env expression plasmid pCMV-b/envam described in Example 12 and a methotrexate$^r$ expressing marker plasmid into the HT 1080 and D17gag/pol intermediate clones via CapO$_4$-precipitation using the ProFection kit from Promega according to manufacturer's protocol (Promega, Madison, Wis.). The transfected cells were selected with media containing methotrexate at a concentration of $2 \times 10^{-7}$ M until untransfected control cells were dead. HT 1080 and D17 derived PCL pools were dilution cloned into 96-well microtiter plates according to standard protocols where clonality was ensured by seeding cell densities that yield a maximum of 30% of wells with cell growth. Several hundred HT 1080 and D17 derived PCL clones named HAII and DAII, respectively, were isolated and analyzed for titer potential.

Briefly, five rounds of titer potential analysis were carried out using various retroviral vectors. The DA or HA PCL controls (PCT #WO 92/05266) were included as a reference for high titer potential PCLs. In the first round, the PCL clones were transduced in 24-well plates with the β-gal coding retroviral vector DX/ND7 (WO 95/16852) at an moi of 5–10 in the presence of 8 μg/ml polybrene, transient supernatants harvested, filtered (0.45 μm), HT 1080 target cells transduced and transient β-gal titer determined using a standard Galactolight procedure following manufacturer's instructions (Tropix, Bedford, Mass.). In the second round, the same transduction assay as described for the first round was repeated with the top clones from round one using standardized PCL cell numbers. In the following titer potential analysis rounds, the top clones from round two were used to transduce with several retroviral vectors, supernatant from transient and stable pools were harvested, filtered, HT 1080 target cells transduced, and transient and stable titers determined.

Data on the titer potential analysis of the second round of screening is shown below in Table 9 on a small selection of representative DAII and HAII PCL clones.

TABLE 9

Transient β-gal titer on VCL pools from transduced HAII and DAII PCLs determined by Galactolight readout

| Clone# | Transient β-gal titer (Galactolight, light units) | x-fold decrease in titer potential (DA:DAII, HA:HAII) |
|---|---|---|
| D-17 based PCLs called DAII | | |
| DAII (based on pCI-GPM#74 intermediate) | | |
| 20 | 3 | — |
| 30 | 69 | 14 |
| 47 | 19 | 51 |
| 49 | 1 | — |
| 55 | 145 | 7 |
| 60 | 1 | — |
| 67 | 8 | — |
| 70 | 45 | 22 |
| DA | 978 | |
| DAII (based on pCI-GPM#75 intermediate) | | |
| 7 | 47 | 19 |
| 32 | 202 | 5 |
| 40 | 27 | 33 |
| 60 | 15 | 61 |
| 70 | 7 | — |
| 72 | 1 | — |
| DA | 901 | |
| HT-1080 based PCLs called HAII | | |
| HAII (based on pSCV10/5'3'tr.intermediate#12) | | |
| 6 | 147 | 10 |
| 11 | 8 | — |
| 12 | 56 | 27 |
| 18 | 45 | 34 |
| 44 | 113 | 13 |
| 51 | 2 | — |
| 54 | 2 | — |
| 56 | 83 | 18 |
| 57 | 115 | 13 |
| 65 | 133 | 11 |
| 66 | 104 | 15 |
| 78 | 195 | 8 |
| 86 | 125 | 12 |

TABLE 9-continued

Transient β-gal titer on VCL pools from transduced HAII and DAII PCLs determined by Galactolight readout

| Clone# | Transient β-gal titer (Galactolight, light units) | x-fold decrease in titer potential (DA:DAII, HA:HAII) |
|---|---|---|
| 87 | 77 | 20 |
| 88 | 259 | 6 |
| 90 | 196 | 8 |
| 91 | 91 | 17 |
| HA | 1508 | |
| HAII (based on pSCV10/5'3'tr.#41) | | |
| 4 | 48 | 31 |
| 9 | 84 | 18 |
| 15 | 157 | 10 |
| 18 | 174 | 9 |
| 37 | 111 | 14 |
| 55 | 357 | 4 |
| 58 | 140 | 11 |
| 75 | 164 | 9 |
| 92 | 57 | 28 |
| HA | 1570 | |

The top DAII and HAII PCL clones gave a 4–5 fold reduced titer potential when measured as a transient β-gal pool. A large percentage of these DAII and HAII PCL clones gave a 10–15 fold decrease in titer potential.

The top DAII and HAII clones were further tested for their titer potential using various retroviral vectors. Table 10 below shows a summary of titer potentials on VCL pools of the top HAII clones, with HAII#41#55 as the overall best PCL.

TABLE 10

| PCL clone# | transient factor VIII | stable PLAP (BAAP) | stable neo (BAAP) | stable neo (KT-1) | transient hGH | transient factor VIII |
|---|---|---|---|---|---|---|
| HAII | | | | | | |
| 12#78 | 1.1E5 | 5.0E4 | 1.6E4 | 5.3E5 | 36,000 | 7.7E4 |
| 12#86 | *8.8E4* | 6.6E4 | *1.1E4* | 8.4E5 | 29,200 | 7.1E4 |
| 12#88 | *1.1E4* | 3.2E4 | *8.6E4* | 8.2E5 | 34,500 | 1.1E5 |
| 12#90 | 9.4E4 | 1.0E5 | 6.4E4 | 9.4E5 | 37,700 | 1.1E5 |
| 41#18 | 7.0E4 | 6.2E4 | 2.0E4 | 1.3E5 | 34,400 | 1.8E5 |
| 41#55 | *9.9E4* | 6.3E5 | *1.7E5* | *1.1E6* | 44,000 | 1.3E5 |
| 41#58 | 8.9E4 | 4.8E4 | 8.8E3 | 5.1E5 | 38,700 | 4.3E4 |
| 41#75 | 1.1E5 | 1.4E5 | 3.2E4 | 8.7E5 | 34,300 | 1.5E5 |
| HA | 5.3E5 | 4.1E4 | 2.1E4 | 5.0E5 | 38,300 | 3.7E5 |
|  | *1.3E5* |  | *1.6E4* | *1.1E7* | *39,300* |  |
| DA | 3.9E4 | 1.0E6 | 4.0E5 | 5.9E5 | 45,700 | 1.9E5 |
|  | *7.3E3* |  | *8.4E6* | *4.8E6* | *52,500* |  |

Values in italics must be compared to the control PCL values (DA, HA) in italics Differences in titer potential were observed, depending not only on which PCL clone was used but also which gene of interest was expressed in the retroviral vector.

Comparison of the 8 top HAII clones with titers on VCL pools from various rounds of titer potential assays. The B-domain deleted factor VIII, human placental alkaline phosphatase plus neo$^r$ (BAAP), human growth hormone (hGH) and HIVenv/rev plus neo$^r$ (KT-1) expressing retroviral vectors were used to transduce the HAII PCLs. Transient and stable supernatants were tested on HT 1080 target cells. The readout for hGH is in units and the other titers are in CFU/ml.

B. Production of PCLs without any sequence overlap between PCL components

This example describes the production of PCLs with the gag/pol expression plasmid cassette pCI-WGPM described in Example 13 F and the env expression plasmid pCMV-b/envam described in Example 12 E. PCLs with these gag/pol and env expression plasmids in conjunction with the retroviral vector derived from pBA-5b (Example 9) result in producer cell lines where sequence overlap between all three areas of homology is completely eliminated (FIG. 22 C). The cell lines HT 1080 (ATCC #CCL 121) and D17 (ATCC #CCL 183) were used as parent cell lines to establish the PCLs.

Briefly, gag/pol plasmid pCI-WGPM was co-transfected together with a phleomycin$^r$ expressing marker plasmid into HT 1080 and D17 cells, selected and dilution cloned as described above. HT 1080 and D17 derived clones were isolated and analyzed for intracellular p30 expression levels as described above. Results of the p30 Western are shown below in Table 11.

TABLE 11

HT 1080 and D17 derived clones screened for intracellular p30 levels after introduction of gag/pol expression cassette pCI-WGPM

| Gag/pol intermediates | #clones screened for p30 | #clones positive for p30 — (%) | p30 expression levels |
|---|---|---|---|
| D-17g/p (pCI-WGPM) | 82 | 36 (44%) | 3–4 clones have p30 levels comparable to D17 4-15 |
| HT-1080g/p (pCI-WGPM) | 96 | 26 (27%) | 3–4 clones have p30 levels that are comparable to HTSCV21 |

The 12 HT 1080 and 22 D17 gag/pol intermediates with the highest p30 expression levels were analyzed for titer potential as described above. The titer results for the HT 1080 gag/pol intermediates are shown below in Table 12.

TABLE 12

Transient β-gal titers from transduced pools of HT 1080 gag/pol intermediates (pCI-WGPM)

| Clone# | Transient β-gal titer (CFU/ml) | x-fold titer decrease (HTSCV21:HT 1080 gag/pol intermediate) |
|---|---|---|
| 10 | 217 | >9 |
| 12 | 28 | >71 |
| 23 | 670 | >3 |
| 29 | 565 | >4 |
| 34 | 950 | >2 |
| 35 | 398 | >5 |
| 45 | 280 | >7 |
| 52 | 670 | >3 |
| 53 | 600 | >3 |
| 71 | 590 | >3 |
| 86 | 480 | >4 |
| 87 | 55 | >36 |
| HTSCV21 | >2000 | |

The Galactolight readout for HTSCV10 was out of the range with >2000, therefore the above shown decrease in titer potential is likely to be higher. The titer results for the D17 gag/pol intermediates are shown below in Table 13.

TABLE 13

Transient β-gal titers from transduced pools of D17gag/pol (D17 g/p) intermediates and stable β-gal titers from transduced and G-418 selected pools of D17gag/pol intermediates

| Clone# | Transient β-gal titer (CFU/ml) | x-fold decrease (D17 4-15:D17g/p inter.) | Stable β-gal titer (CFU/ml) | x-fold decrease (D17 4-15:D17g/p inter.) | Transient β-gal (CFU/ml) | x-fold decrease (D17 4-15:D17g/p inter.) |
|---|---|---|---|---|---|---|
| 1 | 0 | — | | | | |
| 3 | 40 | >100 | | | | |
| 6 | 20 | >200 | | | | |
| 14 | 10 | >400 | | | | |
| 21 | 10 | >400 | | | | |
| 22 | 1380 | >3 | 800 | >5 | 2.1E4 | 9 |
| 27 | 30 | >133 | | | | |
| 41 | 100 | >40 | | | | |
| 47 | 30 | >133 | 730 | >6 | 90 | 2111 |
| 48 | 30 | >133 | | | | |
| 49 | 500 | >8 | 680 | >6 | 9.4E3 | 20 |
| 50 | 140 | >29 | | | | |
| 51 | 10 | >400 | | | | |
| 56 | 600 | >7 | 320 | >13 | 1.8E3 | 105 |
| 57 | 230 | >17 | | | 1.3E3 | 146 |
| 60 | 380 | >11 | 580 | >7 | 1.0E4 | 190 |
| 65 | 0 | — | | | | |
| 66 | 470 | >9 | 330 | >12 | 1.1E3 | 172 |
| 70 | 30 | >133 | | | | |
| 73 | 320 | >13 | 1.05E4 | 0 | | |
| 76 | 40 | >100 | | | | |
| 79 | 20 | >200 | | | | |
| D17 4-15 | >4000* | | >4000* | | 1.9E5 | |

*out of range

The titer potential measured within the range indicates decreases in titer potential of 10–200 fold in most clones.

A total of 6 D17 and 4 HT 1080 gag/pol intermediates with the highest titer potential were co-transfected with the env expression plasmid pCMV-b/envam, pools selected and dilution cloned as described above. Several hundred HT 1080 and D17 derived PCL clones named HAIIwob and DAIIwob, respectively, were isolated and analyzed for titer potential.

Briefly, several rounds of titer potential analysis were carried out using various retroviral vectors. The DA or HA PCL (PCT #WO 92/05266) controls were included as a reference for high titer potential PCLs. In the first round, the PCL clones were transduced in 24-well plates with the β-gal coding retroviral vector DX/ND7 (WO 95/16852) at an moi of 5–10 in the presence of 8 μg/ml polybrene, transient supernatants harvested, filtered (0.45 μm), HT 1080 target cells transduced and transient β-gal titer determined using a standard Galactolight transfer of expression procedure described previously. In the second round, the same transduction assay as described for the first round was repeated with the top clones from round one using standardized PCL cell numbers. In the third round, the top clones from round two were used to transduce with several retroviral vectors, supernatant from transient and stable pools harvested, filtered, HT 1080 target cells transduced and titers determined.

Data on the titer potential analysis of the first and second round of screening is shown below in Table 14 on a small selection of representative DAII and HAII PCL clones.

TABLE 14

Transient β-gal titer on VCL pools from transduced HAII and DAII PCLs determined by Galactolight readout

| Clone# | Transient β-gal titer (Galactolight, light units) | x-fold decrease in titer potential (DA:DAIIwob or HA:HAIIwob) |
|---|---|---|
| D-17 based PCLs called DAIIwob | | |
| DAIIwob (pCI-WGPM#60) | | |
| 7 | 21 | 27 |
| 11 | 6 | 93 |
| 21 | 2 | 279 |
| 30 | 14 | 40 |
| 33 | 51 | 11 |
| 41 | 30 | 19 |
| DA | 558 | |
| DAIIwob (pCI-WGPM#22) | | |
| 5 | 148 | 0 |
| 8 | 28 | 5 |
| 28 | 14 | 11 |
| 56 | 15 | 10 |
| 78 | 39 | 4 |
| 97 | 10 | 15 |
| DA | 153 | |
| HT-1080 based PCLs called HAIIwob | | |
| HAIIwob (pCI-WGPM)#34 | | |
| 4 | 8 | 128 |
| 7 | 9 | 114 |
| 35 | 7 | 147 |
| 43 | 4 | 257 |
| 53 | 5 | 205 |
| 65 | 9 | 114 |
| 66 | 10 | 103 |
| 77 | 19 | 54 |

TABLE 14-continued

Transient β-gal titer on VCL pools from transduced HAII and DAII PCLs determined by Galactolight readout

| Clone# | Transient β-gal titer (Galactolight, light units) | x-fold decrease in titer potential (DA:DAIIwob or HA:HAIIwob) |
|---|---|---|
| 79 | 6 | 171 |
| 80 | 4 | 257 |
| 95 | 4 | 257 |
| 105 | 2 | 500 |
| 115 | 9 | 114 |
| 118 | 6 | 171 |
| HA | 1026 | |

The best DAIIwob PCL clone shows a 4-fold reduction in titer but most clones show >10-fold reduction. The best HAIIwob PCL clone shows a 50-fold reduced titer potential and most HAIIwob clones have >100-fold reduced titer potential. In general, the DAII wob and HAIIwob PCL clones gave in average about a 5–50 fold lower titer potential when compared to DAII and HAII PCLs.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. A gag/pol expression cassette, comprising a promoter operably linked to a gag/pol gene, and a polyadenylation sequence, wherein a 5' terminal end of said gag/pol gene has been modified to contain codons which are degenerate for gag.

2. The gag/pol cassette according to claim 1 wherein the 5' terminal end of said gag/pol gene lacks a retroviral packaging signal sequence.

3. A gag/pol expression cassette, comprising a promoter operably linked to a gag/pol gene, and a polyadenylation sequence, wherein a 3' terminal end of said gag/pol gene has been deleted without affecting the biological activity of integrase.

4. The gag/pol expression cassette according to claim 3 wherein a 5' terminal end of said gag/pol gene has been deleted without affecting the biological activity of integrase.

5. The gag/pol expression cassette according to claim 3 wherein the 5' terminal end of said gag/pol gene lacks a retroviral packaging signal sequence.

6. The gag/pol expression cassette according to any one of claims 3 to 5 wherein said 3' terminal end has been deleted upstream of nucleotide 5751 of Sequence ID No. 1.

7. The gag/pol expression cassette according to any one of claims 1 to 5 wherein said promoter is a heterologous promoter.

8. The gag/pol expression cassette according to any one of claims 1 to 5 wherein said polyadenylation sequence is a heterologous polyadenylation sequence.

9. The gag/pol expression cassette according to claim 7 wherein said promoter is selected from the group consisting of CMV IE, the HSVTK promoter, RSV promoter, Adenovirus major-later promoter and the SV40 promoter.

10. The gag/pol expression cassette according to claim 8 wherein said heterologous polyadenylation sequence is selected from the group consisting of the SV40 late poly A signal and the SV40 early poly A signal.

11. An env expression cassette, comprising a promoter operably linked to an env gene, and a polyadenylation sequence, wherein no more than 6 retroviral nucleotides are included upstream of said env gene.

12. An env expression cassette, comprising a promoter operably linked to an env gene, and a polyadenylation sequence, wherein said env expression cassette does not contain a consecutive sequence of more than 8 nucleotides which are found in a gag/pol gene.

13. An env expression cassette, comprising a promoter operably linked to an env gene, and a polyadenylation sequence, wherein a 3' terminal end of said env gene has been deleted without affecting the biological activity of env.

14. The env expression cassette according to claim 13 wherein said 3' terminal end of said gene has been deleted such that a complete R peptide is not produced by said expression cassette.

15. The env expression cassette according to claim 14 wherein said env gene is derived from a type C retrovirus, and wherein the 3' terminal end has been deleted such that said env gene includes less than 18 nucleic acids which encode said R peptide.

16. The env expression cassette according to claim 14 wherein said 3' terminal end has been deleted downstream from nucleotide 7748 of Sequence ID No. 1.

17. The env expression cassette according to any one of claims 11 to 16 wherein said promoter is a heterologous promoter.

18. The env expression cassette according to claim 17 wherein said promoter is selected from the group consisting of CMV IE, the HSVTK promoter, RSV promoter, Adenovirus major-later promoter and the SV40 promoter.

19. The env expression cassette according to any one of claims 11 to 16 wherein said polyadenylation sequence is a heterologous polyadenylation sequence.

20. The env expression cassette according to claim 18 wherein said heterologous polyadenylation is selected from the group consisting of the SV40 late poly A signal and the SV40 early poly A signal.

21. A packaging cell line, comprising a gag/pol expression cassette and an env expression cassette, wherein said gag/pol expression cassette lacks a consecutive sequence of greater than 8 consecutive nucleotides which are found in said env expression cassette.

22. A packaging cell line, comprising a gag/pol expression cassette according to any one of claims 1 to 5, and an env expression cassette.

23. A packaging cell line, comprising a gag/pol expression cassette, and an env expression cassette according to claims 11 to 16.

24. A method of producing a packaging cell, comprising:
    (a) introducing a gag/pol expression cassette according to claims 1 to 5 into an animal cell;
    (b) selecting a cell containing a gag/pol expression cassette which expresses high levels of gag/pol;
    (c) introducing an env expression cassette into said selected cell; and
    (d) selecting a cell which expresses high levels of env, and thereby producing said packaging cell.

25. A method of producing a packaging cell, comprising:
    (a) introducing an env expression cassette according to claims 11 to 16 into an animal cell;
    (b) selecting a cell which expresses high levels of env;
    (c) introducing a gag/pol expression cassette into said selected cell; and
    (d) selecting a cell containing a gag/pol expression cassette which expresses high levels of gag/pol, and thereby producing said packaging cell.

26. A method of producing recombinant retroviral particles, comprising introducing a retrovector construct into the packaging cell of claim 24.

27. A packaging cell line, comprising a gag/pol expression cassette according to claim 6, and an env expression cassette.

28. A packaging cell line, comprising a gag/pol expression cassette according to claim 7, and an env expression cassette.

29. A packaging cell line, comprising a gag/pol expression cassette according to claim 9, and an env expression cassette.

30. A packaging cell line, comprising a gag/pol expression cassette according to claim 8, and an env expression cassette.

31. A packaging cell line, comprising a gag/pol expression cassette according to claim 10, and an env expression cassette.

32. A packaging cell line, comprising a gag/pol expression cassette, and an env expression cassette according to claim 17.

33. A packaging cell line, comprising a gag/pol expression cassette, and an env expression cassette according to claim 18.

34. A packaging cell line, comprising a gag/pol expression cassette, and an env expression cassette according to claim 19.

35. A packaging cell line, comprising a gag/pol expression cassette, and an env expression cassette according to claim 20.

36. A method of producing a packaging cell, comprising:
   (a) introducing a gag/pol expression cassette according to claim 6 into an animal cell;
   (b) selecting a cell containing a gag/pol expression cassette which expresses high levels of gag/pol;
   (c) introducing an env expression cassette into said selected cell; and
   (d) selecting a cell which expresses high levels of env, and thereby producing said packaging cell.

37. A method of producing a packaging cell, comprising:
   (a) introducing a gag/pol expression cassette according to claim 7 into an animal cell;
   (b) selecting a cell containing a gag/pol expression cassette which expresses high levels of gag/pol;
   (c) introducing an env expression cassette into said selected cell; and
   (d) selecting a cell which expresses high levels of env, and thereby producing said packaging cell.

38. A method of producing a packaging cell, comprising:
   (a) introducing a gag/pol expression cassette according to claim 9 into an animal cell;
   (b) selecting a cell containing a gag/pol expression cassette which expresses high levels of gag/pol;
   (c) introducing an env expression cassette into said selected cell; and
   (d) selecting a cell which expresses high levels of env, and thereby producing said packaging cell.

39. A method of producing a packaging cell, comprising:
   (a) introducing a gag/pol expression cassette according to claim 8 into an animal cell;
   (b) selecting a cell containing a gag/pol expression cassette which expresses high levels of gag/pol;
   (c) introducing an env expression cassette into said selected cell; and
   (d) selecting a cell which expresses high levels of env, and thereby producing said packaging cell.

40. A method of producing a packaging cell, comprising:
   (a) introducing an env expression cassette according to claim 17 into an animal cell;
   (b) selecting a cell which expresses high levels of env;
   (c) introducing a gag/pol expression cassette into said selected cell; and
   (d) selecting a cell containing a gag/pol expression cassette which expresses high levels of gag/pol, and thereby producing said packaging cell.

41. A method of producing a packaging cell, comprising:
   (a) introducing an env expression cassette according to claim 18 into an animal cell;
   (b) selecting a cell which expresses high levels of env;
   (c) introducing a gag/pol expression cassette into said selected cell; and
   (d) selecting a cell containing a gag/pol expression cassette which expresses high levels of gag/pol, and thereby producing said packaging cell.

42. A method of producing a packaging cell, comprising:
   (a) introducing an env expression cassette according to claim 19 into an animal cell;
   (b) selecting a cell which expresses high levels of env;
   (c) introducing a gag/pol expression cassette into said selected cell; and
   (d) selecting a cell containing a gag/pol expression cassette which expresses high levels of gag/pol, and thereby producing said packaging cell.

43. A method of producing a packaging cell, comprising:
   (a) introducing an env expression cassette according to claim 20 into an animal cell;
   (b) selecting a cell which expresses high levels of env;
   (c) introducing a gag/pol expression cassette into said selected cell; and
   (d) selecting a cell containing a gag/pol expression cassette which expresses high levels of gag/pol, and thereby producing said packaging cell.

44. A method of producing recombinant retroviral particles, comprising introducing a retrovector construct into the packaging cell of claim 25.

* * * * *

SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
      (A) LENGTH: 8332 base pairs
      (B) TYPE: nucleic acid
      (C) STRANDEDNESS: single
      (D) TOPOLOGY: linear (xi) SEQUENCE DESCRIPTION: SEQ ID NO: 1:

```
GCGCCAGTCC TCCGATTGAC TGAGTCGCCC GGGTACCCGT GTATCCAATA AACCCTCTTG      60

CAGTTGCATC CGACTTGTGG TCTCGCTGTT CCTTGGGAGG GTCTCCTCTG AGTGATTGAC     120

TACCCGTCAG CGGGGGTCTT TCATTTGGGG GCTCGTCCGG GATCGGGAGA CCCCTGCCCA     180

GGGACCACCG ACCCACCACC GGGAGGTAAG CTGGCCAGCA ACTTATCTGT GTCTGTCCGA     240

TTGTCTAGTG TCTATGACTG ATTTTATGCG CCTGCGTCGG TACTAGTTAG CTAACTAGCT     300

CTGTATCTGG CGGACCCGTG GTGGAACTGA CGAGTTCGGA ACACCCGGCC GCAACCCTGG     360

GAGACGTCCC AGGGACTTCG GGGGCCGTTT TTGTGGCCCG ACCTGAGTCC AAAAATCCCG     420

ATCGTTTTGG ACTCTTTGGT GCACCCCCCT TAGAGGAGGG ATATGTGGTT CTGGTAGGAG     480

ACGAGAACCT AAAACAGTTC CCGCCTCCGT CTGAATTTTT GCTTTCGGTT TGGGACCGAA     540

GCCGCGCCGC GCGTCTTGTC TGCTGCAGCA TCGTTCTGTG TTGTCTCTGT CTGACTGTGT     600

TTCTGTATTT GTCTGAGAAT ATGGGCCAGA CTGTTACCAC TCCCTTAAGT TTGACCTTAG     660

GTCACTGGAA AGATGTCGAG CGGATCGCTC ACAACCAGTC GGTAGATGTC AAGAAGAGAC     720

GTTGGGTTAC CTTCTGCTCT GCAGAATGGC CAACCTTTAA CGTCGGATGG CCGCGAGACG     780

GCACCTTTAA CCGAGACCTC ATCACCCAGG TTAAGATCAA GGTCTTTTCA CCTGGCCCGC     840

ATGGACACCC AGACCAGGTC CCCTACATCG TGACCTGGGA AGCCTTGGCT TTTGACCCCC     900

CTCCCTGGGT CAAGCCCTTT GTACACCCTA AGCCTCCGCC TCCTCTTCCT CCATCCGCCC     960

CGTCTCTCCC CCTTGAACCT CCTCGTTCGA CCCCGCCTCG ATCCTCCCTT TATCCAGCCC    1020
```

```
TCACTCCTTC TCTAGGCGCC AAACCTAAAC CTCAAGTTCT TTCTGACAGT GGGGGGCCGC    1080

TCATCGACCT ACTTACAGAA GACCCCCCGC CTTATAGGGA CCCAAGACCA CCCCCTTCCG    1140

ACAGGGACGG AAATGGTGGA GAAGCGACCC CTGCGGGAGA GGCACCGGAC CCCTCCCCAA    1200

TGGCATCTCG CCTACGTGGG AGACGGGAGC CCCCTGTGGC CGACTCCACT ACCTCGCAGG    1260

CATTCCCCCT CCGCGCAGGA GGAAACGGAC AGCTTCAATA CTGGCCGTTC TCCTCTTCTG    1320

ACCTTTACAA CTGGAAAAAT AATAACCCTT CTTTTTCTGA AGATCCAGGT AAACTGACAG    1380

CTCTGATCGA GTCTGTTCTC ATCACCCATC AGCCCACCTG GGACGACTGT CAGCAGCTGT    1440

TGGGGACTCT GCTGACCGGA GAAGAAAAAC AACGGGTGCT CTTAGAGGCT AGAAAGGCGG    1500

TGCGGGGCGA TGATGGGCGC CCCACTCAAC TGCCCAATGA AGTCGATGCC GCTTTTCCCC    1560

TCGAGCGCCC AGACTGGGAT TACACCACCC AGGCAGGTAG GAACCACCTA GTCCACTATC    1620

GCCAGTTGCT CCTAGCGGGT CTCCAAAACG CGGGCAGAAG CCCCACCAAT TTGGCCAAGG    1680

TAAAAGGAAT AACACAAGGG CCCAATGAGT CTCCCTCGGC CTTCCTAGAG AGACTTAAGG    1740

AAGCCTATCG CAGGTACACT CCTTATGACC CTGAGGACCC AGGGCAAGAA ACTAATGTGT    1800

CTATGTCTTT CATTTGGCAG TCTGCCCCAG ACATTGGGAG AAAGTTAGAG AGGTTAGAAG    1860

ATTTAAAAAA CAAGACGCTT GGAGATTTGG TTAGAGAGGC AGAAAAGATC TTTAATAAAC    1920

GAGAAACCCC GGAAGAAAGA GAGGAACGTA TCAGGAGAGA AACAGAGGAA AAAGAAGAAC    1980

GCCGTAGGAC AGAGGATGAG CAGAAAGAGA AAGAAAGAGA TCGTAGGAGA CATAGAGAGA    2040

TGAGCAAGCT ATTGGCCACT GTCGTTAGTG GACAGAAACA GGATAGACAG GGAGGAGAAC    2100

GAAGGAGGTC CCAACTCGAT CGCGACCAGT GTGCCTACTG CAAAGAAAAG GGGCACTGGG    2160

CTAAAGATTG TCCCAAGAAA CCACGAGGAC CTCGGGGACC AAGACCCCAG ACCTCCCTCC    2220

TGACCCTAGA TGACTAGGGA GGTCAGGGTC AGGAGCCCCC CCCTGAACCC AGGATAACCC    2280

TCAAAGTCGG GGGGCAACCC GTCACCTTCC TGGTAGATAC TGGGGCCCAA CACTCCGTGC    2340

TGACCCAAAA TCCTGGACCC CTAAGTGATA AGTCTGCCTG GGTCCAAGGG CTACTGGAG    2400

GAAAGCGGTA TCGCTGGACC ACGGATCGCA AAGTACATCT AGCTACCGGT AAGGTCACCC    2460

ACTCTTTCCT CCATGTACCA GACTGTCCCT ATCCTCTGTT AGGAAGAGAT TTGCTGACTA    2520

AACTAAAAGC CCAAATCCAC TTTGAGGGAT CAGGAGCTCA GGTTATGGGA CCAATGGGGC    2580

AGCCCCTGCA AGTGTTGACC CTAAATATAG AAGATGAGCA TCGGCTACAT GAGACCTCAA    2640

AAGAGCCAGA TGTTTCTCTA GGGTCCACAT GGCTGTCTGA TTTTCCTCAG GCCTGGGCGG    2700

AAACCGGGGG CATGGGACTG GCAGTTCGCC AAGCTCCTCT GATCATACCT CTGAAAGCAA    2760

CCTCTACCCC CGTGTCCATA AAACAATACC CCATGTCACA AGAAGCCAGA CTGGGGATCA    2820

AGCCCCACAT ACAGAGACTG TTGGACCAGG GAATACTGGT ACCCTGCCAG TCCCCCTGGA    2880

ACACGCCCCT GCTACCCGTT AAGAAACCAG GGACTAATGA TTATAGGCCT GTCCAGGATC    2940

TGAGAGAAGT CAACAAGCGG GTGGAAGACA TCCACCCCAC CGTGCCCAAC CCTTACAACC    3000

TCTTGAGCGG GCTCCCACCG TCCCACCAGT GGTACACTGT GCTTGATTTA AAGGATGCCT    3060

TTTTCTGCCT GAGACTCCAC CCCACCAGTC AGCCTCTCTT CGCCTTTGAG TGGAGAGATC    3120

CAGAGATGGG AATCTCAGGA CAATTGACCT GGACCAGACT CCCACAGGGT TTCAAAAACA    3180

GTCCCACCCT GTTTGATGAG GCACTGCACA GAGACCTAGC AGACTTCCGG ATCCAGCACC    3240

CAGACTTGAT CCTGCTACAG TACGTGGATG ACTTACTGCT GGCCGCCACT TCTGAGCTAG    3300

ACTGCCAACA AGGTACTCGG GCCCTGTTAC AAACCCTAGG GAACCTCGGG TATCGGGCCT    3360
```

```
CGGCCAAGAA AGCCCAAATT TGCCAGAAAC AGGTCAAGTA TCTGGGGTAT CTTCTAAAAG    3420

AGGGTCAGAG ATGGCTGACT GAGGCCAGAA AAGAGACTGT GATGGGGCAG CCTACTCCGA    3480

AGACCCCTCG ACAACTAAGG GAGTTCCTAG GGACGGCAGG CTTCTGTCGC CTCTGGATCC    3540

CTGGGTTTGC AGAAATGGCA GCCCCCTTGT ACCCTCTCAC CAAAACGGGG ACTCTGTTTA    3600

ATTGGGGCCC AGACCAACAA AAGGCCTATC AAGAAATCAA GCAAGCTCTT CTAACTGCCC    3660

CAGCCCTGGG GTTGCCAGAT TTGACTAAGC CCTTTGAACT CTTTGTCGAC GAGAAGCAGG    3720

GCTACGCCAA AGGTGTCCTA ACGCAAAAAC TGGGACCTTG GCGTCGGCCG GTGGCCTACC    3780

TGTCCAAAAA GCTAGACCCA GTAGCAGCTG GGTGGCCCCC TTGCCTACGG ATGGTAGCAG    3840

CCATTGCCGT ACTGACAAAG GATGCAGGCA AGCTAACCAT GGGACAGCCA CTAGTCATTC    3900

TGGCCCCCCA TGCAGTAGAG GCACTAGTCA AACAACCCCC CGACCGCTGG CTTTCCAACG    3960

CCCGGATGAC TCACTATCAG GCCTTGCTTT TGGACACGGA CCGGGTCCAG TTCGGACCGG    4020

TGGTAGCCCT GAACCCGGCT ACGCTGCTCC CACTGCCTGA GGAAGGGCTG CAACACAACT    4080

GCCTTGATAT CCTGGCCGAA GCCCACGGAA CCCGACCCGA CCTAACGGAC CAGCCGCTCC    4140

CAGACGCCGA CCACACCTGG TACACGGATG GAAGCAGTCT CTTACAAGAG GGACAGCGTA    4200

AGGCGGGAGC TGCGGTGACC ACCGAGACCG AGGTAATCTG GGCTAAAGCC CTGCCAGCCG    4260

GGACATCCGC TCAGCGGGCT GAACTGATAG CACTCACCCA GGCCCTAAAG ATGGCAGAAG    4320

GTAAGAAGCT AAATGTTTAT ACTGATAGCC GTTATGCTTT TGCTACTGCC CATATCCATG    4380

GAGAAATATA CAGAAGGCGT GGGTTGCTCA CATCAGAAGG CAAAGAGATC AAAAATAAAG    4440

ACGAGATCTT GGCCCTACTA AAAGCCCTCT TTCTGCCCAA AAGACTTAGC ATAATCCATT    4500

GTCCAGGACA TCAAAAGGGA CACAGCGCCG AGGCTAGAGG CAACCGGATG GCTGACCAAG    4560

CGGCCCGAAA GGCAGCCATC ACAGAGACTC CAGACACCTC TACCCTCCTC ATAGAAAATT    4620

CATCACCCTA CACCTCAGAA CATTTTCATT ACACAGTGAC TGATATAAAG GACCTAACCA    4680

AGTTGGGGGC CATTTATGAT AAAACAAAGA AGTATTGGGT CTACCAAGGA AAACCTGTGA    4740

TGCCTGACCA GTTTACTTTT GAATTATTAG ACTTTCTTCA TCAGCTGACT CACCTCAGCT    4800

TCTCAAAAAT GAAGGCTCTC CTAGAGAGAA GCCACAGTCC CTACTACATG CTGAACCGGG    4860

ATCGAACACT CAAAAATATC ACTGAGACCT GCAAAGCTTG TGCACAAGTC AACGCCAGCA    4920

AGTCTGCCGT TAAACAGGGA ACTAGGGTCC GCGGGCATCG GCCCGGCACT CATTGGGAGA    4980

TCGATTTCAC CGAGATAAAG CCCGGATTGT ATGGCTATAA ATATCTTCTA GTTTTTATAG    5040

ATACCTTTTC TGGCTGGATA GAAGCCTTCC CAACCAAGAA AGAAACCGCC AAGGTCGTAA    5100

CCAAGAAGCT ACTAGAGGAG ATCTTCCCCA GGTTCGGCAT GCCTCAGGTA TTGGGAACTG    5160

ACAATGGGCC TGCCTTCGTC TCCAAGGTGA GTCAGACAGT GGCCGATCTG TTGGGGATTG    5220

ATTGGAAATT ACATTGTGCA TACAGACCCC AAAGCTCAGG CCAGGTAGAA AGAATGAATA    5280

GAACCATCAA GGAGACTTTA ACTAAATTAA CGCTTGCAAC TGGCTCTAGA GACTGGGTGC    5340

TCCTACTCCC CTTAGCCCTG TACCGAGCCC GCAACACGCC GGGCCCCCAT GGCCTCACCC    5400

CATATGAGAT CTTATATGGG GCACCCCCGC CCCTTGTAAA CTTCCCTGAC CCTGACATGA    5460

CAAGAGTTAC TAACAGCCCC TCTCTCCAAG CTCACTTACA GGCTCTCTAC TTAGTCCAGC    5520

ACGAAGTCTG GAGACCTCTG GCGGCAGCCT ACCAAGAACA ACTGGACCGA CCGGTGGTAC    5580

CTCACCCTTA CCGAGTCGGC GACACAGTGT GGGTCCGCCG ACACCAGACT AAGAACCTAG    5640

AACCTCGCTG GAAAGGACCT TACACAGTCC TGCTGACCAC CCCCACCGCC CTCAAAGTAG    5700

ACGGCATCGC AGCTTGGATA CACGCCGCCC ACGTGAAGGC TGCCGACCCC GGGGGTGGAC    5760
```

```
CATCCTCTAG ACTGACATGG CGCGTTCAAC GCTCTCAAAA CCCCTTAAAA ATAAGGTTAA   5820

CCCGCGAGGC CCCCTAATCC CCTTAATTCT TCTGATGCTC AGAGGGGTCA GTACTGCTTC   5880

GCCCGGCTCC AGTCCTCATC AAGTCTATAA TATCACCTGG GAGGTAACCA ATGGAGATCG   5940

GGAGACGGTA TGGGCAACTT CTGGCAACCA CCCTCTGTGG ACCTGGTGGC CTGACCTTAC   6000

CCCAGATTTA TGTATGTTAG CCCACCATGG ACCATCTTAT TGGGGCTAG  AATATCAATC   6060

CCCTTTTTCT TCTCCCCCGG GGCCCCCTTG TTGCTCAGGG GGCAGCAGCC CAGGCTGTTC   6120

CAGAGACTGC GAAGAACCTT TAACCTCCCT CACCCCTCGG TGCAACACTG CCTGGAACAG   6180

ACTCAAGCTA GACCAGACAA CTCATAAATC AAATGAGGGA TTTTATGTTT GCCCCGGGCC   6240

CCACCGCCCC CGAGAATCCA AGTCATGTGG GGGTCCAGAC TCCTTCTACT GTGCCTATTG   6300

GGGCTGTGAG ACAACCGGTA GAGCTTACTG GAAGCCCTCC TCATCATGGG ATTTCATCAC   6360

AGTAAACAAC AATCTCACCT CTGACCAGGC TGTCCAGGTA TGCAAAGATA ATAAGTGGTG   6420

CAACCCCTTA GTTATTCGGT TTACAGACGC CGGGAGACGG GTTACTTCCT GGACCACAGG   6480

ACATTACTGG GGCTTACGTT TGTATGTCTC CGGACAAGAT CCAGGGCTTA CATTTGGGAT   6540

CCGACTCAGA TACCAAAATC TAGGACCCCG CGTCCCAATA GGGCCAAACC CCGTTCTGGC   6600

AGACCAACAG CCACTCTCCA AGCCCAAACC TGTTAAGTCG CCTTCAGTCA CCAAACCACC   6660

CAGTGGGACT CCTCTCTCCC CTACCCAACT TCCACCGGCG GGAACGGAAA ATAGGCTGCT   6720

AAACTTAGTA GACGGAGCCT ACCAAGCCCT CAACCTCACC AGTCCTGACA AAACCCAAGA   6780

GTGCTGGTTG TGTCTAGTAG CGGGACCCCC CTACTACGAA GGGGTTGCCG TCCTGGGTAC   6840

CTACTCCAAC CATACCTCTG CTCCAGCCAA CTGCTCCGTG GCCTCCCAAC ACAAGTTGAC   6900

CCTGTCCGAA GTGACCGGAC AGGGACTCTG CATAGGAGCA GTTCCCAAAA CACATCAGGC   6960

CCTATGTAAT ACCACCCAGA CAAGCAGTCG AGGGTCCTAT TATCTAGTTG CCCCTACAGG   7020

TACCATGTGG GCTTGTAGTA CCGGGCTTAC TCCATGCATC TCCACCACCA TACTGAACCT   7080

TACCACTGAT TATTGTGTTC TTGTCGAACT CTGGCCAAGA GTCACCTATC ATTCCCCCAG   7140

CTATGTTTAC GGCCTGTTTG AGAGATCCAA CCGACACAAA AGAGAACCGG TGTCGTTAAC   7200

CCTGGCCCTA TTATTGGGTG GACTAACCAT GGGGGGAATT GCCGCTGGAA TAGGAACAGG   7260

GACTACTGCT CTAATGGCCA CTCAGCAATT CCAGCAGCTC CAAGCCGCAG TACAGGATGA   7320

TCTCAGGGAG GTTGAAAAAT CAATCTCTAA CCTAGAAAAG TCTCTCACTT CCCTGTCTGA   7380

AGTTGTCCTA CAGAATCGAA GGGGCCTAGA CTTGTTATTT CTAAAAGAAG GAGGGCTGTG   7440

TGCTGCTCTA AAAGAAGAAT GTTGCTTCTA TGCGGACCAC ACAGGACTAG TGAGAGACAG   7500

CATGGCCAAA TTGAGAGAGA GGCTTAATCA GAGACAGAAA CTGTTTGAGT CAACTCAAGG   7560

ATGGTTTGAG GGACTGTTTA ACAGATCCCC TTGGTTTACC ACCTTGATAT CTACCATTAT   7620

GGGACCCCTC ATTGTACTCC TAATGATTTT GCTCTTCGGA CCCTGCATTC TTAATCGATT   7680

AGTCCAATTT GTTAAAGACA GGATATCAGT GGTCCAGGCT CTAGTTTTGA CTCAACAATA   7740

TCACCAGCTG AAGCCTATAG AGTACGAGCC ATAGATAAAA TAAAAGATTT TATTTAGTCT   7800

CCAGAAAAAG GGGGGAATGA AAGACCCCAC CTGTAGGTTT GGCAAGCTAG CTTAAGTAAC   7860

GCCATTTTGC AAGGCATGGA AAATACATA  ACTGAGAATA GAGAAGTTCA GATCAAGGTC   7920

AGGAACAGAT GGAACAGCTG AATATGGGCC AAACAGGATA TCTGTGGTAA GCAGTTCCTG   7980

CCCCGGCTCA GGGCCAAGAA CAGATGGAAC AGCTGAATAT GGGCCAAACA GGATATCTGT   8040

GGTAAGCAGT TCCTGCCCCG GCTCAGGGCC AAGAACAGAT GGTCCCCAGA TGCGGTCCAG   8100
```

```
CCCTCAGCAG TTTCTAGAGA ACCATCAGAT GTTTCCAGGG TGCCCCAAGG ACCTGAAATG      8160

ACCCTGTGCC TTATTTGAAC TAACCAATCA GTTCGCTTCT CGCTTCTGTT CGCGCGCTTC      8220

TGCTCCCCGA GCTCAATAAA AGAGCCCACA ACCCCTCACT CGGGGCGCCA GTCCTCCGAT      8280

TGACTGAGTC GCCCGGGTAC CCGTGTATCC AATAAACCCT CTTGCAGTTG CA              8332
```

(2) INFORMATION FOR SEQ ID NO: 2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 2:

```
GGTAACAGTC TGGCCCGAAT TCTCAGACAA ATACAG                                36
```

(2) INFORMATION FOR SEQ ID NO: 3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 3:

```
CTGTATTTGT CTGAGAATTA AGGCTAGACT GTTACCAC                              38
```

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 4:

```
ATATATATAT ATCGATACCA TG                                               22
```

(2) INFORMATION FOR SEQ ID NO: 5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 5:

```
GGCGCCAAAC CTAAAC                                                      16
```

(2) INFORMATION FOR SEQ ID NO: 6:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 6:

(xi) SEQUENCE DESCRIPTION: SEQ ID NO: 6:

(2) INFORMATION FOR SEQ ID NO: 7:

(i) SEQUENCE CHARACTERISTICS:
        (A) LENGTH: 21 base pairs (B) TYPE: nucleic acid
            (C) STRANDEDNESS: single
            (D) TOPOLOGY: linear (xi) SEQUENCE DESCRIPTION: SEQ ID NO: 7:

ACCATCCTCT GGACGGACAT G                                              21

(2) INFORMATION FOR SEQ ID NO: 8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 8:

ACCCGGCCGT GGACGGACAT G                                              21

(2) INFORMATION FOR SEQ ID NO: 9:
    (i) SEQUENCE CHARACTERISTICS:
            (A) LENGTH: 449 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 20..442

(xi) SEQUENCE DESCRIPTION: SEQ ID NO: 9:

```
ATATATATAT ATCGATACC ATG GGG CAA ACC GTG ACT ACC CCT CTG TCC CTC        52
                    Met Gly Gln Thr Val Thr Thr Pro Leu Ser Leu
                     1               5                      10

ACA CTG GGC CAT TGG AAG GAC GTG GAA AGA ATT GCC CAT AAT CAA AGC        100
Thr Leu Gly His Trp Lys Asp Val Glu Arg Ile Ala His Asn Gln Ser
             15                  20                  25

GTG GAC GTC AAA AAA CGC AGG TGG GTG ACA TTT TGT AGC GCC GAG TGG        148
Val Asp Val Lys Lys Arg Arg Trp Val Thr Phe Cys Ser Ala Glu Trp
         30                  35                  40

CCC ACA TTC AAT GTT GGC TGG CCT AGG GAT GGA ACT TTC AAT CGC GAT        196
Pro Thr Phe Asn Val Gly Trp Pro Arg Asp Gly Thr Phe Asn Arg Asp
     45                  50                  55

CTG ATT ACT CAA GTG AAA ATT AAA GTG TTC AGC CCC GGA CCC CAC GGC        244
Leu Ile Thr Gln Val Lys Ile Lys Val Phe Ser Pro Gly Pro His Gly
 60                  65                  70                  75

CAT CCC GAT CAA GTT CCT TAT ATT GTC ACA TGG GAG GCT CTC GCT TTC        292
His Pro Asp Gln Val Pro Tyr Ile Val Thr Trp Glu Ala Leu Ala Phe
                 80                  85                  90

GAT CCA CCA CCT TGG GTG AAA CCA TTC GTG CAT CCC AAA CCA CCT CCA        340
Asp Pro Pro Pro Trp Val Lys Pro Phe Val His Pro Lys Pro Pro Pro
             95                 100                 105

CCC CTC CCA CCC AGC GCT CCT AGC CTG CCC TTG GAG CCC CCA CGA AGC        388
Pro Leu Pro Pro Ser Ala Pro Ser Leu Pro Leu Glu Pro Pro Arg Ser
         110                 115                 120

ACA CCA CCC AGG AGC AGC TTG TAC CCT GCT CTG ACC CCC AGC CTC GGC        436
Thr Pro Pro Arg Ser Ser Leu Tyr Pro Ala Leu Thr Pro Ser Leu Gly
     125                 130                 135

GCC AAA CCTAAAC                                                        449
Ala Lys
140
```

(2) INFORMATION FOR SEQ ID NO: 10:

(i) SEQUENCE CHARACTERISTICS:

(A) LENGTH: 141 amino acids
       (B) TYPE: amino acid
       (D) TOPOLOGY: linear (ii) MOLECULE TYPE: protein (xi) SEQUENCE DESCRIPTION: SEQ ID NO: 10:

Met Gly Gln Thr Val Thr Thr Pro Leu Ser Leu Thr Leu Gly His Trp
 1               5                  10                  15

Lys Asp Val Glu Arg Ile Ala His Asn Gln Ser Val Asp Val Lys Lys
                20                  25                  30

Arg Arg Trp Val Thr Phe Cys Ser Ala Glu Trp Pro Thr Phe Asn Val
            35                  40                  45

Gly Trp Pro Arg Asp Gly Thr Phe Asn Arg Asp Leu Ile Thr Gln Val
 50                  55                  60

Lys Ile Lys Val Phe Ser Pro Gly Pro His Gly His Pro Asp Gln Val
 65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
                100                 105                 110

Ala Pro Ser Leu Pro Leu Glu Pro Pro Arg Ser Thr Pro Pro Arg Ser
            115                 120                 125

Ser Leu Tyr Pro Ala Leu Thr Pro Ser Leu Gly Ala Lys
130                 135                 140

(2) INFORMATION FOR SEQ ID NO: 11:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..420

(xi) SEQUENCE DESCRIPTION: SEQ ID NO: 11:

ATG GGC CAG ACT GTT ACC ACT CCC TTA AGT TTG ACC TTA GGT CAC TGG      48
Met Gly Gln Thr Val Thr Thr Pro Leu Ser Leu Thr Leu Gly His Trp
 1               5                  10                  15

AAA GAT GTC GAG CGG ATC GCT CAC AAC CAG TCG GTA GAT GTC AAG AAG      96
Lys Asp Val Glu Arg Ile Ala His Asn Gln Ser Val Asp Val Lys Lys
                20                  25                  30

AGA CGT TGG GTT ACC TTC TGC TCT GCA GAA TGG CCA ACC TTT AAC GTC     144
Arg Arg Trp Val Thr Phe Cys Ser Ala Glu Trp Pro Thr Phe Asn Val
            35                  40                  45

GGA TGG CCG CGA GAC GGC ACC TTT AAC CGA GAC CTC ATC ACC CAG GTT     192
Gly Trp Pro Arg Asp Gly Thr Phe Asn Arg Asp Leu Ile Thr Gln Val
 50                  55                  60

AAG ATC AAG GTC TTT TCA CCT GGC CCG CAT GGA CAC CCA GAC CAG GTC     240
Lys Ile Lys Val Phe Ser Pro Gly Pro His Gly His Pro Asp Gln Val
 65                  70                  75                  80

CCC TAC ATC GTG ACC TGG GAA GCC TTG GCT TTT GAC CCC CCT CCC TGG     288
Pro Tyr Ile Val Thr Trp Glu Ala Leu Ala Phe Asp Pro Pro Pro Trp
                85                  90                  95

GTC AAG CCC TTT GTA CAC CCT AAG CCT CCG CCT CCT CTT CCT CCA TCC     336
Val Lys Pro Phe Val His Pro Lys Pro Pro Pro Leu Pro Pro Ser
                100                 105                 110

GCC CCG TCT CTC CCC CTT GAA CCT CCT CGT TCG ACC CCG CCT CGA TCC     384

```
Ala Pro Ser Leu Pro Leu Glu Pro Pro Arg Ser Thr Pro Pro Arg Ser
        115                 120                 125
TCC CTT TAT CCA GCC CTC ACT CCT TCT CTA GGC GCC                      420
Ser Leu Tyr Pro Ala Leu Thr Pro Ser Leu Gly Ala
        130                 135                 140
```

(2) INFORMATION FOR SEQ ID NO: 12:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Gly Gln Thr Val Thr Thr Pro Leu Ser Leu Thr Leu Gly His Trp
 1               5                  10                  15
Lys Asp Val Glu Arg Ile Ala His Asn Gln Ser Val Asp Val Lys Lys
            20                  25                  30
Arg Arg Trp Val Thr Phe Cys Ser Ala Glu Trp Pro Thr Phe Asn Val
        35                  40                  45
Gly Trp Pro Arg Asp Gly Thr Phe Asn Arg Asp Leu Ile Thr Gln Val
    50                  55                  60
Lys Ile Lys Val Phe Ser Pro Gly Pro His Gly His Pro Asp Gln Val
65                  70                  75                  80
Pro Tyr Ile Val Thr Trp Glu Ala Leu Ala Phe Asp Pro Pro Pro Trp
                85                  90                  95
Val Lys Pro Phe Val His Pro Lys Pro Pro Pro Leu Pro Pro Ser
            100                 105                 110
Ala Pro Ser Leu Pro Leu Glu Pro Pro Arg Ser Thr Pro Pro Arg Ser
        115                 120                 125
Ser Leu Tyr Pro Ala Leu Thr Pro Ser Leu Gly Ala
        130                 135                 140
```

(2) INFORMATION FOR SEQ ID NO: 13:

(i) SEQUENCE CHARACTERISTICS:
        (A) LENGTH: 2001 base pairs
        (B) TYPE: nucleic acid
        (C) STRANDEDNESS: single
        (D) TOPOLOGY: linear (xi) SEQUENCE DESCRIPTION: SEQ ID NO: 13:

```
GGCCGACACC CAGAGTGGAC CATCCTCTGG ACGGACATGG CGCGTTCAAC GCTCTCAAAA      60
CCCCCTCAAG ATAAGATTAA CCCGTGGAAG CCCTTAATAG TCATGGGAGT CCTGTTAGGA     120
GTAGGGATGG CAGAGAGCCC CCATCAGGTC TTTAATGTAA CCTGGAGAGT CACCAACCTG     180
ATGACTGGGC GTACCGCCAA TGCCACCTCC CTCCTGGGAA CTGTACAAGA TGCCTTCCCA     240
AAATTATATT TTGATCTATG TGATCTGGTC GGAGAGGAGT GGGACCCTTC AGACCAGGAA     300
CCGTATGTCG GGTATGGCTG CAAGTACCCC GCAGGGAGAC AGCGGACCCG GACTTTTGAC     360
TTTTACGTGT GCCCTGGGCA TACCGTAAAG TCGGGGTGTG GGGACCAGG AGAGGGCTAC      420
TGTGGTAAAT GGGGGTGTGA AACCACCGGA CAGGCTTACT GGAAGCCCAC ATCATCGTGG     480
GACCTAATCT CCCTTAAGCG CGGTAACACC CCCTGGGACA CGGGATGCTC TAAAGTTGCC     540
TGTGGCCCCT GCTACGACCT CTCCAAAGTA TCCAATTCCT TCCAAGGGGC TACTCGAGGG     600
GGCAGATGCA ACCCTCTAGT CCTAGAATTC ACTGATGCAG GAAAAAAGGC TAACTGGGAC     660
```

```
GGGCCCAAAT CGTGGGGACT GAGACTGTAC CGGACAGGAA CAGATCCTAT TACCATGTTC      720

TCCCTGACCC GGCAGGTCCT TAATGTGGGA CCCCGAGTCC CCATAGGGCC CAACCCAGTA      780

TTACCCGACC AAAGACTCCC TTCCTCACCA ATAGAGATTG TACCGGCTCC ACAGCCACCT      840

AGCCCCCTCA ATACCAGTTA CCCCCCTTCC ACTACCAGTA CACCCTCAAC CTCCCCTACA      900

AGTCCAAGTG TCCCACAGCC ACCCCCAGGA ACTGGAGATA GACTACTAGC TCTAGTCAAA      960

GGAGCCTATC AGGCGCTTAA CCTCACCAAT CCCGACAAGA CCCAAGAATG TTGGCTGTGC     1020

TTAGTGTCGG GACCTCCTTA TTACGAAGGA GTAGCGGTCG TGGGCACTTA TACCAATCAT     1080

TCCACCGCTC CGGCCAACTG TACGGCCACT TCCCAACATA AGCTTACCCT ATCTGAAGTG     1140

ACAGGACAGG GCCTATGCAT GGGGGCAGTA CCTAAAACTC ACCAGGCCTT ATGTAACACC     1200

ACCCAAAGCG CCGGCTCAGG ATCCTACTAC CTTGCAGCAC CCGCCGGAAC AATGTGGGCT     1260

TGCAGCACTG GATTGACTCC CTGCTTGTCC ACCACGGTGC TCAATCTAAC CACAGATTAT     1320

TGTGTATTAG TTGAACTCTG GCCCAGAGTA ATTTACCACT CCCCCGATTA TATGTATGGT     1380

CAGCTTGAAC AGCGTACCAA ATATAAAAGA GAGCCAGTAT CATTGACCCT GGCCCTTCTA     1440

CTAGGAGGAT TAACCATGGG AGGGATTGCA GCTGGAATAG GGACGGGGAC CACTGCCTTA     1500

ATTAAAACCC AGCAGTTTGA GCAGCTTCAT GCCGCTATCC AGACAGACCT CAACGAAGTC     1560

GAAAAGTCAA TTACCAACCT AGAAAAGTCA CTGACCTCGT TGTCTGAAGT AGTCCTACAG     1620

AACCGCAGAG GCCTAGATTT GCTATTCCTA AAGGAGGGAG GTCTCTGCGC AGCCCTAAAA     1680

GAAGAATGTT GTTTTTATGC AGACCACACG GGGCTAGTGA GAGACAGCAT GGCCAAATTA     1740

AGAGAAAGGC TTAATCAGAG ACAAAAACTA TTTGAGACAG GCCAAGGATG GTTCGAAGGG     1800

CTGTTTAATA GATCCCCCTG GTTTACCACC TTAATCTCCA CCATCATGGG ACCTCTAATA     1860

GTACTCTTAC TGATCTTACT CTTTGGACCT TGCATTCTCA ATCGATTGGT CCAATTTGTT     1920

AAAGACAGGA TCTCAGTGGT CCAGGCTCTG GTTTTGACTC AGCAATATCA CCAGCTAAAA     1980

CCCATAGAGT ACGAGCCATG A                                              2001

(2) INFORMATION FOR SEQ ID NO: 14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 14:

CTAGCTAGCT AG                                                          12

(2) INFORMATION FOR SEQ ID NO: 15:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO: 15:

ATATATATAT ATCGATACCA TGGGCAAAC CGTGACTACC CCTCTGTCCC TCACACTGGC        60

CCAA                                                                   64

(2) INFORMATION FOR SEQ ID NO: 16:

(i) SEQUENCE CHARACTERISTICS:
        (A) LENGTH: 52 base pairs
```

(B) TYPE: nucleic acid
        (C) STRANDEDNESS: single
        (D) TOPOLOGY: linear (xi) SEQUENCE DESCRIPTION: SEQ ID NO: 16:

TTGATTATGG GCAATTCTTT CCACGTCCTT CCAATGGCCC AGTGTGAGGG AC                52

(2) INFORMATION FOR SEQ ID NO: 17:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 17:

AGAATTGCCC ATAATCAAAG CGTGGACGTC AAAAAACGCA GGTGGGTGAC ATTTTGTAGC        60

GCCGAGTGGC CC                                                           72

(2) INFORMATION FOR SEQ ID NO: 18:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 18:

AAGTTCCATC CCTAGGCCAG CCAACATTGA ATGTGGGCCA CTCGGCGCTA CA                52

(2) INFORMATION FOR SEQ ID NO: 19:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 19:

GGCCTAGGGA TGGAACTTTC AATCGCGATC TGATTACTCA AGTGAAAATT AAAGTGTTCA        60

GCCCCGGACC CC                                                           72

(2) INFORMATION FOR SEQ ID NO: 20:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 20:

GTGACAATAT AAGGAACTTG ATCGGGATGG CCGTGGGGTC CGGGGCTGAA CA                52

(2) INFORMATION FOR SEQ ID NO: 21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 21:

AGTTCCTTAT ATTGTCACAT CGGAGGCTCT CGCTTTCGAT CCACCACCTT GGGTGAAACC        60

ATTCGTGCAT CC                                                           72

(2) INFORMATION FOR SEQ ID NO: 22:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 22

```
AGGAGCGCTG GGTGGGAGGG GTGGAGGTGG TTTGGGATGC ACGAATGGTT TC          52
```

(2) INFORMATION FOR SEQ ID NO: 23

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 23:

```
CTCCCACCCA GCGCTCCTAG CCTGCCCTTG GAGCCCCCAC GAAGCACACC ACCCAGGAGC  60

AGCTTGTACC CT                                                     72
```

(2) INFORMATION FOR SEQ ID NO: 24:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 24:

```
GTTTAGGTTT GGCGCCGAGG CTGGGGGTCA GAGCAGGGTA CAAGCTGCTC CT          52
```

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 25:

```
ATATATATAT ATCGATACC                                              19
```

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 26:

```
GTTTAGGTTT GGCGCCGAGG                                             20
```

(2) INFORMATION FOR SEQ ID NO: 27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 27:

```
GGGAGTGGTA ACAGTCTGGC CTTAATTCTC AG                              32
```

(2) INFORMATION FOR SEQ ID NO: 28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 28:

```
CGGTCGACCT CGAGAATTAA TAC                                        23
```

(2) INFORMATION FOR SEQ ID NO: 29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 29:

```
CTGGGAGACG TCCCAGGGAC TTC                                        23
```

(2) INFORMATION FOR SEQ ID NO: 30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 30:

```
GGCCAGACTG TTACCACTCC CTGAAGTTTG AC                              32
```

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 31:

```
CATCGATAAA ATAAAAGATT TTATTTAGTC                                 30
```

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 32:

```
CAAATGAAAG ACCCCCGCTG AC                                         22
```

(2) INFORMATION FOR SEQ ID NO: 33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 33:

```
CCTATGAGCT CGCCTTCTAG TTGCCAGC                                   28
```

(2) INFORMATION FOR SEQ ID NO: 34:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 34:

CCTATGAATT CGCGGCCGCC ATAGAGCCCA CCGCATCC                  38

(2) INFORMATION FOR SEQ ID NO: 35:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO: 35:

TATATATGAG CTCTAATAAA ATGAGGAAAT TGCATCGCAT TGTC              44

(2) INFORMATION FOR SEQ ID NO: 36:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 36:

CCTATGAATT CGCGGCCGCA TAGAATGACA CCTACTCAGA CAATGCGA          48

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 37:

GCTCGTTTAG TGAACCGTCA G                                  21

(2) INFORMATION FOR SEQ ID NO: 38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 38:

TATCCGAGCT CATGGCTCGT ACTCTATGG                          29

(2) INFORMATION FOR SEQ ID NO: 39:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 39:

CACCTATGCT AGCCACCATG GCGCGTTCAA CGCTCTC                   37

(2) INFORMATION FOR SEQ ID NO: 40:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 40:

```
CACCTATGCG GCCGCTCATG GCTCGTACTC TATGGG                             36
```

(2) INFORMATION FOR SEQ ID NO: 41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO: 41:

```
CACCTATGCG GCCGCCACCA TGGCGCGTTC AACGCTCTC                          39
```

(2) INFORMATION FOR SEQ ID NO: 42:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (xi) SEQUENCE DESCRIPTION: SEQ ID NO: 42:

```
ATCGATACCA TGGGGCAAAC CGTGACTACC CCTCTGTCCC TCACACTGGG CCATTGGAAG    60

GACGTGGAAA GAATTGCCCA TAATCAAAGC GTGGACGTCA AAAAACGCAG GTGGGTGACA   120

TTTTGTAGCG CCGAGTGGCC CACATTCAAT GTTGGCTGGC CTAGGGATGG AACTTTCAAT   180

CGCGATCTGA TTACTCAAGT GAAAATTAAA GTGTTCAGCC CCGGACCCCA CGGCCATCCC   240

GATCAAGTTC CTTATATTGT CACATGGGAG GCTCTCGCTT TCGATCCACC ACCTTGGGTG   300

AAACCATTCG TGCATCCCAA ACCACCTCCA CCCCTCCCAC CCAGCGCTCC TAGCCTGCCC   360

TTGGAGCCCC CACGAAGCAC ACCACCCAGG AGCAGCTTGT ACCCTGCTCT GACCCCCAGC   420

CTCGGCGCC                                                          429
```

(2) INFORMATION FOR SEQ ID NO: 43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 43:

```
CGAATCGATA CCATGGGCCA GACTGTTACC AC                                 32
```

(2) INFORMATION FOR SEQ ID NO: 44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 44:

```
CATTCTGCAG AGCAGAAGGT AAC                                           23
```

(2) INFORMATION FOR SEQ ID NO: 45:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 45:

TAAGCGGCCG CTTA                                                                        14